US012760075B2

(12) United States Patent
Rodino-Klapac

(10) Patent No.: US 12,760,075 B2
(45) Date of Patent: Oct. 13, 2026

(54) GENE THERAPY WITH DYSFERLIN DUAL VECTORS

(71) Applicant: Research Institute at Nationwide Children's Hospital, Columbus, OH (US)

(72) Inventor: Louise Rodino-Klapac, Grove City, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 952 days.

(21) Appl. No.: 17/924,820

(22) PCT Filed: May 12, 2021

(86) PCT No.: PCT/US2021/031998
§ 371 (c)(1),
(2) Date: Nov. 11, 2022

(87) PCT Pub. No.: WO2021/231577
PCT Pub. Date: Nov. 18, 2021

(65) Prior Publication Data

US 2023/0279065 A1 Sep. 7, 2023

Related U.S. Application Data

(60) Provisional application No. 63/024,338, filed on May 13, 2020.

(51) Int. Cl.

| | |
|---|---|
| ***C07K 14/47*** | (2006.01) |
| ***A61K 9/00*** | (2006.01) |
| ***A61K 48/00*** | (2006.01) |
| ***C12N 15/86*** | (2006.01) |

(52) U.S. Cl.
CPC ........ *C07K 14/4707* (2013.01); *A61K 9/0019* (2013.01); *A61K 48/0058* (2013.01); *C12N 15/86* (2013.01); *C12N 2750/14143* (2013.01)

(58) Field of Classification Search
CPC ................ C07K 14/4707; C12N 15/86; C12N 2750/14143
See application file for complete search history.

(56) References Cited

U.S. PATENT DOCUMENTS

| | | | |
|---|---|---|---|
| 2003/0110526 A1 | 6/2003 | Brown et al. | |
| 2019/0048362 A1 | 2/2019 | Kyostio-Moore et al. | |
| 2020/0010521 A1* | 1/2020 | Hirsch ............... | C07K 14/4707 |

FOREIGN PATENT DOCUMENTS

| | | | |
|---|---|---|---|
| KR | 10-2019-0028389 A | 3/2019 | |
| WO | WO-00/11157 A1 | 3/2000 | |
| WO | WO-2017/218866 A1 | 12/2017 | |
| WO | WO-2020/033026 A1 | 2/2020 | |

OTHER PUBLICATIONS

Punta et al. The Rough Guide to in Silico Function Prediction, or How to Use Sequence and Structure Information to Predict Protein Function. Comput Biol 4(10): e1000160, 2008 (Year: 2008).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Song et al. A Single Amino Acid Change (Asp 533Ala53) Converts Survivin from Anti-apoptotic to Pro-apoptotic. Molecular Biology of the Cell, 15:1287-1296, Mar. 2004 (Year: 2004).*
Defeo-Jones et al. Substitution of Lysine for Arginine at Position 42 of Human Transforming Growth Factor-a Eliminates Biological Activity without Changing Internal Disulfide Bonds. Molecular and Cellular Biology, Sep. 1989, p. 4083-4086 (Year: 1989).*
Bork. Powers and Pitfalls in Sequence Analysis: The 70% Hurdle. Genome Research, 2000; 10:398-400 (Year: 2000).*
International Search Report and Written Opinion dated Sep. 14, 2021, from application No. PCT/US2021/031998.
Potter, et al., "Systemic Delivery of Dysferlin Overlap Vectors Provides Long-Term Gene Expression and Functional Improvement for Dysferlinopathy", Human Gene Therapy, 29(7):749-762 (Jul. 2018).
Database Geneseq [Online], "Human dysferlin polypeptide isoform 8 encoding DNA SEQ IQ 12", Feb. 8, 2018, 4 pages.
Sondergaard, et al., "AAV.Dysferlin Overlap Vectors Restore Function in Dysferlinopathy Animal Models", Annals of Clinical and Translational Neurology, 2015, vol. 2, No. 3, pp. 256-270.
Lostal et al., "Efficient recovery of dysferlin deficiency by dual adeon-associated vector-mediated gene transfer", Human Molecular Genetics, 2010, vol. 19, No. 10, 1897-1907.

* cited by examiner

*Primary Examiner* — Vanessa L. Ford
*Assistant Examiner* — Sandra Carter
(74) *Attorney, Agent, or Firm* — Foley & Lardner LLP

(57) ABSTRACT

Recombinant polynucleotides encoding fragments of a human dysferlin protein are described herein. In addition, plasmids, viral vectors, dual vector systems, cells, and compositions comprising such recombinant polynucleotides are further described. Such recombinant polynucleotides, plasmids, viral vectors, dual vector systems, cells, and compositions may be used to treat dysferlinopathies.

15 Claims, 17 Drawing Sheets

Specification includes a Sequence Listing.

GENE THERAPY WITH DYSFERLIN DUAL VECTORS

CROSS-REFERENCE TO RELATED APPLICATION

This application is a national stage entry under 35 U.S.C. § 371 of International Application No. PCT/US2021/031998, filed May 12, 2021, which claims priority under 35 U.S.C. § 119(e) of U.S. Provisional Application No. 63/024,338, filed May 13, 2020, the contents of which are hereby incorporated by reference in its entirety into the present application.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 106887_8070_SL.txt; Size: 129,123 bytes, created; May 11, 2021.

TECHNICAL FIELD

This disclosure provides polynucleotides comprising fragments of the human dysferlin gene and plasmids, viral vectors, cells, and compositions comprising such polynucleotides, and methods of using such polynucleotides, plasmids, viral vectors, and compositions to treat subjects with dysferlin deficiency, such as limb girdle muscular dystrophy type 2B, Myoshi Myopathy, and distal anterior compartment myopathy.

BACKGROUND

Dysferlinopathies are autosomal recessive disorders including limb girdle muscular dystrophy type 2B (LGMD2B), Miyoshi myopathy, and distal anterior compartment myopathy, collectively known as the dysferlinopathies. Limb Girdle Muscular Dystrophy type 2B (LGMD2B) represents one of the most common LGMDs in the United States with worldwide reports of incidence of 1/100,000-1/200,000. Miyoshi Myopathy is more limited distal lower extremity form of dysferlinopathy. In fact, in considering the disease spectrum, LGMD2B often begins distal with atrophy of gastrocnemius muscle and then spreads over time to affect proximal muscles. Loss of dysferlin leads to a progressive form of dystrophy with chronic muscle fiber loss, inflammation, fat replacement and fibrosis all leading to deteriorating muscle weakness.

The dysferlin gene is large, with 55 exons so far identified spanning at least 150 kb of genomic DNA. These exons predict a cDNA of approximately 6.5 kb and a protein of 2,088 amino acids. Dysferlin is a 237 kDa protein composed of a C-terminal hydrophobic transmembrane domain and a longer cytoplasmic oriented hydrophilic region with multiple C2 domains. A growing body of work has shown that loss of dysferlin compromises $Ca^{2+}$-dependent membrane repair in skeletal muscle (Song et al., Proc. Natl. Acad. Sci USA 98: 4084-4088, 2001; Schnepp et al., J. Virol. 77:3495-3504, 2003). In addition dysferlin has been shown to interact with other proteins involved in membrane repair including annexins A1 and A2, AHNAK, and caveolins-3. The importance of this system is emphasized when considering that skeletal muscle is mechanically active and predisposed to injury; thus, a robust membrane resealing mechanism must be present. Absent or mutant dysferlin leads to impaired membrane repair and a cascade of events starting with muscle fiber necrosis resulting in muscle fiber loss and progressive limb weakness. The loss of muscle fiber regenerative capacity is thought to be a contributory consequence of dysferlin deficiency. Dysferlin has also been associated with vesicle trafficking and endocytosis, T tubule formation and others.

Mutations in the dysferlin gene cause allelic autosomal recessive disorders including limb girdle muscular dystrophy type 2B (LGMD2B), Miyoshi myopathy and distal anterior compartment myopathy, collectively known as the dysferlinopathies (see, e.g., Grose et al., PloS one 7:e39233, 2012, Bansal et al., Nature 423, 168-172, 2003, Moore, S. A., et al., J. Neuropathol. Exp. Neurol 65: 995-1003, 2006, Rosales et al., Muscle Nerv 42:14-21, 2010, Sondergaard et al., Anns of Clin. Trans. Neurol. 2:256-270, 2015, Evesson et al., J. Biol. Chem. 285: 28529-28539, 2010, and Klinge et al., Soc. Exp. Biol. 21: 1768-1776, 2007, each of which are incorporated by reference in their entireties). A less common phenotype of dysferlin deficiency presents with rigid spine syndrome (Klinge et al., Muscle Nerve 41: 166-173, 2010, which is incorporated by reference in its entirety). Typically patients present in their early twenties with slowly progressive weakness and high serum creatine kinase (CK). Approximately one-third of patients become wheelchair-dependent within 15 years of onset. Clinically the heart is spared and cognitive function is not affected. The phenotypic variants with a relatively restricted distribution of muscle weakness set the stage for potential regional gene replacement therapy that could greatly impact quality of life for this disorder (Grose et al., PLOS One 7:e39233, 2012, Barton et al., Muscle Nerve 42: 22-29, 2010). Single nucleotide changes are the typical DYSF gene mutation, which also favor success in gene transfer serving to protect the transgene product from immunorejection (Rodine-Klapac et al., Mol. Ther. 18: 109-117, 2010, Mendell et al., N. Eng. J. Med. 363: 1429-1437, 2010, Mendell et al., Ann. Neurol. 66:290-297, 2009, each of which are incorporated by reference in their entireties).

There is no cure or treatment for dysferlinopathies. Collectively, pre-clinical studies that have assessed gene replacement or surrogate gene replacement have shown that multiple strategies exhibit some efficacy in restoring membrane repair. The dysferlin gene includes 55 exons encompassing 150 kb of genomic DNA with its associated cDNA at 6.5 kb. However, for gene replacement, the packaging limit of AAV is 4.7 kb, which is below dysferlin's cDNA sequence at 6.5 kb. Thus, there is a need for a treatment for LGMD2B, necessitating a new mechanism that is capable of delivering the functional full-length dysferlin protein to a subject in need.

SUMMARY

Disclosed herein is a recombinant polynucleotide encoding a fragment of a human dysferlin (hDYSF) protein, wherein the recombinant polynucleotide comprises a first nucleotide sequence, wherein the first nucleotide sequence consists of: (a) the nucleotide sequence of SEQ ID NO: 1, 6, or 18; (b) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (c) the nucleotide sequence of SEQ ID NO: 13 or 15; (d) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (e) a nucleotide sequence encoding the fragment of the hDYSF protein, wherein the fragment consists of the amino acid sequence of SEQ ID NO: 9; or (f) a nucleotide sequence that is at least 90%, 91%, 92%, 93%, 94%, 95%, 96%, 97%, 98%, or 99% identical to the nucleotide sequence of (e) across the full length of the nucleotide sequence of (e).

In some embodiments, the recombinant polynucleotide further comprises one or more additional nucleotide sequences selected from an inverted terminal repeat (ITR), a promoter, an intron, a selection marker, or an origin of replication (ORI).

In some embodiments, the recombinant polynucleotide further comprises an additional nucleotide sequence comprising an ITR. In some embodiments, the ITR is an AAV ITR. In some embodiments, the AAV ITR is an AAV2 ITR or an AAV3 ITR. In some embodiments, the recombinant polynucleotide comprises two ITRs. In some embodiments, the ITR comprises the nucleotide sequence of SEQ ID NO: 3 or SEQ ID NO: 17.

In some embodiments, the recombinant polynucleotide further comprises an additional nucleotide sequence comprising a promoter. In some embodiments, the promoter is a muscle-specific promoter. In some embodiments, the muscle-specific promoter is selected from a human skeletal actin gene element, a cardiac actin gene element, a desmin promoter, a skeletal alpha-actin (ASKA) promoter, a troponin I (TNNI2) promoter, a myocytespecific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor. In some embodiments, muscle-specific promoter is a MHCK7 promoter. In some embodiments, the promoter is a recombinant promoter. In some embodiments, the recombinant promoter is a recombinant muscle-specific promoter. In some embodiments, the recombinant-muscle specific promoter is a recombinant myosin heavy chain-creatine kinase muscle-specific promoter. In some embodiments, the promoter comprises the nucleotide sequence of SEQ ID NO: 4.

In some embodiments, the recombinant polynucleotide further comprises an additional nucleotide sequence comprising an intron. In some embodiments, the intron comprises a 5' donor site, branch point, and/or 3' splice site. In some embodiments, the intron is a chimeric intron. In some embodiments, the intron comprises a 5' donor site from a human β-globin gene. In some embodiments, the intron comprises a branch point from an immunoglobulin G (IgG) heavy chain. In some embodiments, the intron comprises a 3' splice acceptor site from an immunoglobulin G (IgG) heavy chain In some embodiments, the intron comprises the nucleotide sequence of SEQ ID NO: 5.

In some embodiments, the recombinant polynucleotide further comprises an additional nucleotide sequence comprising a selection marker. In some embodiments, the selection marker is an antibiotic resistance gene. In some embodiments, the antibiotic resistance gene is a β-lactamase gene or kanamycin resistance gene. In some embodiments, the recombinant polynucleotide comprises the nucleotide sequence of SEQ ID NO: 6 or SEQ ID NO: 18. In some embodiments, the recombinant nucleotide does not further comprise a second polynucleotide sequence encoding a second fragment of the hDYSF protein.

In some embodiments, the recombinant nucleotide does not comprise an AAV sequence other than one or more ITRs.

In some embodiments, the recombinant nucleotide does not comprise a viral sequence other than one or more ITRs.

Disclosed herein is a recombinant polynucleotide sequence encoding a fragment of a human dysferlin protein, wherein the recombinant polynucleotide comprises a second nucleotide sequence, wherein the second nucleotide sequence consists of: (a) the nucleotide sequence of SEQ ID NO: 2, 8, or 19; (b) a nucleotide sequence that is at least 90%, 91%, 92%, 93%, 94%, 95%, 96%, 97%, 98%, or 99% identical to the nucleotide sequence of SEQ ID NO: 2, 8, or 19 across its respective full length of SEQ ID NO: 2, 8, or 19; (c) the nucleotide sequence of SEQ ID NO: 14 or 16; (d) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (e) a polynucleotide sequence encoding the fragment of the hDYSF protein, wherein the fragment of the hDYSF protein consists of the amino acid sequence of SEQ ID NO: 10; or (f) a polynucleotide sequence that is at least 90%, 91%, 92%, 93%, 94%, 95%, 96%, 97%, 98%, or 99% identical to the polynucleotide sequence of (e) across the full length of the nucleotide sequence of (d).

In some embodiments, the recombinant polynucleotide further comprises one or more additional nucleotide sequences comprising an inverted terminal repeat (ITR), a selection marker, an origin of replication (ORI), an untranslated region (UTR), or a polyadenylation (polyA) signal.

In some embodiments, the recombinant polynucleotide further comprises an additional nucleotide sequence comprising an ITR. In some embodiments, the ITR is an AAV ITR. In some embodiments, the AAV ITR is an AAV2 ITR or an AAV3 ITR. In some embodiments, the recombinant nucleotide comprises two ITRs. In some embodiments, the ITR comprises the nucleotide sequence of SEQ ID NO: 3 or 17.

In some embodiments, the recombinant polynucleotide further comprises a nucleotide sequence comprising a polyA signal. In some embodiments, the polyA signal is an artificial polyA signal. In some embodiments, the polyA signal comprises the nucleotide sequence of SEQ ID NO: 7.

In some embodiments, the recombinant polynucleotide further comprises an additional nucleotide sequence comprising a selection marker. In some embodiments, the selection marker is an antibiotic resistance gene. In some embodiments, the antibiotic resistance gene is a β-lactamase gene or kanamycin resistance gene. In some embodiments, the recombinant polynucleotide comprises the nucleotide sequence of SEQ ID NO: 8 or SEQ ID NO: 19.

In some embodiments, the recombinant nucleotide does not further comprise a first polynucleotide sequence encoding a first fragment of the hDYSF protein.

In some embodiments, the recombinant nucleotide does not comprise an AAV sequence other than one or more ITRs.

In some embodiments, the recombinant nucleotide does not comprise a viral sequence other than one or more ITRs.

Further disclosed herein is a dual adeno-associated viral (AAV) vector system comprising: (a) a first AAV vector, wherein the first AAV vector comprises a first recombinant polynucleotide encoding a N-terminal fragment of a human dysferlin (hDYSF) protein, wherein the first recombinant polynucleotide comprises a first nucleotide sequence, wherein the first nucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) a second AAV vector, wherein the second AAV vector comprises a second recombinant polynucleotide encoding a C-terminal fragment of a human dysferlin protein, wherein the second recombinant polynucleotide comprises a second nucleotide sequence, wherein the second nucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

Further disclosed herein is adeno-associated viral (AAV) vector comprising any of the recombinant polynucleotides disclosed herein. In some embodiments, the recombinant polynucleotide encodes an N-terminal fragment of a human dysferlin protein. In some embodiments, the recombinant polynucleotide encodes a C-terminal fragment of a human dysferlin protein. In some embodiments, the AAV vector is AAV-1, AAV-2, AAV-3, AAV-4, AAV-5, AAV-6, AAV-7, AAV-8, AAV-9, AAV-10, AAV-11, AAV-12, AAV-13, AAVrh.10, AAVrh.20, or AAVrh.74. In some embodiments, the AAV vector is AAVrh.74.

Further disclosed herein is a composition comprising any of the AAV vectors disclosed herein.

Further disclosed herein is a composition comprising (a) a first recombinant adeno-associated viral (rAAV) vector, wherein the first rAAV vector comprises a first recombinant polynucleotide encoding a N-terminal fragment of a human dysferlin (hDYSF) protein, wherein the first recombinant polynucleotide comprises a first nucleotide sequence, wherein the first nucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) a second rAAV vector, wherein the second rAAV vector comprises a second recombinant polynucleotide encoding a C-terminal fragment of a human dysferlin protein, wherein the second recombinant polynucleotide comprises a second nucleotide sequence, wherein the second nucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

In some embodiments, the molar ratio of first and second rAAV vectors is between about 100:1-1:100, about 10:1-1:10, about 2:1-1:2, or about 1:1.

Further disclosed herein is an adeno-associated viral (AAV) vector comprising: (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (c) a second ITR, wherein the polynucleotide is flanked by the first and second ITRs.

In some embodiments, the ITR is an AAV ITR. In some embodiments, the AAV ITR is an AAV2 ITR or an AAV3 ITR. In some embodiments, the first and/or second ITR comprise the nucleotide sequence of SEQ ID NO: 3 or 17.

In some embodiments, the AAV vector further comprises one or more additional polynucleotide sequences comprising a promoter, an intron, a selection marker, or an origin of replication (ORI).

In some embodiments, the AAV vector further comprises an additional polynucleotide sequence comprising a promoter. In some embodiments, the promoter is a muscle-specific promoter. In some embodiments, the muscle-specific promoter is a myosin heavy chain complex-E box muscle creatine kinase fusion enhancer/promoter. In some embodiments, the promoter is a recombinant promoter. In some embodiments, the recombinant promoter is a recombinant muscle-specific promoter. In some embodiments, the recombinant-muscle specific promoter is aMHCK7 promoter. In some embodiments, the promoter comprises the nucleotide sequence of SEQ ID NO: 4.

In some embodiments, the AAV vector further comprises an additional polynucleotide sequence comprising an intron. In some embodiments, the intron comprises a 5' donor site, branch point, and/or 3' splice site. In some embodiments, the intron is a chimeric intron. In some embodiments, the intron comprises a 5' donor site from a human β-globin gene. In some embodiments, the intron comprises a branch point from an immunoglobulin G (IgG) heavy chain. In some embodiments, the intron comprises a 3' splice acceptor site from an immunoglobulin G (IgG) heavy chain. In some embodiments, the intron comprises the nucleotide sequence of SEQ ID NO: 5.

In some embodiments, the AAV vector further comprises an additional polynucleotide sequence comprising a selection marker. In some embodiments, the selection marker is an antibiotic resistance gene. In some embodiments, the antibiotic resistance gene is a β-lactamase gene or kanamycin resistance gene. In some embodiments, the AAV vector comprises the nucleotide sequence of SEQ ID NO: 6 or SEQ ID NO: 15.

In some embodiments, the AAV vector does not further comprise a second polynucleotide sequence encoding a second fragment of the hDYSF protein.

In some embodiments, the AAV vector does not comprise an AAV sequence other than one or more ITRs.

In some embodiments, the AAV vector does not comprise a viral sequence other than one or more ITRs.

Further disclosed herein is an adeno-associated viral (AAV) vector comprising: (a) a first inverted terminal repeat (ITR); (b) a polynucleotide encoding a fragment of a human dysferlin protein, wherein the polynucleotide sequence consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide sequence of (v) across the full length of the nucleotide sequence of (v); and (c) a second ITR, wherein the polynucleotide is flanked by the first and second ITRs.

In some embodiments, the AAV vector further comprises one or more polynucleotide sequences comprising a selection marker, an origin of replication (ORI), an untranslated region (UTR), or a polyadenylation (polyA) signal.

In some embodiments, the ITR is an AAV ITR. In some embodiments, the AAV ITR is an AAV2 ITR or an AAV3 ITR. In some embodiments, the ITR comprises the nucleotide sequence of SEQ ID NO: 3 or 17.

In some embodiments, the AAV vector further comprises an additional polynucleotide sequence comprising a polyA signal. In some embodiments, the polyA signal is an artificial polyA signal. In some embodiments, the polyA signal comprises the nucleotide sequence of SEQ ID NO: 7.

In some embodiments, the AAV vector further comprises an additional polynucleotide sequence comprising a selection marker. In some embodiments, the selection marker is an antibiotic resistance gene. In some embodiments, the antibiotic resistance gene is a β-lactamase gene or kanamycin resistance gene.

In some embodiments, the AAV vector comprises the nucleotide sequence of SEQ ID NO: 8 or SEQ ID NO: 16.

In some embodiments, the AAV vector does not further comprise a second polynucleotide sequence encoding a second fragment of the hDYSF protein.

In some embodiments, the AAV vector does not comprise an AAV sequence other than one or more ITRs.

In some embodiments, the AAV vector does not comprise a viral sequence other than one or more ITRs.

Disclosed herein is a dual adeno-associated viral (AAV) vector system comprising: (I) a first AAV vector, wherein the first AAV vector comprises (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (c) a second ITR, wherein the polynucleotide is flanked by the first and second ITRs; and (II) a second AAV vector, wherein the second AAV vector comprises (a) a third inverted terminal repeat (ITR); (b) a polynucleotide encoding a fragment of a human dysferlin protein, wherein the polynucleotide consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide sequence of (v) across the full length of the nucleotide sequence of (v); and (c) a fourth ITR, wherein the polynucleotide is flanked by the third and fourth ITRs.

Further disclosed herein is an adeno-associated viral (AAV) packaging system comprising: (a) a plasmid comprising the recombinant polynucleotide disclosed herein; (b) an adenovirus helper plasmid; and (c) a rep-cap plasmid. In some instances, the adenovirus helper plasmid comprises pHELP plasmid.

Further disclosed herein is an adeno-associated viral packaging system comprising: (a) a plasmid comprising the recombinant polynucleotide disclosed herein; and (b) an adenovirus helper plasmid. In some instances, the adenovirus helper plasmid comprises pHELP plasmid.

Further disclosed herein is a method for producing an adeno-associated viral (AAV) vector, comprising contacting a cell with an AAV packaging system, wherein the AAV packaging system comprises: (a) a plasmid comprising the recombinant polynucleotide disclosed herein; (b) an adenovirus helper plasmid; and (c) a rep-cap plasmid. In some instances, the cell is a host cell, optionally a mammalian host cell, further optionally HEK293.

Further disclosed herein is a method for producing an adeno-associated viral (AAV) vector, comprising transducing a packaging cell line with an AAV packaging system, wherein the AAV packaging system comprises (a) a plasmid comprising an AAV expression cassette comprising any of the recombinant polynucleotides disclosed herein; and (b) an adenovirus helper plasmid, and wherein the packaging cell line expresses an adeno-associated viral rep and cap genes. In some instances, the AAV rep gene is Rep78. In some instances, the AAV cap gene is Rh74 cap gene.

Further disclosed herein is a cell comprising any of the recombinant polynucleotides disclosed herein.

Further disclosed herein is a cell comprising an AAV expression cassette, wherein the AAV expression cassette comprises any of the recombinant polynucleotides disclosed herein. In some instances, the plasmid comprising a polynucleotide that is at least 90%, 91%, 92%, 93%, 94%, 95%, 96%, 97%, 98%, or 99% identical to SEQ ID NO: 18 or 19. In some instances, the plasmid comprising a polynucleotide of SEQ ID NO: 18 or 19.

Further disclosed herein is a method of treating a dysferlinopathy, comprising administering to a subject in need thereof: (a) an effective amount of a first recombinant polynucleotide comprising a first polynucleotide sequence encoding an N-terminal of a human dysferlin (hDYSF) protein, wherein the first polynucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) an effective amount of a second recombinant polynucleotide comprising a second polynucleotide sequence encoding a C-terminal fragment of a human dysferlin protein, wherein the second polynucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

In some embodiments, the first polynucleotide is administered intramuscularly or intravenously. In some embodiments, the second polynucleotide is administered intramuscularly or intravenously.

In some embodiments, the first and second polynucleotides are administered simultaneously or sequentially.

In some embodiments, the dysferlinopathy is limb girdle muscular dystrophy type 2B (LGMD2B) or Miyoshi myopathy.

Further disclosed herein is a method of treating a dysferlinopathy, comprising administering to a subject in need thereof (a) an effective amount of a first adeno-associated viral (AAV) vector, wherein the first AAV vector comprises a first polynucleotide encoding an N-terminal of a human dysferlin (hDYSF) protein, wherein the first polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) an effective amount of a second AAV vector, wherein the second AAV vector comprises a second polynucleotide encoding a C-terminal fragment of a human dysferlin protein, wherein the second polynucleotide consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide of (v) across the full length of the nucleotide sequence of (v).

In some embodiments, the first AAV vector is administered intramuscularly or intravenously. In some embodiments, the second AAV vector is administered intramuscularly or intravenously. In some embodiments, the first and second AAV vectors are administered simultaneously.

In some embodiments, the dysferlinopathy is limb girdle muscular dystrophy type 2B (LGMD2B) or Miyoshi myopathy.

In some embodiments, a method of treating a dysferlinopathy comprises administering to a subject in need thereof an effective amount of any of the AAV dual vector systems disclosed herein.

In some embodiments, the AAV dual vector system is administered intramuscularly or intravenously.

In some embodiments, the dysferlinopathy is limb girdle muscular dystrophy type 2B (LGMD2B) or Miyoshi myopathy.

In some embodiments, a method of treating a dysferlinopathy comprises administering to a subject in need thereof an effective amount of any of the compositions disclosed herein.

In some embodiments, the composition is administered intramuscularly or intravenously.

In some embodiments, the dysferlinopathy is limb girdle muscular dystrophy type 2B (LGMD2B) or Miyoshi myopathy.

Further disclosed herein is use of a composition in the manufacture of a medicament to treat a dysferlinopathy in a subject in need thereof, wherein the composition comprises (a) a first recombinant polynucleotide comprising a first polynucleotide sequence encoding an N-terminal of a human dysferlin (hDYSF) protein, wherein the first polynucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) a second recombinant polynucleotide comprising a second polynucleotide sequence encoding a C-terminal fragment of a human dysferlin protein, wherein the second polynucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

In some embodiments, the first polynucleotide is administered intramuscularly or intravenously. In some embodiments, the second polynucleotide is administered intramuscularly or intravenously. In some embodiments, the first and second polynucleotides are administered simultaneously.

In some embodiments, the dysferlinopathy is limb girdle muscular dystrophy type 2B (LGMD2B) or Miyoshi myopathy.

Disclosed herein is use of a composition in the manufacture of a medicament to treat a dysferlinopathy in a subject in need thereof, wherein the composition comprises: (a) an effective amount of a first adeno-associated viral (AAV) vector, wherein the first AAV vector comprises a first polynucleotide sequence encoding an N-terminal of a human dysferlin (hDYSF) protein, wherein the first polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) an effective amount of a second adeno-associated viral (AAV) vector, wherein the second AAV vector comprises a second polynucleotide encoding a C-terminal fragment of a human dysferlin protein, wherein the second polynucleotide consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide of (v) across the full length of the nucleotide sequence of (v).

In some embodiments, the first AAV vector is administered intramuscularly or intravenously. In some embodiments, the second AAV vector is administered intramuscularly or intravenously. In some embodiments, the first and second AAV vectors are administered simultaneously.

In some embodiments, the dysferlinopathy is limb girdle muscular dystrophy type 2B (LGMD2B) or Miyoshi myopathy.

Disclosed herein is use of a composition in the manufacture of a medicament to treat a dysferlinopathy in a subject in need thereof, wherein the composition comprises any of the AAV dual vector systems disclosed herein.

In some embodiments, the composition is administered intramuscularly or intravenously.

In some embodiments, the dysferlinopathy is limb girdle muscular dystrophy type 2B (LGMD2B) or Miyoshi myopathy.

Disclosed herein is use of any of the compositions disclosed in the manufacture of a medicament to treat a dysferlinopathy in a subject in need thereof.

In some embodiments, the composition is administered intramuscularly or intravenously.

In some embodiments, the dysferlinopathy is limb girdle muscular dystrophy type 2B (LGMD2B) or Miyoshi myopathy.

In some embodiments, the effective amount of the first AAV vector is between about $1\times10^{6}$-$1\times10^{16}$ vg/kg, about $1\times10^{8}$-$1\times10^{15}$ vg/kg, or about $1\times10^{10}$-$1\times10^{14}$ vg/kg, based on a supercoiled DNA or plasmid as the quantitation standard.

In some embodiments, the effective amount of the second AAV vector is between about $1\times10^{6}$-$1\times10^{16}$ vg/kg, about $1\times10^{8}$-$1\times10^{15}$ vg/kg, or about $1\times10^{10}$-$1\times10^{14}$ vg/kg, based on a supercoiled DNA or plasmid as the quantitation standard.

In some embodiments, the first AAV vector is administered at least 1, 2, 3, 4, or 5 times.

In some embodiments, the second AAV vector is administered at least 1, 2, 3, 4, or 5 times.

In some embodiments, the effective amount of the AAV dual vector system is between about $1\times10^{10}$-$1\times10^{13}$ vector genomes (vg), about $1\times10^{11}$-$1\times10^{13}$ vg, $1\times10^{12}$-$1\times10^{13}$ vg.

In some embodiments, the AAV dual vector system is administered at least 1, 2, 3, 4, or 5 times.

In some embodiments, the effective amount of the composition is between about $1\times10^{10}$-$1\times10^{13}$ vector genomes (vg), about $1\times10^{11}$-$1\times10^{13}$ vg, $1\times10^{12}$-$1\times10^{13}$ vg.

In some embodiments, the composition is administered at least 1, 2, 3, 4, or 5 times.

Disclosed herein is a recombinant polynucleotide encoding a human dysferlin (hDYSF) protein, wherein the recombinant polynucleotide sequence comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20. In some embodiments, the recombinant polynucleotide sequence comprising a nucleotide sequence of SEQ ID NO: 20.

Disclosed herein is a method of making the recombinant polynucleotide encoding a human dysferlin (hDYSF) protein, wherein the recombinant polynucleotide sequence comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20, in which the method comprises contacting a cell with the recombinant polynucleotide comprising a first polynucleotide sequence encoding an N-terminal of a human dysferlin (hDYSF) protein, wherein the first polynucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) a second recombinant polynucleotide comprising a second polynucleotide sequence encoding a C-terminal fragment of a human dysferlin protein, wherein the second polynucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

Disclosed herein is a method of making the recombinant polynucleotide encoding a human dysferlin (hDYSF) protein, wherein the recombinant polynucleotide comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20, in which the method comprises contacting a cell with the dual AAV vector system comprising: (I) a first AAV vector, wherein the first AAV vector comprises (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (c) a second ITR, wherein the polynucleotide is flanked by the first and second ITRs; and (II) a second AAV vector, wherein the second AAV vector comprises (a) a third inverted terminal repeat (ITR); (b) a polynucleotide encoding a fragment of a human dysferlin protein, wherein the polynucleotide sequence consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide of (v) across the full length of the nucleotide sequence of (v); and (c) a fourth ITR, wherein the polynucleotide is flanked by the third and fourth ITRs.

In some embodiments, the cell is a eukaryotic cell. In some embodiments, the cell is a muscle cell, a heart cell, a stem cell, a satellite cell, and/or a liver cell.

Disclosed herein is a method of making the recombinant polynucleotide encoding a human dysferlin (hDYSF) protein, wherein the recombinant polynucleotide sequence comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20, in which the method comprises administering to a subject with the recombinant polynucleotide comprising a first polynucleotide sequence encoding an N-terminal of a human dysferlin (hDYSF) protein, wherein the first polynucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) a second recombinant polynucleotide comprising a second polynucleotide sequence encoding a C-terminal fragment of a human dysferlin protein, wherein the second polynucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

Disclosed herein is a method of making the recombinant polynucleotide encoding a human dysferlin (hDYSF) protein, wherein the recombinant polynucleotide comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20, in which the method comprises administering to a subject with the dual AAV vector system comprising: (I) a first AAV vector, wherein the first AAV vector comprises (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (c) a second ITR, wherein the polynucleotide is flanked by the first and second ITRs; and (II) a second AAV vector, wherein the second AAV vector comprises (a) a third inverted terminal repeat (ITR); (b) a polynucleotide encoding a fragment of a human dysferlin protein, wherein the polynucleotide consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide sequence of (v) across the full length of the nucleotide sequence of (v); and (c) a fourth ITR, wherein the polynucleotide is flanked by the third and fourth ITRs.

Disclosed herein is a method of treating muscular dystrophy of a subject, comprising expression of the recombinant polynucleotide encoding a human dysferlin (hDYSF) protein, wherein the recombinant polynucleotide sequence comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20 in the subject.

In some embodiments, the method comprises administering to a subject with the recombinant polynucleotide comprising a first polynucleotide sequence encoding an N-terminal of a human dysferlin (hDYSF) protein, wherein the first polynucleotide sequence consists of: (i) the nucleotide sequence of SEQ ID NO: 1, 6, or 18; (ii) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (b) a second recombinant polynucleotide comprising a second polynucleotide sequence encoding a C-terminal fragment of a human dysferlin protein, wherein the second polynucleotide sequence consists of: (i) the nucleotide sequence of SEQ ID NO: 2, 8, or 19; (ii) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (v) a polynucleotide sequence encoding the fragment of the hDYSF protein, wherein the fragment of the hDYSF protein consists of the amino acid sequence of SEQ ID NO: 10; or (vi) a polynucleotide sequence that is at least 90%, 91%, 92%, 93%, 94%, 95%, 96%, 97%, 98%, or 99% identical to the polynucleotide sequence of (v) across the full length of the nucleotide sequence of (v).

In some embodiments, the method comprises administering to a subject with the dual AAV vector system comprising: (I) a first AAV vector, wherein the first AAV vector comprises (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 1 or 6; (ii) a nucleotide sequence that is at least 90%, 91%, 92%, 93%, 94%, 95%, 96%, 97%, 98%, or 99% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 90%, 91%, 92%, 93%, 94%, 95%, 96%, 97%, 98%, or 99% identical to the nucleotide sequence of SEQ ID NO: 13 or 15 across the full length of SEQ ID NO: 13 or 15; (v) a nucleotide sequence encoding the fragment of the hDYSF protein, wherein the fragment of the hDYSF protein consists of the amino acid sequence of SEQ ID NO: 9; or (vi) a nucleotide sequence that is at least 90%, 91%, 92%, 93%, 94%, 95%, 96%, 97%, 98%, or 99% identical to the nucleotide sequence of (v) across the full length of the nucleotide sequence of (v); and (c) a second ITR, wherein the polynucleotide is flanked by the first and second ITRs; and (II) a second AAV vector, wherein the second AAV vector comprises (a) a third inverted terminal repeat (ITR); (b) a polynucleotide encoding a fragment of a human dysferlin protein, wherein the polynucleotide consists of: (i) the nucleotide sequence of SEQ ID NO: 2 or 8; (ii) a nucleotide sequence that is at least 90%, 91%, 92%, 93%, 94%, 95%, 96%, 97%, 98%, or 99% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 90%, 91%, 92%, 93%, 94%, 95%, 96%, 97%, 98%, or 99% identical to the nucleotide sequence of SEQ ID NO: 14 or 16 across the full length of SEQ ID NO: 14 or 16; (v) a polynucleotide encoding the fragment of the hDYSF protein, wherein the fragment of the hDYSF protein consists of the amino acid sequence of SEQ ID NO: 10; or (vi) a polynucleotide that is at least 90%, 91%, 92%, 93%, 94%, 95%, 96%, 97%, 98%, or 99% identical to the polynucleotide sequence of (v) across the full length of the nucleotide sequence of (v); and (c) a fourth ITR, wherein the polynucleotide is flanked by the third and fourth ITRs.

In some embodiments, the subject is a mammal selected from human, a non-human primate, a canine, an ovine, a horse, a porcine, a murine, a rat, a rabbit, a bovine, or a feline.

In some embodiments, the subject suffers from dysferlinopathy. In some embodiments, dysferlinopathy is limb girdle muscular dystrophy type 2B (LGMD2B) or Miyoshi myopathy.

BRIEF DESCRIPTION OF THE DRAWINGS

(FIG. 4B: immune staining, FIG. 4D: western blot). 3222 is the full-length control.

FIG. 5A demonstrates full-length dysferlin expression by dysferlin immunolabeling (top panels) seen following delivery of dual vectors to left tibialis anterior (LTA). Dysferlin expression persisted through 1, 3, and 6 months post-treatment with no aberrant response in pathology (H&E, lower panels). Scale bar, 100 μm. N=4 per timepoint. FIG. 5B shows western blot for 1, 3, 6 month samples demonstrating expression of full-length dysferlin in injected LTAs (2 per group). γ-tubulin used as loading control. FIG. 5C shows a biodistribution plot of vector genomes per μg genomic DNA at 3 and 6 months post-injection for various tissues. Note: the LTA was treated; logarithmic axis.

FIG. 7A shows dysferlin immunolabeling of tissues after systemic delivery of $6\times10^{12}$vg (2.4e13 vg/kg, based on a supercoiled DNA or plasmid as the quantitation standard) AAVrh.74.MHCK7.DYSF.DV (n=6 per dose). Muscles shown are heart, gastrocnemius, diaphragm and quadriceps for Dysf–/–, treated (AAV.DV) and wild-type (WT) tissues. FIG. 7B shows quantification of centralized nuclei in the tibialis anterior (LTA), gastrocnemius (RGAS), quadriceps (LQD), triceps (RTri) and diaphragm. *$p<0.05$ significant difference between sample and wild-type, #no significant difference between sample and wildtype. FIG. 7C shows a western blot of tissue lysates (H: heart, G: gastrocnemius, Q: quadriceps, D: diaphragm) demonstrating full length dysferlin band at 237 kD, Y-tubulin included as a loading control.

FIG. 10A: Diaphragm muscle strips were harvested and subjected to a protocol to assess specific force. Treated diaphragms demonstrated significant improvement in force (P>0.01, ANOVA) which was not different from wild-type force at both doses [2e12 vg total AAV.DYSF DV (8e13 vg/kg, based on a supercoiled DNA or plasmid as the quantitation standard), or 6e12 vg total AAV.DYSF.DV (2.4e13 vg/kg, based on a supercoiled DNA or plasmid as the quantitation standard)]. FIG. 10B** shows there was a dose dependent response in membrane resealing. There was no significant improvement at low dose.

FIG. 12A shows histology (H&E) and dysferlin immunofluorescence (IF) images of NHP tissue at 3 and 6 months post-injection of either AAV5.DYSF or AAVrh.74.DYSF.DV. H&E stained sections show lack of immune infiltration and necrosis of fibers. IF sections show overexpression of dysferlin in injected tissues as compared to native (sham). FIG. 12B shows western blot image of tissues from 3 and 6 months post-injection for both AAV5.DYSF and AAVrh.74.DYSF.DV. Importantly, injected tissues demonstrate an overexpression of dysferlin as compared to sham control. Positive (+) control is wild-type mouse tissue and the negative (−) control is 129-Dysf−/− uninjected tissue. FIG. 12C shows biodistribution of vector genomes following IM injection with AAVrh.74.DYSF.DV into the left TA, note logarithmic scale.

DETAILED DESCRIPTION

Definitions

Figure 1:
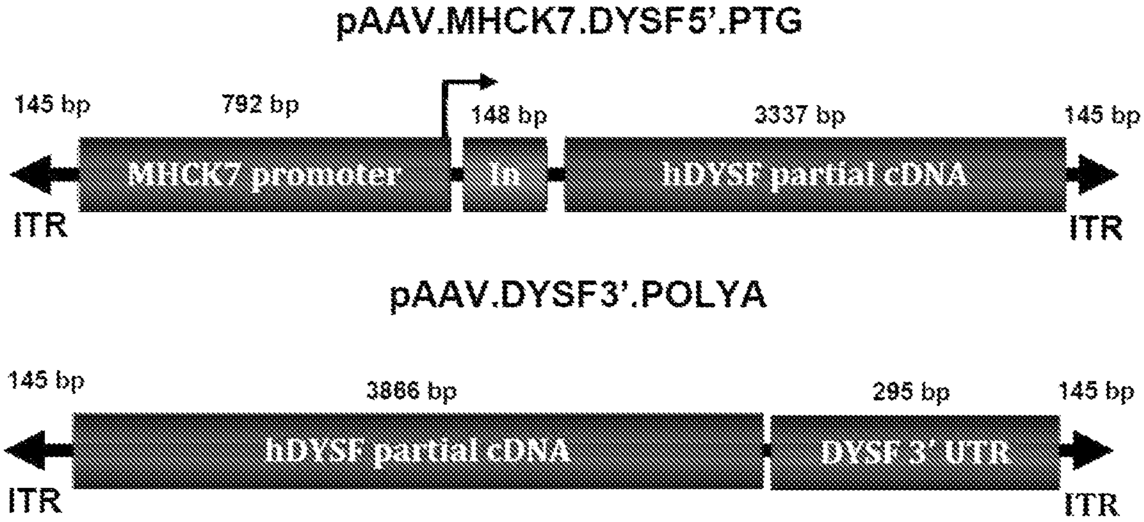
FIG. 1 provides the schematic of the dual AAV vector system for treating dysferlinopathies. The 5' vector (e.g., 5' hDYSF AAV vector), pAAV.MHCK7.DYSF5'.PTG (PTG=promoter/transgene) contains the muscle specific MHCK7 promoter, chimeric intron, consensus Kozak sequence and 5'portion of the DYSF cDNA corresponding to amino acids 1-1113 of SEQ ID NO: 12. The 3' vector (e.g., 3' hDYSF AAV vector), pAAV.DYSF3'.POLYA, contains a 3'portion of the DYSF cDNA corresponding to amino acids 794-2080 of SEQ ID NO: 12 and DYSF 3'UTR harboring a polyadenylation signal.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2% and such ranges are included. It is to be understood, although not always explicitly stated, that all numerical designations are preceded by the term "about". It also is to be understood, although not always explicitly stated, that the reagents described herein are merely exemplary and that equivalents of such are known in the art.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2$^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used herein, the terms "increased", "decreased", "high", "low" or any grammatical variation thereof refer to a variation of about 90%, 80%, 50%, 20%, 10%, 5%, 1%, 0.5%, or even 0.1% of the reference composition, polypeptide, protein, etc.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal sequence identity while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity across the length of the reference sequence and exhibits substantially equivalent biological activity to the reference protein, polypeptide or nucleic acid. Alternatively, when referring to polynucleotides, an equivalent thereof is in one aspect, a polynucleotide that hybridizes under stringent conditions to the reference polynucleotide or its complement that in a further aspect, has the same or similar activity or function as the reference polynucleotide or its complement An equivalent of a protein or a polypeptide (referred to herein as the reference) shares at least 50% (or at least 60%, or at least 70%, or at least 80%, or at least 90%) identity to the reference and retains the reference's function and manufacturability.

As used herein, the terms "function," "activity," and "enzymatic activity" are used interchangeably. Loss of dysferlin has been shown to compromise Ca2+-dependent membrane repair in skeletal muscle (Song et al., *Proc. Natl. Acad. Sci. USA* 98:4084-4088, 2001 and Schnepp et al., *J. Virol.* 77:3495-3504, 2003). In addition, dysferlin has been shown to interact with other proteins involved in membrane repair, including annexins A1 and A2, AHNAK, and caveolin-3 (Schnepp et al., *J. Virol.* 77:3495-3504, 2003, Duan et al., *J. Virol.* 72:8568-8577, 1998, Donsante et al., Gene Ther. 8:1343-1346, 2001, and Monahan et al., *Expert Opin. Drug. Saf.* 1:79-91, 2002). The loss of muscle fiber regenerative capacity is thought to be a contributory consequence of dysferlin deficiency (Song et al., *Gene Ther.* 8:1299-1306, 2001). Dysferlin has also been associated with vesicle trafficking and endocytosis and T tubule formation (Eveson et al., *The Journal of Biological Chemistry* 285:28529-28539, 2010, Klinge et al., *FASEB Journal: Official Publication of the Federation of American Societies for Experimental Biology* 21:1768-1776, 2007, and Klinge et al., *Muscle & Nerve* 41:166-173, 2010). Accordingly, examples of activities of dysferlin include, but are not limited to, membrane repair in skeletal muscle, such as membrane resealing, prevention or restoration of muscle fiber regenerative capacity, vesicle trafficking, endocytosis, and transverse (T-) tubule formation. Membrane repair assays, vesicle trafficking assays, and tube formation assays are known in the art and can be used to measure dysferlin activity in vitro. See, e.g., Carmeille et al., *Methods Mol. Biol.* 1668:195-207, 2017, Vassilieva and Nusrat, *Methods Mol. Biol.* 440:3-14, 2008, Demonbreun et al., *Am. J. Pathol.* 184(1):248-59, 2014, each of which are incorporated by reference in their entireties. Additional methods for measuring the activity of dysferlin is found, for example, in Grose et al., *PLOS One* 7:e39233, 2012 and Sondergaard et al., *Anns of Clin. Trans. Neurol.* 2:256-270, 2015.

An equivalent of a polynucleotide (referred to herein as the reference) shares at least 50% (or at least 60%, or at least 70%, or at least 80%, or at least 90%) identity to the reference, and encodes the same polypeptide as the one encoded by the reference, or encodes an equivalent of the polypeptide encoded by the reference.

To arrive at a position or a consecutive segment of a test sequence equivalent to (or corresponding to) an/a amino acid/nucleotide residue or a consecutive segment of a reference sequence, a sequence alignment is performed between the test and reference sequences. The positions or segments aligned to each other are determined as equivalents.

The term "affinity tag" refers to a polypeptide that may be included within a fusion protein to allow detection of the fusion protein and/or purification of the fusion protein from the cellular milieu using a ligand that is able to bind to, i.e., has affinity for, the affinity tag. The ligand may be, but is not limited to, an antibody, a resin, or a complementary polypeptide. An affinity tag may comprise a small peptide, commonly a peptide of approximately 4 to 16 amino acids in length, or it may comprise a larger polypeptide. Commonly used affinity tags include polyarginine, FLAG, V5, polyhistidine, c-Myc, Strep II, maltose binding protein (MBP), N-utilization substance protein A (NusA), thioredoxin (Trx), and glutathione S-transferase (GST), among others (for examples, see GST Gene Fusion System Handbook-Sigma-Aldrich). In an embodiment the affinity tag is a polyhistidine tag, for example a His6 tag (SEQ ID NO: 21). The inclusion of an affinity tag in a fusion protein allows the fusion protein to be purified from the cellular milieu by affinity purification, using an affinity medium that is able to tightly and specifically bind the affinity tag. The affinity medium may comprise, for example, a metal-charged resin or a ligand covalently linked to a stationary phase (matrix) such as agarose or metal beads. For example, polyhistidine tagged fusion proteins (also referred to as His tagged fusion proteins) can be recovered by immobilized metal ion chromatography using $Ni^{2+}$ or $Co^{2+}$ loaded resins, anti-FLAG affinity gels may be used to capture FLAG tagged fusion proteins, and glutathione cross-linked to a solid support such as agarose may be used to capture GST tagged fusion proteins. In one aspect, an affinity tag is a purification tag or marker.

As used herein the terms "purification", "purifying", or "separating" refer to the process of isolating one or more biomaterials (e.g., polynucleotides, polypeptides, or viral vectors) from a complex mixture, such as a cell lysate or a mixture of polypeptides. The purification, separation, or isolation need not be complete, i.e., some components of the complex mixture may remain with the one or more biomaterials (e.g., polynucleotides, polypeptides, or viral vectors) after the purification process. However, the product of purification should be enriched for the one or more biomaterials (e.g., polynucleotides, polypeptides, or viral vectors) relative to the complex mixture before purification and a significant portion of the other components initially present within the complex mixture should be removed by the purification process.

The term "cell" as used herein may refer to either a prokaryotic or eukaryotic cell, optionally obtained from a subject or a commercially available source. In some instances, the cell is a host cell, for example, a mammalian cell or a mammalian host cell. In some instances, the host cell is also referred to herein as a production cell or a packaging cell. In some cases, the cell line is a packaging cell line.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human, e.g., HEK293 cells, Chinese Hamster Ovary (CHO) cells, CHO-S cells, CHO-K1 cells, 293T cells, HeLa cells, Baby hamster kidney (BHK) cells, Sf9 cells, stem cells, satellite cells, and muscle cells. Examples of muscle cells include, but are not limited to, skeletal muscle cells, cardiac muscle cells, and smooth muscle cells.

"Prokaryotic cells" that usually lack a nucleus or any other membrane-bound organelles and are divided into two domains, bacteria and archaea. In addition to chromosomal DNA, these cells can also contain genetic information in a circular loop called an episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality (for example, having a similar function or activity). It should be understood, without being explicitly stated that when referring to an equivalent or biological equivalent to a reference polypeptide, protein, or polynucleotide, that an equivalent or biological equivalent has the recited structural relationship to the reference polypeptide, protein, or polynucleotide and equivalent or substantially equivalent biological activity. For example, non-limiting examples of equivalent polypeptides, proteins, or polynucleotides include a polypeptide, protein or polynucleotide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide, polynucleotide or protein sequences across the length of the reference polypeptide, polynucleotide, or protein. Alternatively, an equivalent polypeptide is one that is encoded by a polynucleotide or its complement that hybridizes under conditions of high stringency to a polynucleotide encoding such reference polypeptide sequences and that have substantially equivalent or equivalent biological activity. Conditions of high stringency are described herein and incorporated herein by reference. Alternatively, an equivalent thereof is a polypeptide encoded by a polynucleotide or a complement thereto, having at least 70%, or alternatively at least 75%, or alternatively 80%, or alternatively at least 85%, or alternatively at least 90%, or alternatively at least 95% identity, or at least 97% sequence identity across the length of the reference polynucleotide to the reference polynucleotide, e.g., the wild-type polynucleotide. Such equivalent polypeptides have the same biological activity as the polypeptide encoded by the reference polynucleotide.

Non-limiting examples of equivalent polynucleotides, include a polynucleotide having at least 60%, or alternatively at least 65%, or alternatively at least 70%, or alternatively at least 75%, or alternatively 80%, or alternatively at least 85%, or alternatively at least 90%, or alternatively at least 95%, or alternatively at least 97%, identity to a reference polynucleotide. An equivalent also intends a polynucleotide or its complement that hybridizes under conditions of high stringency to a reference polynucleotide. Such equivalent polynucleotides have the same biological activity as the reference polynucleotide.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences across the length of the reference polynucleotide. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can be determined by incorporating them into clustalW (available at the web address: genome.jp/tools/clustalw/, last accessed on Jan. 13, 2017) or Clustal Omega (available at ebi.ac.uk/Tools/msa/clustalo/).

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

As used herein, the term "at least 90% identical" refers to an identity of two compared sequences (polynucleotides or polypeptides) of about 90% to about 100%. It also include an identity of at least at least 91%, at least 92%, at least 93%, at least 94%, at least 95%, at least 96%, at least 97%, at least 98%, at least 99%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

As used herein, the terms "retain" "similar" and "same" are used interchangeably while describing a function, an activity or an functional activity of a polynucleotide, a protein and/or a peptide, referring to a functional activity of at least about 20% (including but not limited to: at least about 30%, at least about 40%, at least about 50%, at least about 60%, at least about 70%, at least about 80%, at least about 90%, at least about 95%, at least about 97%, or about 100%) of the activity of the reference protein, polynucleotide and/or peptide.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. In one aspect, an equivalent polynucleotide is one that hybridizes under stringent conditions to a reference polynucleotide or its complement. In another aspect, an equivalent polypeptide is a polypeptide that is encoded by a polynucleotide is one that hybridizes under stringent conditions to a reference polynucleotide or its complement.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

As used herein, the term "functional" may be used to modify any molecule, biological, or cellular material to intend that it accomplishes a particular, specified effect.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, complementary DNA (cDNA), DNA-RNA hybrids, or a polymer comprising purine and pyrimidine bases or other natural, chemically or biochemically modified, non-natural, or derivatized nucleotide bases. In certain embodiments, the polynucleotide comprises and/or encodes a messenger RNA (mRNA), a short hairpin RNA, and/or small hairpin RNA. In one embodiment, the polynucleotide is or encodes an mRNA. In certain embodiments, the polynucleotide is a double-strand (ds) DNA, such as an engineered ds DNA or a ds cDNA synthesized from a single-stranded RNA.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, a consecutive amino acid sequence refers to a sequence having at least two amino acids. However, it is noted that a consecutive amino acid sequence of a first part and a second part does not limit the amino acid sequence to have the first part directly conjugated to the second part. It is also possible that the first part is linked to the second part via a third part, such as a link, thus forming one consecutive amino acid sequence.

As used herein, the terms "conjugate," "conjugated," "conjugating," and "conjugation" refer to the formation of a bond between molecules, and in particular between two amino acid sequences and/or two polypeptides. Conjugation can be direct (i.e. a bond) or indirect (i.e. via a further molecule). The conjugation can be covalent or non-covalent.

As used herein a consecutive amino acid sequence may comprise two or more polypeptides conjugated with each other directly or indirectly (for example via a linker).

As used herein, the term "recombinant expression system" refers to a genetic construct or constructs for the expression of certain genetic material formed by recombination.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; lipid nanoparticles; polypeptides; polysaccharides; lipopolysaccharides; artificial viral envelopes; metal particles; and bacteria, or viruses, such as rabies virus, flavivirus, lentivirus, baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer" "mRNA-based delivery", "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes, including for example protamine complexes, lipid nanoparticles, polymeric nanoparticles, lipid-polymer hybrid nanoparticles, and inorganic nanoparticles, or combinations thereof) as well as techniques facilitating the delivery of "naked" polynucleotides (such as electroporation, "gene gun" delivery and various other techniques used for the introduction of polynucleotides). The introduced polynucleotide can be unmodified or can comprise one or more modifications; for example, a modified mRNA may comprise ARCA capping; enzymatic polyadenylation to add a tail of 100-250 adenosine residues (SEQ ID NO: 22); and substitution of one or both of cytidine with 5-methylcytidine and/or uridine with pseudouridine. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

As used herein, the term "viral capsid" or "capsid" refers to the proteinaceous shell or coat of a viral particle. Capsids function to encapsidate, protect, transport, and release into host cell a viral genome. Capsids are generally comprised of oligomeric structural subunits of protein ("capsid proteins"). As used herein, the term "encapsidated" means enclosed within a viral capsid.

As used herein, the term "helper" in reference to a virus or plasmid refers to a virus or plasmid used to provide the additional components necessary for replication and packaging of a viral particle or recombinant viral particle, such as the modified AAV disclosed herein. The components encoded by a helper virus may include any genes required for virion assembly, encapsidation, genome replication, and/or packaging. For example, the helper virus may encode necessary enzymes for the replication of the viral genome. Non-limiting examples of helper viruses and plasmids suitable for use with AAV constructs include pHELP (plasmid), adenovirus (virus), or herpesvirus (virus).

As used herein, a biological sample, or a sample, can be obtained from a subject, cell line or cultured cell or tissue. Exemplary samples include, but are not limited to, cell sample, tissue sample, liquid samples such as blood and other liquid samples of biological origin (including, but not limited to, ocular fluids (aqueous and vitreous humor), peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose6 phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$, $^{89}Zr$ or $^{125}I$.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly (NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, an epitope tag is a biological structure or sequence, such as a protein or carbohydrate, which acts as an antigen that is recognized by an antibody. In certain embodiments, an epitope tag is used interchangeably with a purification marker and/or an affinity tag.

A "composition" is intended to mean a combination of two or more compounds, such as a combination of an active polypeptide, polynucleotide, viral vector, or antibody and another compound or composition, inert (e.g., a detectable label) or active (e.g., a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, non-human primates, murines, rats, rabbit, simians, bovines, ovine, porcine, canines, feline, farm animals, sport animals, pets, equine, and primates, particularly human. Besides being useful for human treatment, the present invention is also useful for veterinary treatment of companion mammals, exotic animals and domesticated animals, including mammals, rodents, and the like. In one embodiment, the mammals include horses, dogs, and cats. In another embodiment of the present invention, the human is an adolescent or infant under the age of eighteen years of age.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. In one aspect, the term "treatment" excludes prevention or prophylaxis.

The term "suffering" as it related to the term "treatment" refers to a patient or individual who has been diagnosed with or is predisposed to a disease.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. In one aspect, an effective amount is a therapeutically effective amount. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to inhibit RNA virus replication ex vivo, in vitro or in vivo.

The term administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, *Handbook of Parvoviruses* 1:169-228, 1989, and Berns, *Virology* 1743-1764, 1999. However, it is fully expected that these same principles will be applicable to additional AAV serotypes since it is well known that the various serotypes are quite closely related, both structurally and functionally, even at the genetic level. (See, for example, Blacklowe, *Parvoviruses and Human Disease* 165-174, 1988, J. R. Pattison, ed.; and Rose, *Comprehensive Virology* 3:1-61, 1974). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV expression cassette" as used herein refers to a nucleotide sequence comprising one or more polynucleotides of interest (or transgenes) that are flanked by AAV terminal repeat sequences (ITRs). Such AAV expression cassette can be replicated and packaged into infectious viral particles (e.g., AAV vectors) when present in a host cell that has been transfected with a vector encoding and expressing rep and cap gene products.

An "AAV virion" or "AAV vector" or "AAV viral particle" or "AAV vector particle" refers to a viral particle composed of at least one AAV capsid protein and an encapsidated polynucleotide AAV expression cassette. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV expression cassette, as such a plasmid is contained within an AAV vector particle.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., *J Virol,* 45:555-564 (1983) as corrected by Ruffing et al., *J Gen Virol,* 75:3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.,* 78:6381-6388 (2004); the AAV-10 genome is provided in *Mol. Ther.,* 13(1): 67-76 (2006); and the AAV-11 genome is provided in *Virology,* 330(2): 375-383 (2004). Cloning of the AAVrh.74 serotype is described in Rodino-Klapac., et al. *Journal of translational medicine* 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97-129 (1992).

Recombinant AAV genomes of the disclosure comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAVrh.74, AAVrh.10, AAVrh.20, AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., *Molecular Therapy,* 22(11): 1900-1909 (2014). As noted in the Background section above, the nucleotide sequences of the genomes of various AAV serotypes are known in the art. In some embodiments, to promote skeletal muscle specific expression, AAV1, AAV6, AAV8 or AAVrh.74 is used.

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "recombinant" as used herein with respect to polypeptides or polynucleotides, such as DNA or RNA, refers to molecules formed by laboratory methods of recombination, such as molecular cloning. Molecular cloning techniques are known in the art and may include, but is not limited to, PCR amplification of a polynucleotide, enzymatic digestion of a polynucleotide, ligation of a polynucleotide into an expression cassette (e.g., mammalian expression cassette), transformation, transfection or transduction of a cell with the polynucleotide, and expression of the polynucleotide to produce the polypeptide. See e.g., Green and Sambrook, Molecular Cloning: A Laboratory Manual, 2012. The term "recombinant polynucleotide" is meant to include fragments of protein-encoding polynucleotides. For instance, a recombinant polynucleotide may include a fragment of the polynucleotide that encodes for a human dysferlin protein. A recombinant polynucleotide may be produced by PCR amplification of a fragment of a protein-encoding polynucleotide. A recombinant polypeptide may be produced by expression of one or more recombinant polynucleotides.

Disclosed herein are polynucleotides encoding fragments of a human dysferlin (hDSYSF) protein. Further disclosed herein are plasmids, viral vectors, vector systems, viral packaging systems, cells, and compositions comprising polynucleotides encoding fragments of a human dysferlin (hDSYSF) protein. Also disclosed herein are methods of making and using such polynucleotides, plasmids, viral vectors, vector systems, viral packaging systems, cells, and compositions.

Disclosed herein is a recombinant polynucleotide encoding a fragment of a human dysferlin (hDYSF) protein, wherein the recombinant polynucleotide comprises a first nucleotide sequence, wherein the first nucleotide sequence consists of: (a) the nucleotide sequence of SEQ ID NO: 1, 6, or 18; (b) a nucleotide sequence that is at least 90%, 91%, 92%, 93%, 94%, 95%, 96%, 97%, 98%, or 99% identical to the nucleotide sequence of SEQ ID NO: 1, SEQ ID NO: 6, or SEQ ID NO: 18 across its respective full length of SEQ ID NO: 1, 6, or 18; (c) the nucleotide sequence of SEQ ID NO: 13 or 15; (d) a nucleotide sequence that is at least 90%, 91%, 92%, 93%, 94%, 95%, 96%, 97%, 98%, or 99% identical to the nucleotide sequence of SEQ ID NO: 13 or 15 across its respective full length of SEQ ID NO: 13 or 15; (e) a nucleotide sequence encoding the hDYSF protein, wherein the hDYSF protein consists of the amino acid sequence of SEQ ID NO: 9; or (f) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of (e) across the full length of the nucleotide sequence of (e).

Further disclosed herein is a recombinant polynucleotide sequence encoding a fragment of a human dysferlin protein, wherein the recombinant polynucleotide comprises a first nucleotide sequence, wherein the first nucleotide sequence consists of: (a) the nucleotide sequence of SEQ ID NO: 2, 8, or 19; (b) a nucleotide sequence that is at least 90%, 91%, 92%, 93%, 94%, 95%, 96%, 97%, 98%, or 99% identical to the nucleotide sequence of SEQ ID NO: 2, 8 or 19 across its respective full length of SEQ ID NO: 2, 8 or 19; (c) the nucleotide sequence of SEQ ID NO: 14 or 16; (d) a nucleotide sequence that is at least 90%, 91%, 92%, 93%, 94%, 95%, 96%, 97%, 98%, or 99% identical to the nucleotide sequence of SEQ ID NO: 14 or 16 across its respective full length of SEQ ID NO: 14 or 16; (e) a polynucleotide sequence encoding the hDYSF protein, wherein the hDYSF protein consists of the amino acid sequence of SEQ ID NO: 10; or (f) a polynucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the polynucleotide sequence of (e) across the full length of the nucleotide sequence of (e).

Further disclosed herein are adeno-associated viral (AAV) vectors. In some embodiments, an adeno-associated viral (AAV) vector comprises: (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 1 or 6; (ii) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 1 or 6 across the full length of SEQ ID NO: 1 or 6; (iii) the nucleotide sequence of SEQ ID NO: 13 or 15; (iv) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 13 or 15 across the full length of SEQ ID NO: 13 or 15; (v) a nucleotide sequence encoding the hDYSF protein, wherein the hDYSF protein consists of the amino acid sequence of SEQ ID NO: 9; or (vi) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of (v) across the full length of the nucleotide sequence of (v); and (c) a second ITR, wherein the polynucleotide is flanked by the first and second ITRs.

In some embodiments, an adeno-associated viral (AAV) vector comprises: (a) a first inverted terminal repeat (ITR); (b) a polynucleotide encoding a fragment of a human dysferlin (hDYSF) protein, wherein the polynucleotide consists of: (i) the nucleotide sequence of SEQ ID NO: 2 or 8; (ii) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 2 or 8 across the full length of SEQ ID NO: 2 or 8; (iii) the nucleotide sequence of SEQ ID NO: 14 or 16; (iv) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 14 or 16 across the full length of SEQ ID NO: 14 or 16; (v) a nucleotide sequence encoding the hDYSF protein, wherein the hDYSF protein consists of the amino acid sequence of SEQ ID NO: 10; or (vi) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of (v) across the full length of the nucleotide sequence of (v); and (c) a second ITR, wherein the polynucleotide is flanked by the first and second ITRs.

Further disclosed herein are adeno-associated viral (AAV) expression cassettes. In some embodiments, the AAV expression cassette comprises: (a) a first inverted terminal repeat (ITR), wherein the first ITR comprises any of the ITRs disclosed herein; (b) any of the 5' hDYSF polynucleotides disclosed herein; and (c) a second ITR, wherein the second ITR comprises any of the ITRs disclosed herein, wherein the 5' hYDSYF polynucleotide of (b) is flanked by the first and second ITRs of (a) and (c).

In some embodiments, the AAV expression cassette comprises: (a) a first inverted terminal repeat (ITR), wherein the first ITR comprises any of the ITRs disclosed herein; (b) any of the 3' hDYSF polynucleotides disclosed herein; and (c) a second ITR, wherein the second ITR comprises any of the ITRs disclosed herein, wherein the 3' hYDSYF polynucleotide of (b) is flanked by the first and second ITRs of (a) and (c).

Further disclosed herein are adeno-associated viral (AAV) vectors. In some embodiments, the AAV vector comprises: (a) a first inverted terminal repeat (ITR), wherein the first ITR comprises any of the ITRs disclosed herein; (b) any of the 5' hDYSF polynucleotides disclosed herein; and (c) a second ITR, wherein the second ITR comprises any of the ITRs disclosed herein, wherein the 5' hYDSYF polynucleotide of (b) is flanked by the first and second ITRs of (a) and (c).

In some embodiments, the AAV vector comprises: (a) a first inverted terminal repeat (ITR), wherein the first ITR comprises any of the ITRs disclosed herein; (b) any of the 3' hDYSF polynucleotides disclosed herein; and (c) a second ITR, wherein the second ITR comprises any of the ITRs disclosed herein, wherein the 3' hYDSYF polynucleotide of (b) is flanked by the first and second ITRs of (a) and (c).

Further disclosed herein are dual adeno-associated viral (AAV) vector systems. In some embodiments, the dual AAV vector system comprises: (a) a first AAV vector, wherein the first AAV vector comprises any of the 5' hDYSF polynucleotides disclosed herein; and (b) a second AAV vector, wherein the second AAV vector comprises any of the 3' hDYSF polynucleotides disclosed herein.

Further disclosed herein are dual adeno-associated viral (AAV) vector systems. In some embodiments, the dual AAV vector system comprises, consists of, or consists essentially of: (a) a first AAV vector, wherein the first AAV vector comprises, consists of, or consists essentially of any of the 5' hDYSF AAV vectors disclosed herein; and (b) a second AAV vector, wherein the second AAV vector comprises, consists of, or consists essentially of any of the 3' hDYSF AAV vectors disclosed herein.

Further disclosed herein are adeno-associated viral (AAV) vectors. In some embodiments, the AAV vectors comprise any of the 5' hDYSF polynucleotides disclosed herein.

In some embodiments, the AAV vectors comprise any of the 3' hDYSF polynucleotides disclosed herein.

In some embodiments, the polynucleotides, plasmids, viral vectors (e.g., viruses or viral particles), vector systems, viral packaging systems, cells, and compositions further comprise one or more nucleotide sequences comprising, consisting of, or consisting essentially of an inverted terminal repeat (ITR), promoter, intron, selection marker, or origin of replication (ORI).

In some embodiments, the polynucleotides, plasmids, viral vectors, vector systems, viral packaging systems, cells, and compositions further comprise one or more additional nucleotide sequences comprising an inverted terminal repeat (ITR), selection marker, origin of replication (ORI), untranslated region (UTR), or polyadenylation (polyA) signal.

Further disclosed herein are methods of treating a dysferlinopathy. In some embodiments, a method of treating a dysferlinopathy comprises administering to a subject in need thereof any of polynucleotides, plasmids, viral vectors, vector systems, viral packaging systems, cells, and compositions disclosed herein.

Further disclosed herein are uses of any of the polynucleotides, plasmids, viral vectors, vector systems, viral packaging systems, cells, and compositions disclosed herein in the manufacture of a medicament for the treatment of a dysferlinopathy.

Homologous Recombination and hDYSF Fragments

AAV-mediated gene therapy presents a desirable treatment strategy for multiple diseases; however, it is hindered by the restrictive 4.7 kb packaging limit of the AAV virion. Of particular interest are diseases with no current cure or effective therapy, such as dysferlinopathies. Disclosed herein is a method of making or producing a full length of dysferlin gene by homologous recombination of two partially genomes. In one example, the two partially packaged genomes is shown in FIG. 1, as pAAV.MHCK7.DYSF5'.PTG and pAAV.DYSF3'.POLYA. Once the two genomes, whether through viral delivery by being packaged into AAV vector or non-viral methods (e.g., LNP), are delivered to a cell (e.g., myocytes), they generate a transcript comprising the full length dysferlin coding region, leading to expression of a functional dysferlin protein. The overlap region between the two polynucleotides facilitates the homologous recombination that leads to the transcript containing the full-length dysferlin gene. By separating the full length dysferlin gene to two partially packaged genomes, this method successfully bypasses the AAV packaging limitation and produce a functional, full-length dysferlin gene. In one embodiment, the transcript is an expression cassette comprising the sequence that is at least 90%, 91%, 92%, 93%, 94%, 95%, 96%, 97%, 98%, or 99% identical to the nucleotide sequence of SEQ ID NO: 20. In one embodiment, the transcript is an expression cassette comprising the sequence of SEQ ID NO: 20.

In some embodiments, disclosed herein is a recombinant polynucleotide encoding a human dysferlin (hDYSF) protein, wherein the recombinant polynucleotide sequence comprising a nucleotide sequence of SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20. In some instances, the recombinant polynucleotide comprising a nucleotide sequence of SEQ ID NO: 20. In some instances, disclosed herein is a method of making the recombinant polypeptide. In some cases, the method comprises contacting a cell with the recombinant polynucleotide encoding a 5' fragment of the hDYSF protein and a second recombinant polynucleotide encoding a 3' fragment of the hDYSF protein. In some cases, the method comprises contacting a cell with a dual AAV vector system described herein. In some cases, the cell is a eukaryotic cell, optionally a muscle cell, a heart cell, and/or a liver cell. In some cases, the method comprises administering to a subject with the recombinant polynucleotide encoding a 5' fragment of the hDYSF protein and a second recombinant polynucleotide encoding a 3' fragment of the hDYSF protein. In some cases, the method comprises administering to a subject a dual AAV vector system described herein. In some cases, the method comprises treating muscular dystrophy of a subject, by expressing the recombinant polynucleotide comprising SEQ ID NO: 20 or a nucleotide sequence that is at least 90%, 91%, 92%, 93%, 94%, 95%, 96%, 97%, 98%, or 99% identical to the nucleotide sequence of SEQ ID NO: 20. In some cases, the subject suffers from dysferlinopathy, optionally selected from LGMD2B or Miyoshi myopathy.

Also disclosed herein are two recombinant polynucleotides, each encoding a fragment of human dysferlin (hDYSF) protein, that can lead to the production of the full length dysferlin gene by homologous recombination as described above. In some embodiments, a recombinant polynucleotide encodes a 5' fragment of the hDYSF protein. In some embodiments, the recombinant polynucleotide encoding the 5' fragment of the hDYSF protein is referred to as the 5' hDYSF polynucleotide. In some embodiments, a recombinant polynucleotide encodes a 3' fragment of the hDYSF protein. In some embodiments, the recombinant polynucleotide encoding the 3' fragment of the hDYSF protein is referred to as the 3' hDSYF polynucleotide.

5' hDYSF Polynucleotide

In some embodiments, the 5' hDYSF polynucleotide comprises, consists of, or consists essentially of between 3330-3365, 3330-3360, 3330-3355, 3335-3365, 3335-3350, 3340-3365, 3340-3360, or 3340-3355 consecutive nucleotides of a region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide comprises, consists of, or consists essentially of 3360, 3359, 3358, 3357, 3356, 3355, 3354, 3353, 3352, 3351, 3350, 3349, 3348, 3347, 3346, 3345, 3344, 3343, 3342, 3341, or 3340 or fewer consecutive nucleotides of a region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of between 3330-3365, 3330-3360, 3330-3355, 3335-3365, 3335-3350, 3340-3365, 3340-3360, or 3340-3355 consecutive nucleotides of a region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11, wherein the 5' hDYSF polynucleotide is at least 80%, 82%, 85%, 87%, 88%, 90%, 92%, 95%, 96%, 97%, 98%, 99%, or 100% to the nucleotide sequence of SEQ ID NO: 11 across the full length of the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide comprises, consists of, or consists essentially of 3360, 3359, 3358, 3357, 3356, 3355, 3354, 3353, 3352, 3351, 3350, 3349, 3348, 3347, 3346, 3345, 3344, 3343, 3342, 3341, or 3340 or fewer consecutive nucleotides of a region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11, wherein the 5' hDYSF polynucleotide is at least 80%, 82%, 85%, 87%, 88%, 90%, 92%, 95%, 96%, 97%, 98%, 99%, or 100% to the nucleotide sequence of SEQ ID NO: 11 across the full length of the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide is at least 85% to the nucleotide sequence of SEQ ID NO: 11 across the full length of the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide is at least 90% to the nucleotide sequence of SEQ ID NO: 11 across the full length of the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide is at least 95% to the nucleotide sequence of SEQ ID NO: 11 across the full length of the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of between 3330-3365, 3330-3360, 3330-3355, 3335-3365, 3335-3350, 3340-3365, 3340-3360, or 3340-3355 consecutive nucleotides of a region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11, wherein the 5' hDYSF polynucleotide comprises 30, 25, 20, 19, 18, 17, 16, 15, 14, 13, 12, 11, 10, 9, 8, 7, 6, 5, 4, 3, 2, 1 or fewer nucleotide mismatches in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' hDYSF polynucleotide comprises, consists of, or consists essentially of 3360, 3359, 3358, 3357, 3356, 3355, 3354, 3353, 3352, 3351, 3350, 3349, 3348, 3347, 3346, 3345, 3344, 3343, 3342, 3341, or 3340 or fewer consecutive nucleotides of a region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11, wherein the 5' hDYSF polynucleotide comprises 30, 25, 20, 19, 18, 17, 16, 15, 14, 13, 12, 11, 10, 9, 8, 7, 6, 5, 4, 3, 2, 1 or fewer nucleotide mismatches in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' polynucleotide comprises 15 or fewer nucleotide mismatches in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' polynucleotide comprises 10 or fewer nucleotide mismatches in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' polynucleotide comprises 5 or fewer nucleotide mismatches in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' polynucleotide comprises 1 nucleotide mismatch in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' polynucleotide comprises at least 1 nucleotide mismatch in the region between nucleotides 100-4000, 100-3900, 100-3800, 100-3750, 100-3716, 150-4000, 150-3900, 150-3800, 150-3750, 150-3716, 200-4000, 200-3900, 200-3800, 200-3750, 200-3716, 250-4000, 250-3900, 250-3800, 250-3750, 250-3716, 300-4000, 300-3900, 300-3800, 300-3750, 300-3716, 350-4000, 350-3900, 350-3800, 350-3750, 350-3716, 370-4000, 370-3900, 370-3800, 370-3750, 370-3716, 377-4000, 377-3900, 377-3800, 377-3750, or 377-3716 of SEQ ID NO: 11. In some embodiments, the 5' polynucleotide comprises at least 1 nucleotide mismatch in the region between nucleotides 377-3716 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of 3330-3365, 3330-3360, 3330-3355, 3335-3365, 3335-3350, 3340-3365, 3340-3360, or 3340-3355 consecutive nucleotides of SEQ ID NO: 11, wherein the 5' hDSYF polynucleotide comprises a region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide comprises, consists of, or consists essentially of 3360, 3359, 3358, 3357, 3356, 3355, 3354, 3353, 3352, 3351, 3350, 3349, 3348, 3347, 3346, 3345, 3344, 3343, 3342, 3341, or 3340 or fewer consecutive nucleotides of SEQ ID NO: 11, wherein the 5' hDSYF polynucleotide comprises a region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide comprises a nucleotide sequence that is at least 85%, 87%, 88%, 90%, 92%, 95%, 96%, 97%, 98%, 99%, or 100% identical to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11 across the full length of the region. In some embodiments, the 5' hDYSF polynucleotide comprises a nucleotide sequence that is at least 90% identical to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11 across the full length of the region. In some embodiments, the 5' hDYSF polynucleotide comprises a nucleotide sequence that is at least 95% identical to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11 across the full length of the region. In some embodiments, the 5' hDYSF polynucleotide comprises a nucleotide sequence that is at least 99% identical to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11 across the full length of the region. In some embodiments, the 5' hDYSF polynucleotide does not further comprise a second polynucleotide sequence encoding a second fragment of the hDYSF protein.

In some embodiments, the 5' hDYSF polynucleotide comprises 10, 9, 8, 7, 6, 5, 4, 3, 2, 1 or fewer nucleotide mismatches to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide comprises 5 or fewer nucleotide mismatches to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide comprises 2 or fewer nucleotide mismatches to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide comprises 1 or fewer nucleotide mismatches to the nucleotide sequence of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of 3360, 3359, 3358, 3357, 3356, 3355, 3354, 3353, 3352, 3351, 3350, 3349, 3348, 3347, 3346, 3345, 3344, 3343, 3342, 3341, or 3340 or fewer consecutive nucleotides of SEQ ID NO: 11, wherein the 5' hDSYF polynucleotide comprises a region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11, wherein the 5' hDYSF polynucleotide is at least 90%, 92%, 95%, 96%, 97%, 98%, 99%, or 100% to the nucleotide sequence of SEQ ID NO: 11 across the full length of the region comprising nucleotide positions 3400-3716, 3400-3700, 3400-3650, 3400-3600, 3400-3550, 3400-3500, 3390-3716, 3390-3700, 3390-3650, 3390-3600, 3390-3550, 3390-3500, 3380-3716, 3380-3700, 3380-3650, 3380-3500, 3371-3716, 3371-3700, 3371-3650, 3371-3600, 3371-3550, or 3371-3500 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of between 3330-3365, 3330-3360, 3330-3355, 3335-3365, 3335-3350, 3340-3365, 3340-3360, or 3340-3355 consecutive nucleotides of SEQ ID NO: 11, wherein the 5' hDSYF polynucleotide does not comprise a region consisting of nucleotide positions 1-100, 1-200, 1-300, 1-350, 1-375, 1-376, 100-200, 100-300, 100-350, 100-375, 100-376, 200-300, 200-350, 200-375, or 200-376 of SEQ ID NO: 11. In some embodiments, the 5' hDSYF polynucleotide does not comprise a region consisting of nucleotide positions 1-376 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of 3360, 3359, 3358, 3357, 3356, 3355, 3354, 3353, 3352, 3351, 3350, 3349, 3348, 3347, 3346, 3345, 3344, 3343, 3342, 3341, or 3340 or fewer consecutive nucleotides of SEQ ID NO: 11, wherein the 5' hDSYF polynucleotide does not comprise a region consisting of nucleotide positions 1-100, 1-200, 1-300, 1-350, 1-375, 100-200, 100-300, 100-350, 100-375, 200-300, 200-350, 200-375 of SEQ ID NO: 11. In some embodiments, the 5' hDSYF polynucleotide does not comprise a region consisting of nucleotide positions 1-376 of SEQ ID NO: 11. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of a nucleotide sequence of SEQ ID NO: 1. In some embodiments, the 5' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of SEQ ID NO: 1 across the full length of SEQ ID NO: 1. In some embodiments, the 5' hDYSF polynucleotide comprises, consists of, or consists essentially of a nucleotide sequence that is at least 90% identical to the nucleotide sequence of SEQ ID NO: 1 across the full length of SEQ ID NO: 1. In some embodiments, the 5' hDYSF polynucleotide comprises, consists of, or consists essentially of a nucleotide sequence that is at least 92% identical to the nucleotide sequence of SEQ ID NO: 1 across the full length of SEQ ID NO: 1. In some embodiments, the 5' hDYSF polynucleotide comprises, consists of, or consists essentially of a nucleotide sequence that is at least 95% identical to the nucleotide sequence of SEQ ID NO: 1 across the full length of SEQ ID NO: 1. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of a nucleotide sequence of SEQ ID NO: 13. In some embodiments, the 5' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of SEQ ID NO: 13 across the full length of SEQ ID NO: 13. In some embodiments, the 5' hDYSF polynucleotide comprises, consists of, or consists essentially of a nucleotide sequence that is at least 90% identical to the nucleotide sequence of SEQ ID NO: 13 across the full length of SEQ ID NO: 13. In some embodiments, the 5' hDYSF polynucleotide comprises, consists of, or consists essentially of a nucleotide sequence that is at least 92% identical to the nucleotide sequence of SEQ ID NO: 13 across the full length of SEQ ID NO: 13. In some embodiments, the 5' hDYSF polynucleotide comprises, consists of, or consists essentially of a nucleotide sequence that is at least 95% identical to the nucleotide sequence of SEQ ID NO: 13 across the full length of SEQ ID NO: 13. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of a nucleotide sequence encoding a fragment of an hDYSF protein comprising the N-terminal region of a wild-type hDSYF protein. In some embodiments, the fragment of the hDYSF protein comprising the N-terminal region of a wild-type hDSYF protein is referred to as an N-terminal hDYSF protein. In some embodiments, the 5' hDYSF polynucleotide comprises, consists of, or consists essentially of a nucleotide sequence encoding the N-terminal hDYSF protein, wherein the N-terminal hDYSF protein comprises a region comprising, consisting of, or consisting essentially of amino acid residues 1-1113, 200-1113, 400-1113, 500-1113, 600-1113, 650-113, 650-1100, 700-1100, 700-1113, 700-1050, 700-1000, 800-1113, 800-1100, 800-1050, 900-1113, 900-1100, 1000-1113, or 1000-1100 of SEQ ID NO: 12. In some embodiments, the 5' hDYSF polynucleotide comprises, consists of, or consists essentially of nucleotide sequence that is at least 80%, 82%, 85%, 88%, 89%, 90%, 91%, 92%, 93%, 94%, 95%, 96%, 97%, 98%, or 99% identical to the nucleotide sequence of encoding an N-terminal hDYSF protein across the full length of the nucleotide sequence encoding the N-terminal hDYSF protein, wherein the N-terminal hDYSF protein comprises a region comprising, consisting of, or consisting essentially of amino acid residues 1-1113, 200-1113, 400-1113, 500-1113, 600-1113, 650-113, 650-1100, 700-1100, 700-1113, 700-1050, 700-1000, 800-1113, 800-1100, 800-1050, 900-1113, 900-1100, 1000-1113, or 1000-1100 of SEQ ID NO: 12. In some embodiments, the N-terminal hDYSF protein comprises a region comprising, consisting of, or consisting essentially of amino acid residues 999-1113, 999-1100, 1000-1113, or 1000-1100. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of a nucleotide sequence encoding the N-terminal hDYSF protein, wherein the N-terminal hDYSF protein is at least 1000 amino acids in length, and wherein the N-terminal hDYSF protein comprises a region comprising amino acid residues 999-1113, 999-1100, 1000-1113, or 1000-1100 of SEQ ID NO: 12. In some embodiments, the 5' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of encoding an N-terminal hDYSF protein across the full length of the nucleotide sequence encoding the N-terminal hDYSF protein, wherein the N-terminal hDYSF protein is at least 1000 amino acids in length, and wherein the N-terminal hDYSF protein comprises a region comprising amino acid residues 999-1113, 999-1100, 1000-1113, or 1000-1100 of SEQ ID NO: 12. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of a nucleotide sequence encoding the N-terminal hDYSF protein, wherein the N-terminal hDYSF protein comprises, consists of, or consists essentially of the amino acid sequence of SEQ ID NO: 9. In some embodiments, the 5' hDYSF polynucleotide does not further comprise a second polynucleotide sequence encoding a second fragment of the hDYSF protein.

In some embodiments, the 5' hDYSF polynucleotide comprises, consists of, or consists essentially of nucleotide sequence that is at least 80%, 82%, 85%, 88%, 89%, 90%, 91%, 92%, 93%, 94%, 95%, 96%, 97%, 98%, or 99% identical to the nucleotide sequence of encoding an N-terminal hDYSF protein across the full length of the nucleotide sequence encoding the N-terminal hDYSF protein, wherein the N-terminal hDYSF protein comprises, consists of, or consists essentially of the amino acid sequence of SEQ ID NO: 9. In some embodiments, the 5' hDYSF polynucleotide comprises, consists of, or consists essentially of nucleotide sequence that is at least 90% identical to the nucleotide sequence of encoding an N-terminal hDYSF protein across the full length of the nucleotide sequence encoding the N-terminal hDYSF protein, wherein the N-terminal hDYSF protein comprises, consists of, or consists essentially of the amino acid sequence of SEQ ID NO: 9. In some embodiments, the 5' hDYSF polynucleotide comprises, consists of, or consists essentially of nucleotide sequence that is at least 92% identical to the nucleotide sequence of encoding an N-terminal hDYSF protein across the full length of the nucleotide sequence encoding the N-terminal hDYSF protein, wherein the N-terminal hDYSF protein comprises, consists of, or consists essentially of the amino acid sequence of SEQ ID NO: 9. In some embodiments, the 5' hDYSF polynucleotide comprises, consists of, or consists essentially of nucleotide sequence that is at least 95% identical to the nucleotide sequence of encoding an N-terminal hDYSF protein across the full length of the nucleotide sequence encoding the N-terminal hDYSF protein, wherein the N-terminal hDYSF protein comprises, consists of, or consists essentially of the amino acid sequence of SEQ ID NO: 9. In some embodiments, the 5' hDYSF polynucleotide comprises, consists of, or consists essentially of nucleotide sequence that is at least 97% identical to the nucleotide sequence of encoding an N-terminal hDYSF protein across the full length of the nucleotide sequence encoding the N-terminal hDYSF protein, wherein the N-terminal hDYSF protein comprises, consists of, or consists essentially of the amino acid sequence of SEQ ID NO: 9. In some embodiments, the N-terminal hDYSF protein comprises an amino acid sequence that is at least 80%, 82%, 85%, 88%, 89%, 90%, 91%, 92%, 93%, 94%, 95%, 96%, 97%, 98%, or 99% identical to the amino acid sequence of SEQ ID NO: 9 across the full length of SEQ ID NO: 9. In some embodiments, the N-terminal hDYSF protein comprises an amino acid sequence that is at least 90% identical to the amino acid sequence of SEQ ID NO: 9 across the full length of SEQ ID NO: 9. In some embodiments, the N-terminal hDYSF protein comprises an amino acid sequence that is at least 92% identical to the amino acid sequence of SEQ ID NO: 9 across the full length of SEQ ID NO: 9. In some embodiments, the N-terminal hDYSF protein comprises an amino acid sequence that is at least 95% identical to the amino acid sequence of SEQ ID NO: 9 across the full length of SEQ ID NO: 9. In some embodiments, the N-terminal hDYSF protein comprises an amino acid sequence that is at least 97% identical to the amino acid sequence of SEQ ID NO: 9 across the full length of SEQ ID NO: 9. In some embodiments, the 5' hDYSF polynucleotide does not further comprise a second polynucleotide sequence encoding a second fragment of the hDYSF protein.

In some embodiments, the 5' hDYSF polynucleotide comprises the nucleotide sequence of SEQ ID NO: 6. In some embodiments, the 5' hDYSF polynucleotide comprises a nucleotide sequence that is at least 80%, 81%, 82%, 83%, 84%, 85%, 87%, 88%, 89%, 90%, 91%, 92%, 93%, 94%, 95%, 96%, 97%, 98%, 99%, or 100% identical to the nucleotide sequence of SEQ ID NO: 6 across the full length of SEQ ID NO: 6. In some embodiments, the 5' hDYSF polynucleotide comprises a nucleotide sequence that is at least 85% identical to the nucleotide sequence of SEQ ID NO: 6 across the full length of SEQ ID NO: 6. In some embodiments, the 5' hDYSF polynucleotide comprises a nucleotide sequence that is at least 90% identical to the nucleotide sequence of SEQ ID NO: 6 across the full length of SEQ ID NO: 6. In some embodiments, the 5' hDYSF polynucleotide does not further comprise a second polynucleotide sequence encoding a second fragment of the hDYSF protein.

In some embodiments, the 5' hDYSF polynucleotide comprises the nucleotide sequence of SEQ ID NO: 15. In some embodiments, the 5' hDYSF polynucleotide comprises a nucleotide sequence that is at least 80%, 81%, 82%, 83%, 84%, 85%, 87%, 88%, 89%, 90%, 91%, 92%, 93%, 94%, 95%, 96%, 97%, 98%, 99%, or 100% identical to the nucleotide sequence of SEQ ID NO: 6 across the full length of SEQ ID NO: 15. In some embodiments, the 5' hDYSF polynucleotide comprises a nucleotide sequence that is at least 85% identical to the nucleotide sequence of SEQ ID NO: 15 across the full length of SEQ ID NO: 15. In some embodiments, the 5' hDYSF polynucleotide comprises a nucleotide sequence that is at least 90% identical to the nucleotide sequence of SEQ ID NO: 15 across the full length of SEQ ID NO: 15. In some embodiments, the 5' hDYSF polynucleotide does not further comprise a second polynucleotide sequence encoding a second fragment of the hDYSF protein.

3' hDYSF Polynucleotide

In some embodiments, the 3' hDYSF polynucleotide comprises, consists of, or consists essentially of between 3500-4100, 3500-4000, 3500-3900, 3500-3880, 3500-3870, 3600-4100, 3600-4000, 3600-3900, 3600-3880, 3600-3870, 3700-4100, 3700-4000, 3700-3900, 3700-3880, 3700-3870, 3800-4100, 3800-4000, or 3800-3900 consecutive nucleotides of a region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide comprises, consists of, or consists essentially of 4100, 4000, 3900, 3880, or 3870 or fewer consecutive nucleotides of a region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of between 3500-4100, 3500-4000, 3500-3900, 3500-3880, 3500-3870, 3600-4100, 3600-4000, 3600-3900, 3600-3880, 3600-3870, 3700-4100, 3700-4000, 3700-3900, 3700-3880, 3700-3870, 3800-4100, 3800-4000, or 3800-3900 consecutive nucleotides of a region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11, wherein the 3' hDYSF polynucleotide is at least 80%, 82%, 85%, 87%, 88%, 90%, 92%, 95%, 96%, 97%, 98%, 99%, or 100% to the nucleotide sequence of SEQ ID NO: 11 across the full length of the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide comprises, consists of, or consists essentially of 4100, 4000, 3900, 3880, or 3870 or fewer consecutive nucleotides of a region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11, wherein the 3' hDYSF polynucleotide is at least 80%, 82%, 85%, 87%, 88%, 90%, 92%, 95%, 96%, 97%, 98%, 99%, or 100% to the nucleotide sequence of SEQ ID NO: 11 across the full length of the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide is at least 85% to the nucleotide sequence of SEQ ID NO: 11 across the full length of the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide is at least 90% to the nucleotide sequence of SEQ ID NO: 11 across the full length of the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide is at least 95% to the nucleotide sequence of SEQ ID NO: 11 across the full length of the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of between 3500-4100, 3500-4000, 3500-3900, 3500-3880, 3500-3870, 3600-4100, 3600-4000, 3600-3900, 3600-3880, 3600-3870, 3700-4100, 3700-4000, 3700-3900, 3700-3880, 3700-3870, 3800-4100, 3800-4000, or 3800-3900 consecutive nucleotides of a region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-

6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11, wherein the 3' hDYSF polynucleotide comprises 30, 25, 20, 19, 18, 17, 16, 15, 14, 13, 12, 11, 10, 9, 8, 7, 6, 5, 4, 3, 2, 1 or fewer nucleotide mismatches in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 3' hDYSF polynucleotide comprises, consists of, or consists essentially of 4100, 4000, 3900, 3880, or 3870 or fewer consecutive nucleotides of a region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11, wherein the 3' hDYSF polynucleotide comprises 30, 25, 20, 19, 18, 17, 16, 15, 14, 13, 12, 11, 10, 9, 8, 7, 6, 5, 4, 3, 2, 1 or fewer nucleotide mismatches in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 5' polynucleotide comprises 15 or fewer nucleotide mismatches in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 5' polynucleotide comprises 10 or fewer nucleotide mismatches in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 5' polynucleotide comprises 5 or fewer nucleotide mismatches in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 5' polynucleotide comprises 1 nucleotide mismatch in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 5' polynucleotide comprises at least 1 nucleotide mismatch in the region between nucleotides 2600-6850, 2600-6800, 2600-6780, 2600-6750, 2600-6725, 2600-6700, 2700-6850, 2700-6800, 2700-6780, 2700-6750, 2700-6725, 2700-6700, 2700-6680, 2700-6650, 2700-6625, 2700-6620, 2700-6619, 2750-6850, 2750-6800, 2750-6780, 2750-6750, 2750-6725, 2750-6700, 2750-6680, 2750-6650, 2750-6625, 2750-6620, 2750-6619, 2754-6850, 2754-6800, 2754-6780, 2754-6750, 2754-6725, 2754-6700, 2754-6680, 2754-6650, 2754-6625, 2754-6620, or 2754-6619 of SEQ ID NO: 11. In some embodiments, the 5' polynucleotide comprises at least 1 nucleotide mismatch in the region between nucleotides 2754-6619 of SEQ ID NO: 11. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of between 3500-4100, 3500-4000, 3500-3900, 3500-3880, 3500-3870, 3600-4100, 3600-4000, 3600-3900, 3600-3880, 3600-3870, 3700-4100, 3700-4000, 3700-3900, 3700-3880, 3700-3870, 3800-4100, 3800-4000, or 3800-3900 consecutive nucleotides of SEQ ID NO: 11, wherein the 5' hDSYF polynucleotide does not comprise a region consisting of nucleotide positions 6620-6914, 6620-6900, 6620-6800, 6620-6700, 6700-6914, 6700-6800, 6800-6914, or 6800-6900 of SEQ ID NO: 11. In some embodiments, the 3' hDSYF polynucleotide does not comprise a region consisting of nucleotide positions 6620-6914 of SEQ ID NO: 11. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of 4100, 4000, 3900, 3880, or 3870 or fewer consecutive nucleotides of SEQ ID NO: 11, wherein the 3' hDSYF polynucleotide does not comprise a region consisting of nucleotide positions 6620-6914, 6620-6900, 6620-6800, 6620-6700, 6700-6914, 6700-6800, 6800-6914, or 6800-6900 of SEQ ID NO: 11. In some embodiments, the 3' hDSYF polynucleotide does not comprise a region consisting of nucleotide positions 6620-6914 of SEQ ID NO: 11. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence of SEQ ID NO: 2. In some embodiments, the 3' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of SEQ ID NO: 2 across the full length of SEQ ID NO: 2. In some embodiments, the 3' hDYSF polynucleotide comprises, consists of, or consists essentially of a nucleotide sequence that is at least 90% identical to the nucleotide sequence of SEQ ID NO: 2 across the full length of SEQ ID NO: 2. In some embodiments, the 3' hDYSF polynucleotide comprises, consists of, or consists essentially of a nucleotide sequence that is at least 92% identical to the nucleotide sequence of SEQ ID NO: 2 across the full length of SEQ ID NO: 2. In some embodiments, the 3' hDYSF polynucleotide comprises, consists of, or consists essentially of a nucleotide sequence that is at least 95% identical to the nucleotide sequence of SEQ ID NO: 2 across the full length of SEQ ID NO: 2. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence of SEQ ID NO: 14. In some embodiments, the 3' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of SEQ ID NO: 14 across the full length of SEQ ID NO: 14. In some embodiments, the 3' hDYSF polynucleotide comprises, consists of, or consists essentially of a nucleotide sequence that is at least 90% identical to the nucleotide sequence of SEQ ID NO: 14 across the full length of SEQ ID NO: 14. In some embodiments, the 3' hDYSF polynucleotide comprises, consists of, or consists essentially of a nucleotide sequence that is at least 92% identical to the nucleotide sequence of SEQ ID NO: 14 across the full length of SEQ ID NO: 14. In some embodiments, the 3' hDYSF polynucleotide comprises, consists of, or consists essentially of a nucleotide sequence that is at least 95% identical to the nucleotide sequence of SEQ ID NO: 14 across the full length of SEQ ID NO: 14. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence encoding a fragment of an hDYSF protein comprising the C-terminal region of a wild-type hDSYF protein. In some embodiments, the fragment of the hDYSF protein comprising the C-terminal region of a wild-type hDSYF protein is referred to as a C-terminal hDYSF protein. In some embodiments, the 3' hDYSF polynucleotide comprises, consists of, or consists essentially of a nucleotide sequence encoding the C-terminal hDYSF protein, wherein the C-terminal hDYSF protein comprises a region comprising, consisting of, or consisting essentially of amino acid residues 750-2080, 750-2000, 750-1900, 775-2080, 775-2000, 775-1900, 794-2080, 794-2000, or 794-1900 of SEQ ID NO: 12. In some embodiments, the 3' hDYSF polynucleotide comprises, consists of, or consists essentially of nucleotide sequence that is at least 80%, 82%, 85%, 88%, 89%, 90%, 91%, 92%, 93%, 94%, 95%, 96%, 97%, 98%, or 99% identical to the nucleotide sequence of encoding a C-terminal hDYSF protein across the full length of the nucleotide sequence encoding the C-terminal hDYSF protein, wherein the C-terminal hDYSF protein comprises a region comprising, consisting of, or consisting essentially of amino acid residues 750-2080, 750-2000, 750-1900, 775-2080, 775-2000, 775-1900, 794-2080, 794-2000, or 794-1900 of SEQ ID NO: 12. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence encoding the C-terminal hDYSF protein, wherein the C-terminal hDYSF protein comprises, consists of, or consists essentially of 1400, 1350, 1325, 1300, 1290, or 1287 or fewer amino acids in length, and wherein the C-terminal hDYSF protein comprises a region comprising amino acid residues 750-2080, 750-2000, 750-1900, 775-2080, 775-2000, 775-1900, 794-2080, 794-2000, or 794-1900 of SEQ ID NO: 12. In some embodiments, the 3' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of encoding a C-terminal hDYSF protein across the full length of the nucleotide sequence encoding the C-terminal hDYSF protein, wherein the C-terminal hDYSF protein is 1400, 1350, 1325, 1300, 1290, or 1287 or fewer amino acids in length, and wherein the C-terminal hDYSF protein comprises a region comprising amino acid residues 750-2080, 750-2000, 750-1900, 775-2080, 775-2000, 775-1900, 794-2080, 794-2000, or 794-1900 of SEQ ID NO: 12. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence encoding the C-terminal hDYSF protein, wherein the C-terminal hDYSF protein comprises, consists of, or consists essentially of 1400, 1350, 1325, 1300, 1290, or 1287 or fewer amino acids in length, wherein the C-terminal hDYSF protein does not comprise a region comprising amino acid residues 678-793, 678-750, 678-725, or 678-700 of SEQ ID NO: 12. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence encoding the C-terminal hDYSF protein, wherein the C-terminal hDYSF protein comprises, consists of, or consists essentially of the amino acid sequence of SEQ ID NO: 10. In some embodiments, the 3' hDYSF polynucleotide does not further comprise a second polynucleotide sequence encoding a second fragment of the hDYSF protein.

In some embodiments, the 3' hDYSF polynucleotide comprises, consists of, or consists essentially of a nucleotide sequence that is at least 80%, 82%, 85%, 88%, 89%, 90%, 91%, 92%, 93%, 94%, 95%, 96%, 97%, 98%, or 99% identical to the nucleotide sequence of encoding a C-terminal hDYSF protein across the full length of the nucleotide sequence encoding the C-terminal hDYSF protein, wherein the C-terminal hDYSF protein comprises, consists of, or consists essentially of the amino acid sequence of SEQ ID NO: 10. In some embodiments, the 3' hDYSF polynucleotide comprises, consists of, or consists essentially of nucleotide sequence that is at least 90% identical to the nucleotide sequence of encoding a C-terminal hDYSF protein across the full length of the nucleotide sequence encoding the C-terminal hDYSF protein, wherein the C-terminal hDYSF protein comprises, consists of, or consists essentially of the amino acid sequence of SEQ ID NO: 10. In some embodiments, the 3' hDYSF polynucleotide comprises, consists of, or consists essentially of nucleotide sequence that is at least 92% identical to the nucleotide sequence of encoding a C-terminal hDYSF protein across the full length of the nucleotide sequence encoding the C-terminal hDYSF protein, wherein the C-terminal hDYSF protein comprises, consists of, or consists essentially of the amino acid sequence of SEQ ID NO: 10. In some embodiments, the 3' hDYSF polynucleotide comprises, consists of, or consists essentially of nucleotide sequence that is at least 95% identical to the nucleotide sequence of encoding a C-terminal hDYSF protein across the full length of the nucleotide sequence encoding the C-terminal hDYSF protein, wherein the C-terminal hDYSF protein comprises, consists of, or consists essentially of the amino acid sequence of SEQ ID NO: 10. In some embodiments, the 3' hDYSF polynucleotide comprises, consists of, or consists essentially of nucleotide sequence that is at least 97% identical to the nucleotide sequence of encoding a C-terminal hDYSF protein across the full length of the nucleotide sequence encoding the C-terminal hDYSF protein, wherein the C-terminal hDYSF protein comprises, consists of, or consists essentially of the amino acid sequence of SEQ ID NO: 10. In some embodiments, the C-terminal hDYSF protein comprises an amino acid sequence that is at least 80%, 82%, 85%, 88%, 89%, 90%, 91%, 92%, 93%, 94%, 95%, 96%, 97%, 98%, or 99% identical to the amino acid sequence of SEQ ID NO: 10 across the full length of SEQ ID NO: 10. In some embodiments, the C-terminal hDYSF protein comprises an amino acid sequence that is at least 90% identical to the amino acid sequence of SEQ ID NO: 10 across the full length of SEQ ID NO: 10. In some embodiments, the C-terminal hDYSF protein comprises an amino acid sequence that is at least 92% identical to the amino acid sequence of SEQ ID NO: 10 across the full length of SEQ ID NO: 10. In some embodiments, the C-terminal hDYSF protein comprises an amino acid sequence that is at least 95% identical to the amino acid sequence of SEQ ID NO: 10 across the full length of SEQ ID NO: 10. In some embodiments, the C-terminal hDYSF protein comprises an amino acid sequence that is at least 97% identical to the amino acid sequence of SEQ ID NO: 10 across the full length of SEQ ID NO: 10. In some embodiments, the 3' hDYSF polynucleotide does not further comprise a second polynucleotide sequence encoding a second fragment of the hDYSF protein.

In some embodiments, the 3' hDYSF polynucleotide comprises the nucleotide sequence of SEQ ID NO: 8. In some embodiments, the 3' hDYSF polynucleotide comprises a nucleotide sequence that is at least 80%, 81%, 82%, 83%, 84%, 85%, 87%, 88%, 89%, 90%, 91%, 92%, 93%, 94%, 95%, 96%, 97%, 98%, 99%, or 100% identical to the nucleotide sequence of SEQ ID NO: 8 across the full length of SEQ ID NO: 8. In some embodiments, the 3' hDYSF polynucleotide comprises a nucleotide sequence that is at least 85% identical to the nucleotide sequence of SEQ ID NO: 8 across the full length of SEQ ID NO: 8. In some embodiments, the 3' hDYSF polynucleotide comprises a nucleotide sequence that is at least 90% identical to the nucleotide sequence of SEQ ID NO: 8 across the full length of SEQ ID NO: 8. In some embodiments, the 3' hDYSF polynucleotide does not further comprise a second polynucleotide sequence encoding a second fragment of the hDYSF protein.

In some embodiments, the 3' hDYSF polynucleotide comprises the nucleotide sequence of SEQ ID NO: 16. In some embodiments, the 3' hDYSF polynucleotide comprises a nucleotide sequence that is at least 80%, 81%, 82%, 83%, 84%, 85%, 87%, 88%, 89%, 90%, 91%, 92%, 93%, 94%, 95%, 96%, 97%, 98%, 99%, or 100% identical to the nucleotide sequence of SEQ ID NO: 16 across the full length of SEQ ID NO: 16. In some embodiments, the 3' hDYSF polynucleotide comprises a nucleotide sequence that is at least 85% identical to the nucleotide sequence of SEQ ID NO: 16 across the full length of SEQ ID NO: 16. In some embodiments, the 3' hDYSF polynucleotide comprises a nucleotide sequence that is at least 90% identical to the nucleotide sequence of SEQ ID NO: 16 across the full length of SEQ ID NO: 16. In some embodiments, the 3' hDYSF polynucleotide does not further comprise a second polynucleotide sequence encoding a second fragment of the hDYSF protein.

In some embodiments, the sequences of the 5' hDSYF polynucleotide and the 3' hDYSF polynucleotide comprise an overlap of at least 500, 600, 700, 800, 900, 950, 960, or 963 nucleotides. In some embodiments, the sequences of the N-terminal hDSYF protein and of the C-terminal hDSYF protein comprise an overlap of at least 50, 100, 150, 200, 250, 300, or 320 amino acids.

Inverted Terminal Repeats

In some embodiments, the polynucleotides, plasmids, viral vectors, vector systems, viral packaging systems, cells, and compositions further comprise a nucleotide sequence comprising, consisting of, or consisting essentially of one or more inverted terminal repeats (ITRS). In some embodiments, the polynucleotides, plasmids, viral vectors, vector systems, viral packaging systems, cells, and compositions further comprise two, three, four, five, or six or more nucleotide sequences comprising, consisting of, or consisting essentially of two, three, four, five, or six or more ITRs. In some embodiments, the two or more ITRs are the same. In some embodiments, the two or more ITRs are different.

In some embodiments, the recombinant polynucleotide is flanked by the two or more ITRs. In some embodiments, the 5' hDYSF polynucleotide is flanked by a first pair of ITRs. In some embodiments, the 3' hDYSF polynucleotide is flanked by a second pair of ITRs. In some embodiments, the ITRs in the first pair of ITRs are the same. In some embodiments, the ITRs in the first pair of ITRs are different. In some embodiments, the ITRs in the second pair of ITRs are the same. In some embodiments, the ITRs in the second pair of ITRs are different. In some embodiments, the ITRs in the first pair of ITRs are the same as the ITRs in the second pair of ITRs. In some embodiments, at least one ITR in the first pair of ITRs is the same as at least one ITR in the second pair of ITRs. In some embodiments, the ITRs in the first pair of ITRs are different from the ITRs in the second pair of ITRs. In some embodiments, at least one ITR in the first pair of ITRs is different from at least one ITR in the second pair of ITRs.

In some embodiments, the ITR is a viral ITR. In some embodiments, the ITR is an AAV ITR. In some embodiments, the AAV ITR is selected from an ITR from at least one of AAV serotypes AAVrh.20, AAV-1, AAV-2, AAV-3, AAV-4, AAV-5, AAV-6, AAV-7, AAVrh.74, AAV-8, AAV-9, AAV-10, AAVrh.10, AAV-11, AAV-12 and AAV-13. In some embodiments, the AAV ITR is an AAV2 ITR. In some embodiments, the AAV ITR is an AAV5 ITR. The ITR sequences for AAV1-6 can be found, for example, in Grimm et al., J. Virol. 80(1):426-39, 2006, which is incorporated by reference in its entirety.

In some embodiments, the recombinant polynucleotide does not comprise an AAV sequence other than an inverted terminal repeat (ITR).

In some embodiments, the recombinant polynucleotide does not comprise a viral sequence other than an inverted terminal repeat (ITR).

In some embodiments, the ITR comprises the nucleotide sequence of SEQ ID NO: 3. In some embodiments, the ITR comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence of SEQ ID NO: 3 across the full length of SEQ ID NO: 3. In some embodiments, the ITR comprises the nucleotide sequence of SEQ ID NO: 3. In some embodiments, the ITR comprises a nucleotide sequence that is at least 90% identical to the nucleotide sequence of SEQ ID NO: 3 across the full length of SEQ ID NO: 3. In some embodiments, the ITR comprises a nucleotide sequence that is at least 95% identical to the nucleotide sequence of SEQ ID NO: 3 across the full length of SEQ ID NO: 3. In some embodiments, the ITR comprises a nucleotide sequence comprising 10, 9, 8, 7, 6, 5, 4, 3, 2, or 1 or fewer nucleotide mismatches to the nucleotide sequence of SEQ ID NO: 3. In some embodiments, the ITR comprises a nucleotide sequence comprising 5 or fewer nucleotide mismatches to the nucleotide sequence of SEQ ID NO: 3.

Promoters

In some embodiments, the polynucleotides, plasmids, viral vectors, vector systems, viral packaging systems, cells, and compositions further comprise a nucleotide sequence comprising, consisting of, or consisting essentially of one or more promoters. In some embodiments, the promoter is a eukaryotic promoter. Examples of eukaryotic promoters include, but are not limited to, a cytomegalovirus (CMV) promoter, elongation factor 1 alpha (EF1a) promoter, CAG promoter, phospholycerate kinase gene (PGK) promoter, tetracycline response element (TRE) promoter, human U6 nuclear (U6) promoter, and UAS promoter. In some embodiments, the promoter is a mammalian promoter. In some embodiments, the promoter is a constitutive promoter. In some embodiments, the promoter is an inducible promoter.

In some embodiments, the promoter is a tissue-specific promoter. Examples of tissues include, but are not limited to, muscle, epithelial, connective, and nervous tissue. Examples of tissue-specific promoters include, but are not limited to, B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, ICAM-2 promoter, INF-β promoter, Mb promoter, NphsI promoter, OG-2 promoter, SP-B promoter, SYN1 promoter, WASP promoter, SV40/bAlb promoter, SV40/hAlb promoter, SV40/CD43 promoter, SV40/CD45 promoter, and NSE/RU5' promoter.

In some embodiments, the promoter is a muscle-specific promoter. In some embodiments, the muscle-specific promoter is a myosin heavy chain complex-E box muscle creatine kinase fusion enhancer/promoter.

In some embodiments, the promoter is a recombinant promoter. In some embodiments, the recombinant promoter is a recombinant muscle-specific promoter. In some embodiments, the recombinant-muscle specific promoter is a recombinant myosin heavy chain-creatine kinase muscle-specific promoter. In another embodiment, the muscle-specific promoter comprises a human skeletal actin gene element, a cardiac actin gene element, a desmin promoter, a skeletal alpha-actin (ASKA) promoter, a troponin I (TNNI2) promoter, a myocytespecific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor.

In some embodiments, the promoter comprises the nucleotide sequence of SEQ ID NO: 4. In some embodiments, the promoter comprises a nucleotide sequence that is at least 80%, 82%, 85%, 87%, 90%, 92%, 93%, 94%, 95%, 96%, 97%, 98%, 99%, or 100% identical to the nucleotide sequence of SEQ ID NO: 4 across the full length of SEQ ID NO: 4.

Introns

In some embodiments, the polynucleotides, plasmids, viral vectors, vector systems, viral packaging systems, cells, and compositions further comprise a nucleotide sequence comprising, consisting of, or consisting essentially of one or more introns. In some embodiments, the intron is a eukaryotic intron. In some embodiments, the intron is a mammalian intron. In some embodiments, the intron is a synthetic intron. In some embodiments, the intron is a chimeric intron. In some embodiments, the intron is from a non-coding exon. In some embodiments, the intron is upstream of or 5' to the 5' hDYSF polynucleotide.

In some embodiments, the intron comprises at least one of a 5' donor site, branch point, or 3' splice site. In some embodiments, the intron comprises two or more of a 5' donor site, branch point, or 3' splice site. In some embodiments, the intron comprises a 5' donor site, branch point, and 3' splice site.

In some embodiments, the intron comprises a 5' donor site from a human β-globin gene.

In some embodiments, the intron comprises a branch point from an immunoglobulin G (IgG) heavy chain.

In some embodiments, intron comprises a 3' splice acceptor site from an immunoglobulin G (IgG) heavy chain In some embodiments, the intron comprises the nucleotide sequence of SEQ ID NO: 5. In some embodiments, the intron comprises a nucleotide sequence that is at least 80%, 82%, 85%, 87%, 90%, 92%, 93%, 94%, 95%, 96%, 97%, 98%, 99%, or 100% identical to the nucleotide sequence of SEQ ID NO: 5 across the full length of SEQ ID NO: 5.

Selection Marker

In some embodiments, the polynucleotides, plasmids, viral vectors, vector systems, viral packaging systems, cells, and compositions further comprise a nucleotide sequence comprising, consisting of, or consisting essentially of one or more selection markers. In some embodiments, the selection marker is a bacterial selectable marker. In some embodiments, the selection marker is an antibiotic resistance gene. Examples of antibiotic resistance genes include, but are not limited to, β-lactamase, kanamycin resistance gene, neo gene from Tn5, mutant FabI gene from *E. coli* genome, and URA3 (an orotidine-5' phosphate decarboxylase from yeast). In some embodiments, the antibiotic resistance gene is a β-lactamase gene. In some embodiments, the antibiotic resistance gene is a kanamycin resistance gene.

Polyadenylation Signal

In some embodiments, the polynucleotides, plasmids, viral vectors, vector systems, viral packaging systems, cells, and compositions further comprise a nucleotide sequence comprising, consisting of, or consisting essentially of one or more polyadenylation (polyA) signals. In some embodiments, the polyA signal is an artificial polyA signal.

In some embodiments, the poly A signal comprises the nucleotide sequence of SEQ ID NO: 7. In some embodiments, the polyA signal comprises a nucleotide sequence that is at least 80%, 82%, 85%, 87%, 90%, 92%, 93%, 94%, 95%, 96%, 97%, 98%, 99%, or 100% identical to the nucleotide sequence of SEQ ID NO: 7 across the full length of SEQ ID NO: 7.

Expression Cassettes and Packaging Systems

Further disclosed herein are adeno-associated viral (AAV) expression cassettes. In some embodiments, the AAV expression cassette comprises: (a) a first inverted terminal repeat (ITR), wherein the first ITR comprises any of the ITRs disclosed herein; (b) any of the 5' hDYSF polynucleotides disclosed herein; and (c) a second ITR, wherein the second ITR comprises any of the ITRs disclosed herein, wherein the 5' hYDSYF polynucleotide of (b) is flanked by the first and second ITRs of (a) and (c). In some embodiments, an AAV expression cassette comprising any of the 5' hDYSF polynucleotides disclosed herein is referred to as a 5' hDYSF AAV expression cassette.

Further disclosed herein are adeno-associated viral (AAV) plasmids. In some embodiments, the AAV expression cassette comprises: (a) a first inverted terminal repeat (ITR), wherein the first ITR comprises any of the ITRs disclosed herein; (b) any of the 3' hDYSF polynucleotides disclosed herein; and (c) a second ITR, wherein the second ITR comprises any of the ITRs disclosed herein, wherein the 3' hYDSYF polynucleotide of (b) is flanked by the first and second ITRs of (a) and (c). In some embodiments, an AAV expression cassette comprising any of the 3' hDYSF polynucleotides disclosed herein is referred to as a 3' hDYSF AAV expression cassette.

In some embodiments, an adeno-associated viral (AAV) expression cassette comprises: (a) a first inverted terminal repeat (ITR); (b) a polynucleotide sequence encoding a fragment of a human dysferlin (hDYSF) protein, wherein the polynucleotide sequence consists of: (i) the nucleotide sequence of SEQ ID NO: 1; (ii) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 1 across the full length of SEQ ID NO: 1; (iii) the nucleotide sequence of SEQ ID NO: 13; (iv) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 13 across the full length of SEQ ID NO: 13; (v) a nucleotide sequence encoding the hDYSF protein, wherein the hDYSF protein consists of the amino acid sequence of SEQ ID NO: 9; or (vi) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of (v) across the full length of the nucleotide sequence of (v); and (c) a second ITR, wherein the polynucleotide sequence is flanked by the first and second ITRs. In some embodiments, any of the AAV expression cassettes disclosed herein further comprise one or more additional polynucleotide sequences comprising a promoter, intron, selection marker, or origin of replication (ORI). In some embodiments, the AAV expression cassette comprises the nucleotide sequence of SEQ ID NO: 6. In some embodiments, the AAV expression cassette comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 6 across the full length of SEQ ID NO: 6. In some embodiments, the AAV expression cassette comprises the nucleotide sequence of SEQ ID NO: 15. In some embodiments, the AAV expression cassette comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 15 across the full length of SEQ ID NO: 15. In some embodiments, the AAV expression cassette does not further comprise a second polynucleotide sequence encoding a second fragment of the hDYSF protein. In some embodiments, the AAV expression cassette does not comprise an AAV sequence other than an inverted terminal repeat (ITR). In some embodiments, the AAV expression cassette does not comprise a viral sequence other than an inverted terminal repeat (ITR).

In some embodiments, an adeno-associated viral (AAV) expression cassettes comprises: (a) a first inverted terminal repeat (ITR); (b) a polynucleotide sequence encoding a fragment of a human dysferlin protein, wherein the polynucleotide sequence consists of: (i) the nucleotide sequence of SEQ ID NO: 2; (ii) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 2 across the full length of SEQ ID NO: 2; (iii) the nucleotide sequence of SEQ ID NO: 14; (ii) a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 14 across the full length of SEQ ID NO: 14; (v) a polynucleotide sequence encoding the hDYSF protein, wherein the hDYSF protein consists of the amino acid sequence of SEQ ID NO: 10; or (vi) a polynucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the polynucleotide sequence of (v) across the full length of the nucleotide sequence of (v); and (c) a second ITR, wherein the polynucleotide sequence is flanked by the first and second ITRs. In some embodiments, the AAV expression cassette comprises the nucleotide sequence of SEQ ID NO: 8. In some embodiments, the AAV expression cassette comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 8 across the full length of SEQ ID NO: 8. In some embodiments, the AAV expression cassette comprises the nucleotide sequence of SEQ ID NO: 16. In some embodiments, the AAV expression cassette comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence of SEQ ID NO: 16 across the full length of SEQ ID NO: 16. In some embodiments, the AAV expression cassette further comprises one or more polynucleotide sequences comprising a selection marker, origin of replication (ORI), untranslated region (UTR), or polyadenylation (polyA) signal.

Further disclosed herein are adeno-associated viral (AAV) packaging systems. In some embodiments, the AAV packaging systems comprise: (a) any of the 5' hDYSF AAV expression cassettes disclosed herein; (b) an adenovirus helper plasmid; and (c) a rep-cap plasmid. In some embodiments, the adenovirus helper plasmid comprises one or more genes from an adenovirus. In some embodiments, the one or more genes from the adenovirus mediate AAV replication. In some embodiments, the one or more genes from the adenovirus are selected from E4, E2a, and VA. In some embodiments, the rep-cap plasmid comprises one or more polynucleotides encoding the adeno-associated virus rep and cap genes. In some embodiments, the rep gene encodes for one or more of life cycle proteins selected from Rep78, Rep68, Rep62, and Rep40. In some embodiments, the cap gene encodes for one or more of capsid proteins selected from VP1, VP2, and VP3. In some embodiments, the 5' hDYSF AAV expression cassette comprises one or more ITRs. In some embodiments, the ITRs are AAV ITRs. In some embodiments, the serotype of the AAV ITRs is the same as the serotype of the AAV capsid protein. In some embodiments, the serotype of the AAV ITRs is different from the serotype of the AAV capsid protein. In some embodiments, the serotype of the AAV rep gene is the same as the serotype of the AAV capsid protein. In some embodiments, the serotype of the AAV rep gene is different from the serotype of the AAV capsid protein. In some embodiments, an AAV packaging system comprising any of the 5' hDYSF AAV expression cassettes disclosed herein is referred to as a 5' hDYSF AAV packaging system.

In some embodiments, the AAV packaging systems comprise: (a) any of the 3' hDYSF AAV expression cassettes disclosed herein; (b) an adenovirus helper plasmid; and (c) a rep-cap plasmid. In some embodiments, the adenovirus helper plasmid comprises one or more genes from an adenovirus. In some embodiments, the one or more genes from the adenovirus mediate AAV replication. In some embodiments, the one or more genes from the adenovirus are selected from E4, E2a, and VA. In some embodiments, the rep-cap plasmid comprises one or more polynucleotides encoding the adeno-associated virus rep and cap genes. In some embodiments, the rep gene encodes for one or more of life cycle proteins selected from Rep78, Rep68, Rep62, and Rep40. In some embodiments, the cap gene encodes for one or more of capsid proteins selected from VP1, VP2, and VP3. In some embodiments, the 3' hDYSF AAV expression cassette comprises one or more ITRs. In some embodiments, the ITRs are AAV ITRs. In some embodiments, the serotype of the AAV ITRs is the same as the serotype of the AAV capsid protein. In some embodiments, the serotype of the AAV ITRs is different from the serotype of the AAV capsid protein. In some embodiments, the serotype of the AAV rep gene is the same as the serotype of the AAV capsid protein. In some embodiments, the serotype of the AAV rep gene is different from the serotype of the AAV capsid protein. In some embodiments, an AAV packaging system comprising any of the 3' hDYSF AAV expression cassettes disclosed herein is referred to as a 3' hDYSF AAV packaging system.

In some embodiments, the adeno-associated viral packaging system comprises: (a) any of the 5' hDYSF AAV expression cassettes disclosed herein; and (b) an adenovirus helper plasmid. In some embodiments, the adenovirus helper plasmid comprises one or more genes from an adenovirus. In some embodiments, the one or more genes from the adenovirus mediate AAV replication. In some embodiments, the one or more genes from the adenovirus are selected from E4, E2a, and VA.

In some embodiments, the adeno-associated viral packaging system comprises: (a) any of the 3' hDYSF AAV expression cassettes disclosed herein; and (b) an adenovirus helper plasmid. In some embodiments, the adenovirus helper plasmid comprises one or more genes from an adenovirus. In some embodiments, the one or more genes from the adenovirus mediate AAV replication. In some embodiments, the one or more genes from the adenovirus are selected from E4, E2a, and VA.

Viral Vectors

Further disclosed herein are adeno-associated viral (AAV) vectors (e.g., AAV viruses or AAV particles). In some embodiments, the AAV vectors comprise, consist of, or consist essentially of any of the 5' hDYSF polynucleotides disclosed herein. In some embodiments, an AAV vector comprising any of the 5' hDYSF polynucleotides disclosed herein is referred to as a 5' hDYSF AAV vector.

In some embodiments, a 5' hDYSF AAV vector comprises any of the 5' hDYSF AAV expression cassettes disclosed herein.

In some embodiments, the AAV vectors comprise, consist of, or consist essentially of any of the 3' hDYSF polynucleotides disclosed herein. In some embodiments, an AAV vector comprising any of the 3' hDYSF polynucleotides disclosed herein is referred to as a 3' hDYSF AAV vector.

In some embodiments, a3' hDYSF AAV vector comprises any of the 3' hDYSF AAV expression cassettes disclosed herein.

In some embodiments, the AAV vector is an AAV of serotype 1, 2, 3, 4, 5, 6, 7, 8, 9, 10, 11, 12, 13, rh.10, rh.20, or rh.74. In some embodiments, the AAV vector is an AAV of serotype rh.74. In some embodiments, the AAV vector is not an AAV of serotype 5.

Further disclosed herein are dual adeno-associated viral (AAV) vector systems comprising two or more of the AAV vectors disclosed herein. In some embodiments, the dual AAV vector system comprises: (a) a first AAV vector, wherein the first AAV vector comprises any of the 5' hDYSF polynucleotides disclosed herein; and (b) a second AAV vector, wherein the second AAV vector comprises any of the 3' hDYSF polynucleotides disclosed herein.

In some embodiments, the dual AAV vector system comprises, consists of, or consists essentially of: (a) a first AAV vector, wherein the first AAV vector comprises, consists of, or consists essentially of any of the 5' hDYSF AAV vectors disclosed herein; and (b) a second AAV vector, wherein the second AAV vector comprises, consists of, or consists essentially of any of the 3' hDYSF AAV vectors disclosed herein.

Compositions

Further disclosed herein are compositions comprising, consisting of, or consisting essentially of any of the 5' hDYSF polynucleotides disclosed herein. Further disclosed herein are compositions comprising, consisting of, or consisting essentially of any of the 3' hDYSF polynucleotides disclosed herein. Further disclosed herein are compositions comprising, consisting of, or consisting essentially of any of the 5' hDYSF plasmids disclosed herein. Further disclosed herein are compositions comprising, consisting of, or consisting essentially of any of the 3' hDYSF plasmids disclosed herein. Further disclosed herein are compositions comprising, consisting of, or consisting essentially of any of the dual AAV vector systems disclosed herein. Further disclosed herein are compositions comprising, consisting of, or consisting essentially of any of the AAV vectors disclosed herein.

Further disclosed herein is a composition comprising, consisting of, or consisting essentially of: (a) a recombinant adeno-associated virus (rAAV) vector, wherein the rAAV vector comprises, consists of, or consists essentially of any of the 5' hDYSF polynucleotides disclosed herein; and (b) a pharmaceutically acceptable carrier, diluent, excipient, or adjuvant.

Further disclosed herein is a composition comprising, consisting of, or consisting essentially of: (a) a recombinant adeno-associated virus (rAAV) vector, wherein the rAAV comprises, consists of, or consists essentially of any of the 3' hDYSF polynucleotides disclosed herein; and (b) a pharmaceutically acceptable carrier, diluent, excipient, or adjuvant.

Further disclosed herein is a composition comprising, consisting of, or consisting essentially of: (a) a first recombinant adeno-associated virus (rAAV), wherein the first rAAV comprises, consists of, or consists essentially of any of the 5' hDYSF polynucleotides disclosed herein; and (b) a second recombinant adeno-associated virus (rAAV), wherein the second rAAV comprises, consists of, or consists essentially of any of the 3' hDYSF polynucleotides disclosed herein.

Further disclosed herein is a composition comprising, consisting of, or consisting essentially of: (a) a first adeno-associated viral (AAV) particle, wherein the first AAV particle comprises, consists of, or consists essentially of any of the 5' hDYSF AAV vectors disclosed herein; and (b) a second adeno-associated viral (AAV) particle, wherein the second AAV particle comprises, consists of, or consists essentially of any of the 3' hDYSF AAV vectors disclosed herein.

In some embodiments, any of the compositions disclosed herein further comprise at least one of a pharmaceutically acceptable carrier, diluent, excipient, or adjuvant. Acceptable carriers, diluents and adjuvants are nontoxic to recipients and are preferably inert at the dosages and concentrations employed and include buffers and surfactants such as pluronics. Examples of acceptable carriers include, but are not limited to, phosphate buffered saline, preservatives and the like.

The pharmaceutically acceptable carrier, diluent, or excipient may be suitable for injectable use. Examples of pharmaceutically acceptable carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the polynucleotides, plasmids, viral vectors, or dual vector systems disclosed herein in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Methods for Producing AAV Vectors

Disclosed herein are methods of producing an adeno-associated viral (AAV) vector (e.g., virus or viral particle). Methods of producing AAV vectors are known in the art. For instance, such methods are disclosed in, for example, WO 01/83692, which is incorporated by reference herein in its entirety. General principles of AAV production are reviewed in, for example, Carter, *Current Opinions in Biotechnology* 1533-1539, 1992; and Muzyczka, *Curr. Topics in Microbial, and Immunol.* 158:97-129, 1992, each of which are incorporated by reference in their entirety. Various approaches for producing AAVs are described in Ratschin et al., *Mol. Cell. Biol.* 4:2072, 1984; Hermonat et al., *Proc. Natl. Acad. Sci. USA,* 81:6466, 1984; Tratschin et al., *Mol. Cell. Biol.* 5:3251, 1985; Mclaughlin et al., *J. Virol.,* 62:1963, 1988; and Lebkowski et al., *Mol. Cell. Biol.,* 7:349, 1988; Samulski et al., J. Virol., 63:3822-3828, 1989; U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al., *Vaccine* 13:1244-1250, 1995; Paul et al., *Human Gene Therapy* 4:609-615, 1993; Clark et al., *Gene Therapy* 3:1124-1132, 1996; U.S. Pat. Nos. 5,786,211; 5,871,982; and 6,258,595, each of which are incorporated by reference in their entirety.

In some embodiments, the method for producing an adeno-associated viral (AAV) vector comprises transducing a cell with any of the AAV packaging systems disclosed herein. In some embodiments, the cell is a eukaryotic cell. In some embodiments, the cell is a mammalian cell. In some embodiments, the cell is a recombinant cell that stably expresses the adeno-associated virus rep and cap genes. In some embodiments, the method further comprises culturing the cell to produce a population of transduced cells. In some embodiments, the method further comprises collecting the supernatant from the population of transduced cells. In some embodiments, the method further comprises subjecting the supernatant to one or more purification steps to produce a purified AAV vector sample, wherein the AAV vector sample is substantially free from cellular debris and proteins. Alternatively, or additionally, the method further comprises lysing the population of transduced cells to produce a cellular lysate. In some embodiments, the method further comprises subjecting the cellular lysate to one or more purification steps to produce a purified AAV vector sample, wherein the AAV vector sample is substantially free from cellular debris and proteins. In some embodiments, the purity of the purified AAV vector sample is at least 85%, 86%, 87%, 88%, 89%, 90%, 91%, 92%, 93%, 94%, 95%, 96%, 97%, 98%, 99% or 100% pure.

In some embodiments, the method for producing an adeno-associated viral (AAV) vector comprises transducing a cell with any of the 5' hDYSF AAV packaging systems disclosed herein. In some embodiments, the cell is a eukaryotic cell. In some embodiments, the cell is a mammalian cell. In some embodiments, the cell is a recombinant cell that stably expresses the adeno-associated virus rep and cap genes. In some embodiments, the method further comprises culturing the cell to produce a population of transduced cells. In some embodiments, the method further comprises collecting the supernatant from the population of transduced cells. In some embodiments, the method further comprises subjecting the supernatant to one or more purification steps to produce a purified AAV vector sample, wherein the AAV vector sample is substantially free from cellular debris and proteins. Alternatively, or additionally, the method further comprises lysing the population of transduced cells to produce a cellular lysate. In some embodiments, the method further comprises subjecting the cellular lysate to one or more purification steps to produce a purified AAV vector sample, wherein the AAV vector sample is substantially free from cellular debris and proteins. In some embodiments, the purity of the purified AAV vector sample is at least 85%, 86%, 87%, 88%, 89%, 90%, 91%, 92%, 93%, 94%, 95%, 96%, 97%, 98%, 99% or 100% pure.

In some embodiments, the method for producing an adeno-associated viral (AAV) vector comprises transducing a cell with any of the 3' hDYSF AAV packaging systems disclosed herein. In some embodiments, the cell is a eukaryotic cell. In some embodiments, the cell is a mammalian cell. In some embodiments, the cell is a recombinant cell that stably expresses the adeno-associated virus rep and cap genes. In some embodiments, the method further comprises culturing the cell to produce a population of transduced cells. In some embodiments, the method further comprises collecting the supernatant from the population of transduced cells. In some embodiments, the method further comprises subjecting the supernatant to one or more purification steps to produce a purified AAV vector sample, wherein the AAV vector sample is substantially free from cellular debris and proteins. Alternatively, or additionally, the method further comprises lysing the population of transduced cells to produce a cellular lysate. In some embodiments, the method further comprises subjecting the cellular lysate to one or more purification steps to produce a purified AAV vector sample, wherein the AAV vector sample is substantially free from cellular debris and proteins. In some embodiments, the purity of the purified AAV vector sample is at least 85%, 86%, 87%, 88%, 89%, 90%, 91%, 92%, 93%, 94%, 95%, 96%, 97%, 98%, 99% or 100% pure.

Cells

Further disclosed herein are cells comprising any of the 5' hDYSF polynucleotides disclosed herein. The cells can be prokaryotic or eukaryotic cells. Non-limiting examples of eukaryotic cells include mammalian, e.g., hamster, murine, rat, canine, ovine or human cells. In some embodiments, the cells are transfected with a plasmid comprising any of the 5' hDYSF polynucleotides disclosed herein. In some embodiments, the cells are transduced with any of the 5' hDYSF AAV expression cassettes disclosed herein. In some embodiments, the cells are infected with any of the 5' hDYSF AAV vectors disclosed herein.

Further disclosed herein are cells comprising any of the 3' hDYSF polynucleotides disclosed herein. In some embodiments, the cells are transfected with a plasmid comprising any of the 3' hDYSF polynucleotides disclosed herein. In some embodiments, the cells are transduced with any of the 3' hDYSF AAV expression cassettes disclosed herein. In some embodiments, the cells are infected with any of the 3' hDYSF AAV vectors disclosed herein.

Any of the cells disclosed herein may be packaging cells that produce infectious rAAV. In some embodiments, the packaging cells are stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells). Non-limiting examples of prokaryotic cells comprise bacterial cells (e.g., *Escherichia coli*) and archaeal cells. The cells of the disclosure can be used to produce a cell bank, e.g., an Accession Cell Banks (ACB) for non-GMP purpose or GMP Master Cell Bank (MCB). The aliquote of the cells, in one embodiment, are expanded from an original inoculum to a larger volume before culture in the bioreactor for the production.

Methods of Treatment

Further disclosed herein are methods of treating a dysferlinopathy. In some embodiments, a method of treating a dysferlinopathy comprises, consists of, or consists essentially of administering to a subject in need thereof: (a) an effective amount of a first polynucleotide, wherein the first polynucleotide comprises any of the 5' hDYSF polynucleotides disclosed herein; and (b) an effective amount of a second polynucleotide, wherein the second polynucleotide comprises any of the 3' hDYSF polynucleotides disclosed herein. In some embodiments, the first polynucleotide is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the first polynucleotide is administered intramuscularly or intravenously. In some embodiments, the second polynucleotide is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the second polynucleotide is administered intramuscularly or intravenously. In some embodiments, the first and second polynucleotides are administered simultaneously. In some embodiments, the first and second polynucleotides are administered sequentially. In some embodiments, the dysferlinopathy is limb girdle muscular dystrophy type 2B (LGMD2B) or Miyoshi myopathy.

In some embodiments, a method of treating a dysferlinopathy comprises, consists of, or consists essentially of administering to a subject in need thereof: (a) an effective amount of a first adeno-associated viral (AAV) vector, wherein the first AAV vector comprises any of the 5' hDYSF AAV vectors disclosed herein; and (b) an effective amount of a second adeno-associated viral (AAV) vector, wherein the second AAV vector comprises any of the 3' hDYSF AAV vectors disclosed herein. In some embodiments, the first AAV vector is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the first AAV vector is administered intramuscularly or intravenously. In some embodiments, the second AAV vector is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the second AAV vector is administered intramuscularly or intravenously. In some embodiments, the first and second AAV vectors are administered simultaneously. In some embodiments, the first and second AAV vectors are administered sequentially. In some embodiments, the dysferlinopathy is limb girdle muscular dystrophy type 2B (LGMD2B) or Miyoshi myopathy.

In some embodiments, a method of treating a dysferlinopathy comprises, consists of, or consists essentially of administering to a subject in need thereof: (a) an effective amount of a first AAV expression cassette, wherein the first AAV expression cassette comprises any of the 5' hDYSF AAV expression cassettes disclosed herein; and (b) an effective amount of a second AAV expression cassette, wherein the second AAV expression cassette comprises any of the 3' hDSYF AAV expression cassettes disclosed herein. In some embodiments, the first AAV expression cassette is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the first AAV expression cassette is administered intramuscularly or intravenously. In some embodiments, the second AAV expression cassette is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the second AAV expression cassette is administered intramuscularly or intravenously. In some embodiments, the first and second AAV expression cassettes are administered simultaneously. In some embodiments, the first and second AAV expression cassettes are administered sequentially. In some embodiments, the dysferlinopathy is limb girdle muscular dystrophy type 2B (LGMD2B) or Miyoshi myopathy.

In some embodiments, a method of treating a dysferlinopathy comprises, consists of, or consists essentially of administering to a subject in need thereof an effective amount of a composition comprising (a) any of the 5' hDYSF polynucleotides disclosed herein and any of the 3' hDYSF polynucleotides disclosed herein; (b) any of the 5' hDYSF AAV vectors disclosed herein and any of the 3' hDYSF AAV vectors disclosed herein; (c) any of the 5' hDYSF AAV expression cassettes disclosed herein and any of the 3' hDYSF AAV expression cassettes disclosed herein; or (d) any of the dual AAV vector systems disclosed herein. In some embodiments, the composition is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the composition is administered intramuscularly or intravenously. In some embodiments, the dysferlinopathy is limb girdle muscular dystrophy type 2B (LGMD2B) or Miyoshi myopathy.

Further disclosed herein are uses of any of the recombinant polynucleotides, plasmids, viral vectors, vector systems, and compositions in the manufacture of a medicament to treat a dysferlinopathy in a subject in need thereof. Disclosed herein is use of a composition comprising (a) any of the 5' hDYSF polynucleotides disclosed herein and any of the 3' hDYSF polynucleotides disclosed herein; (b) any of the 5' hDYSF AAV vectors disclosed herein and any of the 3' hDYSF AAV vectors disclosed herein; (c) any of the 5' hDYSF AAV expression cassettes disclosed herein and any of the 3' hDYSF AAV expression cassettes disclosed herein; or (d) (e) any of the dual AAV vector systems disclosed herein in the manufacture of a medicament to treat a dysferlinopathy in a subject in need thereof. In some embodiments, the composition is administered orally, parenterally (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.). In some embodiments, the composition is administered intramuscularly or intravenously. In some embodiments, the dysferlinopathy is limb girdle muscular dystrophy type 2B (LGMD2B) or Miyoshi myopathy.

Titers of AAV vectors to be administered in methods of the invention will vary depending, for example, on the particular AAV, the mode of administration, the treatment goal, the individual, and the cell type(s) being targeted, and may be determined by methods standard in the art. Titers of AAV may range from at least about $1\times10^{6}$, about $1\times10^{7}$, about $1\times10^{8}$, about $1\times10^{9}$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). For instance, dosages of AAV may range from at least about $1\times10^{6}$, about $1\times10^{7}$, about $1\times10^{8}$, about $1\times10^{9}$, about $1\times10^{10}$, about $1\times10^{11}$, about $1\times10^{12}$, about $2\times10^{12}$, about $3\times10^{12}$, about $4\times10^{12}$, about $5\times10^{12}$, about $6\times10^{12}$, about $7\times10^{12}$, about $8\times10^{12}$, about $9\times10^{12}$, about $1\times10^{13}$ to about $1\times10^{14}$ viral genomes.

AAV dosage can be determined by multiple methods, which include but are not limited to ELISA, assessment of the reverse transcriptase activity, FACS, transduction assays northern blotting (e.g., semi-quantitative northern), dot blot analysis or PCR (e.g., qPCR). It is well known that the AAV doses can be determined by measuring AAV vector genomes with quantitative real-time PCR (qPCR). Such qPCR methods overcome the inconsistency or arbitrary results from conventional transduction assays. In one embodiment of PCR dosage determination, plasmid DNA is used as a calibration standard. The forms of the plasmids can impact the dosage results from the qPCR methods. In one embodiment, the circular or supercoiled DNA or plasmids are used as a quantification standard.

In some embodiment, dosages may be expressed in the units of vg/kg, based on a supercoiled DNA or plasmid as the quantitation standard. For example, dosages of AAV is about $1\times10^{6}$-$1\times10^{16}$ vg/kg, about $1\times10^{8}$-$1\times10^{15}$ vg/kg, or about $1\times10^{10}$-$1\times10^{14}$ vg/kg,), based on a supercoiled DNA or plasmid as the quantitation standard. In another embodiment, the dosages is about at least $1\times10^{6}$, about $1\times10^{7}$, about $1\times10^{8}$, about $1\times10^{9}$, about $1\times10^{10}$, about $1\times10^{11}$, about $1\times10^{12}$, about $2\times10^{12}$, about $4\times10^{12}$, about $6\times10^{12}$, about $8\times10^{12}$, about $1\times10^{13}$, about $2\times10^{13}$, about $2.4\times10^{13}$, about $3\times10^{13}$, about $4\times10^{13}$, about $5\times10^{13}$, about $6\times10^{13}$, about $7\times10^{13}$, about $8\times10^{13}$, about $9\times10^{13}$, about $1\times10^{14}$, about $1\times10^{15}$, or at least about $1\times10^{16}$ vg/kg. In one embodiment, the dosage is at least $2\times10^{12}$, $4\times10^{12}$, $6\times10^{12}$, $8\times10^{12}$, $1\times10^{13}$, $2\times10^{13}$, $2.4\times10^{13}$, $3\times10^{13}$, $4\times10^{13}$, $5\times10^{13}$, $6\times10^{13}$, $7\times10^{13}$, or $8\times10^{13}$ vg/kg, based on a supercoiled DNA or plasmid as the quantitation standard.

In some embodiments, the methods disclosed herein comprise administering at least about $1\times10^{6}$, about $1\times10^{7}$, about $1\times10^{8}$, about $1\times10^{9}$, about $1\times10^{10}$, about $1\times10^{11}$, about $1\times10^{12}$, about $2\times10^{12}$, about $3\times10^{12}$, about $4\times10^{12}$, about $5\times10^{12}$, about $6\times10^{12}$, about $7\times10^{12}$, about $8\times10^{12}$, about $9\times10^{12}$, about $1\times10^{13}$ vg in a total volume of 1.5 ml per injection. In some embodiments, the methods disclosed herein comprise administering a total daily dose of at least about $1\times10^{6}$, about $1\times10^{7}$, about $1\times10^{8}$, about $1\times10^{9}$, about $1\times10^{10}$, about $1\times10^{11}$, about $1\times10^{12}$, about $2\times10^{12}$, about $3\times10^{12}$, about $4\times10^{12}$, about $5\times10^{12}$, about $6\times10^{12}$, about $7\times10^{12}$, about $8\times10^{12}$, about $9\times10^{12}$, about $1\times10^{13}$, about $2\times10^{13}$, about $5\times10^{13}$, about $7\times10^{13}$, about $1\times10^{14}$ vg. One exemplary method of determining encapsidated vector genome titer uses quantitative PCR, such as the methods described in Pozsgai et al., *Mol. Ther.* 25(4): 855-869, 2017, which is incorporated by reference in its entirety.

In some embodiments, any of the polynucleotides, plasmids, viral vectors, dual vector systems, or compositions disclosed herein are administered to the subject at least 1, 2, 3, 4, 5, 6, 7, 8, 9, or 10 times a day. In some embodiments, any of the polynucleotides, plasmids, viral vectors, dual vector systems, or compositions disclosed herein are administered to the subject at least 1, 2, 3, 4, 5, 6, 7, 8, 9, 10, 11, 12, 13, 14, 15, 16, 17, 18, 19, or 20 times a week. In some embodiments, any of the polynucleotides, plasmids, viral vectors, dual vector systems, or compositions disclosed herein are administered to the subject at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 times a month. In some embodiments, any of the polynucleotides, plasmids, viral vectors, dual vector systems, or compositions disclosed herein are administered to the subject at least every 1, 2, 3, 4, 5, 6, 7, 8, 9, or 10 days. In some embodiments, any of the polynucleotides, plasmids, viral vectors, dual vector systems, or compositions disclosed herein are administered to the subject at least every 1, 2, 3, 4, 5, 6, 7, 8, 9, 10, 11, 12, 13, or 14 weeks. In some embodiments, any of the polynucleotides, plasmids, viral vectors, dual vector systems, or compositions disclosed herein are administered to the subject for a period of at least 1, 2, 3, 4, 5, 6, 7, 8, 9, or 10 days. In some embodiments, any of the polynucleotides, plasmids, viral vectors, dual vector systems, or compositions disclosed herein are administered to the subject for a period of at least 1, 2, 3, 4, 5, 6, 7, 8, 9, 10, 11, 12, 13, 14, 15, 16, 17, 18, 19, or 20 weeks. In some embodiments, any of the polynucleotides, plasmids, viral vectors, dual vector systems, or compositions disclosed herein are administered to the subject for a period of at least 1, 2, 3, 4, 5, 6, 7, 8, 9, 10, 12, 13, 14, 15, 16, 17, 18, 19, or 20 months.

In some embodiments, the methods disclosed herein comprise administering any of the polynucleotides, plasmids, viral vectors, dual vector systems, or compositions disclosed herein systemically. For example, systemic administration is administration into the circulatory system so that the entire body is affected. Systemic administration includes enteral administration such as absorption through the gastrointestinal tract and parenteral administration through injection, infusion or implantation.

In some embodiments, the methods disclosed herein comprise administering any of the polynucleotides, plasmids, viral vectors, dual vector systems, or compositions disclosed herein locally. In some embodiments, the methods disclosed herein comprise administering any of the polynucleotides, plasmids, viral vectors, dual vector systems, or compositions disclosed herein to one or more tissues. In some embodiments, the tissue is selected from muscle, epithelial, connective, and nervous tissue. In some embodiments, the tissue is a muscle tissue.

In some embodiments, the methods disclosed herein comprise administering any of the polynucleotides, plasmids, viral vectors, dual vector systems, or compositions disclosed herein to the subject's foot. In some embodiments, the methods disclosed herein comprise administering any of the polynucleotides, plasmids, viral vectors, dual vector systems, or compositions disclosed herein to the subject's extensor digitorum brevis (EDB) muscle.

Combination therapies are also contemplated by the invention. Combination as used herein includes both simultaneous treatment and sequential treatments. Combinations of methods of the invention with standard medical treatments (e.g., corticosteroids) are specifically contemplated, as are combinations with novel therapies.

In some embodiments, the methods disclosed herein further comprise detecting the presence or absence of a mutation in a dysferlin gene in the subject prior to or subsequent to administering any of the polynucleotides, plasmids, viral vectors, dual vector systems, or compositions disclosed herein to the subject. In some embodiments, any of the polynucleotides, plasmids, viral vectors, dual vector systems, or compositions disclosed herein are administered to the subject upon detection of the presence of the mutation in the dysferlin gene. Exemplary dysferlin mutations include, but are not limited to, c. 1392dupA, c.3035G>A (p.W1012X), c.2858dupT, c.2779del G, c.5594delG, c.4201dupA, c. 1795_1799dupTACT, c.3832C>T (p.Q1278X), c.757C>T (p.R253W), c.855+1delG, c.3126G>A (p.W1042X), c.1663C>T (p.R555W), c.610C>T (p.R204X), c.3112C>T (p.R1038X), c.1368C>G (p.C456W), c.5713C>T (p.R1905X), c.3826C>G (p.I1276V), c.3843+1G>A, c.4167+1G>C, c.2643+1G>A, c.797T>C (p.I266P), c4876delG, c.3477C>A (p.Y1159X), c.3137G>A (p.R1046H), c.509C>A (p.A170E), c.3967C>T (p.Q1323X), 3191_3196dupGAGGCG, c.3992G>T (p.R1331L), c.3516_3517delTT, c.247delG, c. 1180+11C>T, c896G>A (p.G299E), c.5078G>A (p.R1693Q), c.5979dupA, c.3348+1_3348+4delGTAT, c.5314_5318delAGCCC, and c565C>G (p.L189V). In some instances, the dysferlin gene comprises one or more mutations including, but not limited to, c. 1392dupA, c.3035G>A (p.W1012X), c.2858dupT, c.2779del G, c.5594delG, c.4201dupA, c. 1795_1799dupTACT, c.3832C>T (p.Q1278X), c.757C>T (p.R253W), c.855+1delG, c.3126G>A (p.W1042X), c.1663C>T (p.R555W), c.610C>T (p.R204X), c.3112C>T (p.R1038X), c.1368C>G (p.C456W), c.5713C>T (p.R1905X), c.3826C>G (p.I1276V), c.3843+1G>A, c.4167+1G>C, c.2643+1G>A, c.797T>C (p.I266P), c4876delG, c.3477C>A (p.Y1159X), c.3137G>A (p.R1046H), c.509C>A (p.A170E), c.3967C>T (p.Q1323X), 3191_3196dupGAGGCG, c.3992G>T (p.R1331L), c.3516_3517delTT, c.247delG, c.1180+11C>T, c896G>A (p.G299E), c.5078G>A (p.R1693Q), c.5979dupA, c.3348+1_3348+4delGTAT, c.5314_5318delAGCCC, and c565C>G (p.L189V).

In some embodiments, the methods disclosed herein further comprise detecting levels of dysferlin protein in the subject prior to administering or subsequent to any of the polynucleotides, plasmids, viral vectors, dual vector systems, or compositions disclosed herein to the subject. In some embodiments, the methods disclosed herein further comprise detecting levels of dysferlin protein in the subject after administering any of the polynucleotides, plasmids, viral vectors, dual vector systems, or compositions disclosed herein to the subject. In some embodiments, detecting the levels of dysferlin comprises detecting expression of the dysferlin gene. Detecting expression of the dysferlin gene may comprise quantifying dysferlin DNA or RNA levels. Alternatively, or additionally, detecting the levels of dysferlin protein comprises quantifying the levels of dysferlin protein. In some embodiments, the levels of dysferlin protein are detected in a sample from the subject. In some embodiments, the sample is a body fluid sample. Examples of body fluid samples include, but are not limited to, blood, urine, sweat, saliva, stool, and synovial fluid. In some embodiments, the blood sample is a plasma or serum sample. In some instances, the method further comprises a dysferlin DNA sequencing test, e.g., from Athena Diagnostics (CPT: 81408(1)).

In some embodiments, the methods disclosed herein further comprise modifying the dose or dosing frequency of any of the polynucleotides, plasmids, viral vectors, dual vector systems, or compositions that is administered to the subject. In some embodiments, modifying the dose or dosing frequency is based on the detection of dysferlin protein levels. In some embodiments, the dose or dosing frequency is reduced when dysferlin protein levels in the subject increase as compared to the dysferlin protein levels in the subject from an earlier time point (e.g., prior to administering the polynucleotides, plasmids, viral vectors, dual vector systems, or compositions, or after administering an initial dose of the polynucleotides, plasmids, viral vectors, dual vector systems, or compositions, but prior to administering a subsequent dose of the polynucleotides, plasmids, viral vectors, dual vector systems, or compositions).

Kits

In a yet further aspect, a kit is provided that comprises, or alternatively consists essentially of, or yet further consisting of, any of one or more of the polynucleotides, polypeptides, vectors, cells and systems, or the compositions, and instructions for use. In one aspect, any of one or more of the polynucleotides, polypeptides, vectors, cells and systems, or the compositions are detectably labeled or further comprise a purification or detectable marker. In some instances, the kit comprises a) a first polynucleotide, wherein the first polynucleotide is the recombinant polynucleotide described herein, and a second polynucleotide, wherein the second polynucleotide is the recombinant polynucleotide described herein; or b) a first adeno-associated viral (AAV) vector, wherein the first AAV vector is the AAV vector described herein, and a second adeno-associated viral (AAV) vector, wherein the second AAV vector is the AAV vector described herein; or c) an AAV dual vector system described herein; or d) a composition described herein; or e) a cell (e.g., a host cell, optionally mammalian cell) described herein; and optionally an instruction for use.

EXAMPLES

Example 1: Generation of a Dual AAV Vector System

This example provides an exemplary method for producing the dual AAV vector systems disclosed herein. In this example, the dual AAV vector, rAAVrh.74.MHCK7.DYSF.DV is produced. The rAAVrh.74.MHCK7.DYSF.DV is a non-replicating, recombinant AAV, serotype rh74 (AAVrh74) expressing human dysferlin from dual vectors (DV) under the control of the muscle specific MHCK7 promoter. The dual vectors contain either the 5' portion or the 3' portion of the dysferlin cDNA sequence, and these portions are overlapping by ~1 kb to facilitate recombination to produce a full length human dysferlin gene. The expression cassette containing a portion of the human dysferlin cDNA is flanked by AAV2 inverted terminal repeat sequences (ITR) (FIG. 1).

To construct rAAVrh.74.MHCK7.DYSF.DV, the human dysferlin cDNA was split into two constructs that adhered to the packaging capacity of AAV (<4.7 kb). The 5' vector (e.g., 5' hDYSF AAV vector), pAAV.MHCK7.DYSF5'.PTG (PTG-promoter/transgene) contains a muscle specific MHCK7 promoter, chimeric intron, consensus Kozak sequence and 5'portion of the DYSF cDNA corresponding to amino acids 1-1113 of the Dysferlin amino acid sequence. The 3' vector (e.g., 3' hDYSF AAV vector), pAAV.DYSF3'.POLYA, contains a 3'portion of the DYSF cDNA corresponding to amino acids 794-2080 of the Dysferlin amino acid sequence and DYSF 3'UTR harboring a polyadenylation signal. Sequences of the expression cassettes of the 5' hDYSF AAV vector and 3' hDYSF AAV vector are disclosed as SEQ ID NOs: 6 and 8, respectively.

Previous studies have validated cardiac expression using MHCK7 promoter (Salva et al. *Mol Ther* 15, 320-329 (2007), which is incorporated by reference in its entirety) and AAVrh74 achieving skeletal, diaphragm, and cardiac muscle expression (Sondergaard et al. *Annals of clinical and Transl Neurology* 2, 256-270 (2015), which is incorporated by reference in its entirety). The 5' hDYSF AAV vector and 3' hDSYF AAV vector were encapsidated into separate AAVrh.74 virions. The molecular clone of the AAVrh.74 serotype was cloned from a rhesus macaque lymph node and is discussed in in Rodino-Klapac et al. *Journal of Translational medicine* 5, 45 (2007), which is incorporated by reference in its entirety.

5' hDYSF AAV Vector (AAV Vector Plasmid pAAV.MHCK7.DYSF5'.PTG)

Figure 2:
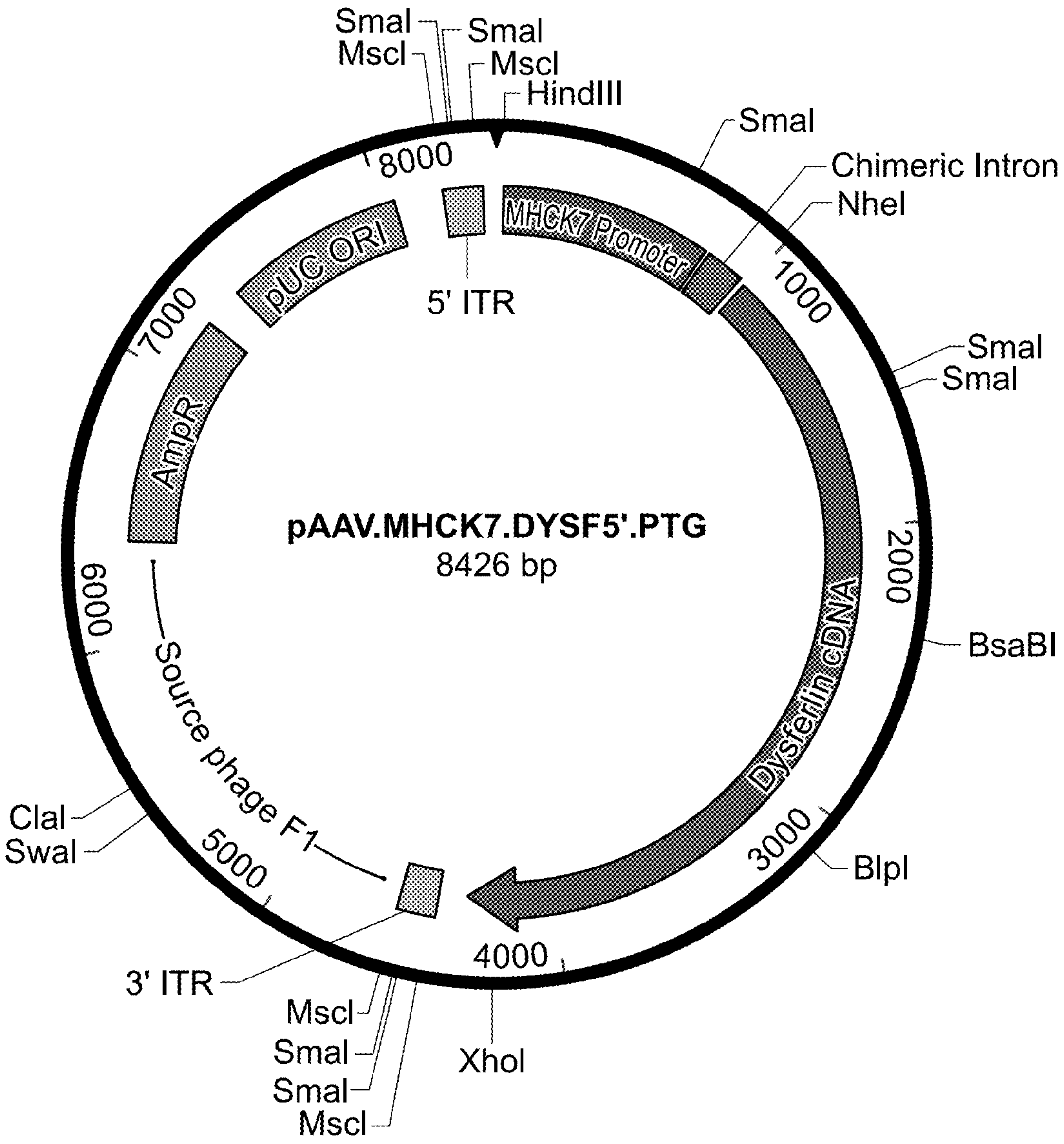
FIG. 2 provides the pAAV.MHCK7.DYSF5'.PTG DNA Vector Plasmid Map.

The first recombinant single-stranded AAV vector was produced using the AAV vector DNA plasmid pAAV.MHCK7.DYSF5'.PTG. The plasmid was constructed by inserting the MHCK7 expression cassette driving a 5' portion of the human dysferlin partial cDNA sequence (human cDNA, Genbank Accession #NM_003494.3) into the vector backbone pAAV-CMV (Clontech) (see FIG. 2 for plasmid map and Table 1 for specific sequence information). A chimeric intron was present and composed of the 5' donor site from the first intron of the human-globin gene and the branch point and 3' splice acceptor site from the intron that is between the leader and the body of an immunoglobulin gene heavy chain variable region. The only viral sequences included in this vector are the inverted terminal repeats of AAV2, which are required for both viral DNA replication and packaging of the rAAV vector genome. The sequence between the two ITRs is the portion of DNA that is encapsidated into AAVrh74 virions.

TABLE 1

Molecular Features of one exemplary plasmid pAAV.MHCK7.DYSF5'.PTG

| TYPE | START | END | NAME | DESCRIPTION |
|---|---|---|---|---|
| REGION | 8229 | 8373 | 5' ITR | Wild-type AAV2 inverted terminal repeat |
| REGION | 22 | 813 | MHCK7 | Mouse myosin heavy chain complex-E box muscle creatine kinase fusion enhancer/promoter |
| REGION | 823 | 970 | Chimeric intron | 5' donor site from human β-globin gene and the branch point and 3' splice acceptor site from IgG heavy chain |
| GENE | 993 | 4329 | hDYSF cDNA | Human dysferlin cDNA (transcript variant 8; 377-3716) aa1-1113 |
| REGION | 4440 | 4584 | 3' ITR | Wild-type AAV2 inverted terminal repeat |
| GENE | 6370 | 7230 | AmpR | β-lactamase gene |
| REGION | 7378 | 8045 | ori | Plasmid origin of replication |

3' hDYSF AAV Vector (AAV Vector Plasmid pAAV.DYSF3'.POLY)

Figure 3:
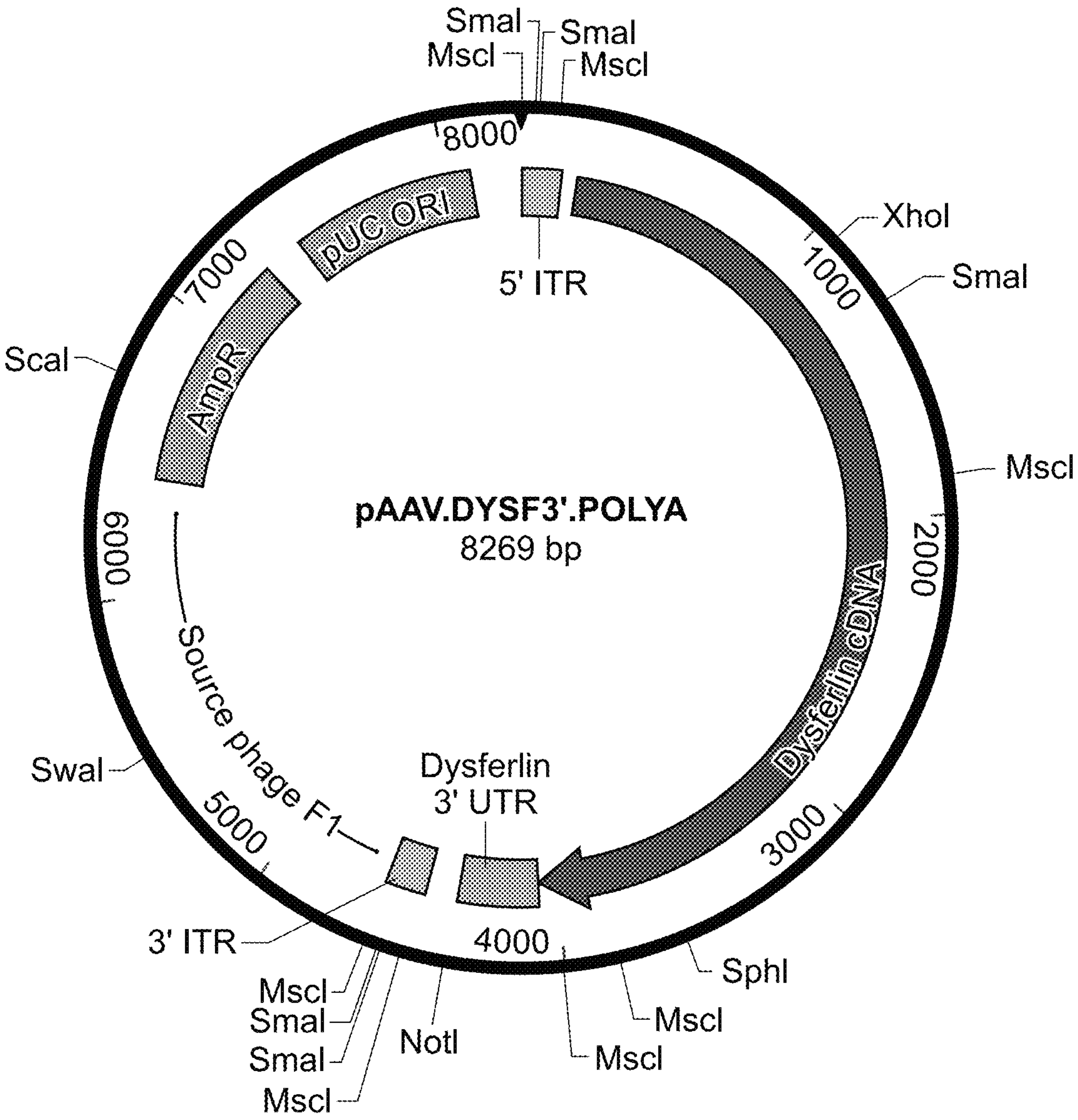
FIG. 3 provides the pAAV.DYSF3'.POLYA Vector DNA Plasmid Map.

The second recombinant single-stranded AAV vector was produced using the AAV vector DNA plasmid pAAV.DYSF3'.POLYA. The plasmid was constructed by inserting the human dysferlin partial cDNA sequence (human cDNA, Genbank Accession #NM_003494.3) into the vector backbone pAAV-CMV (Clontech) (see FIG. 3 for plasmid map and Table 2 for specific sequence information). The endogenous dysferlin 3' untranslated region and polyA signal sequences were used for efficient transcription termination. The only viral sequences included in this vector are the inverted terminal repeats of AAV2, which are required for both viral DNA replication and packaging of the rAAV vector genome. The sequence between the two ITRs is the portion of DNA that is encapsidated into AAVrh74 virions.

TABLE 2

Molecular Features of one exemplary plasmid PAAV.DYSF3'.POLYA

| TYPE | START | END | NAME | DESCRIPTION |
|---|---|---|---|---|
| REGION | 1 | 145 | 5' ITR | Wild-type AAV2 inverted terminal repeat |
| GENE | 204 | 3866 | hDYSF cDNA | Human dysferlin cDNA (transcript variant 8; 2754-6619) aa794-2080 |
| REGION | 4070 | 4364 | hDYSF 3' UTR | 3' untranslated region of the human dysferlin gene |
| REGION | 4378 | 4427 | pA | Artificial polyadenylation signal |
| REGION | 4481 | 4625 | 3' ITR | Wild-type AAV2 inverted terminal repeat |
| GENE | 6411 | 7271 | AmpR | β-lactamase gene |
| REGION | 7419 | 8086 | ori | Plasmid origin of replication |

AAV Helper Plasmid (pNLRep2-Caprh74)

The parent plasmid, pNLrep, was constructed from p5E18 and pCLR3K. (See Bansal, D., et al. Defective membrane repair in dysferlin-deficient muscular dystrophy. *Nature* 423, 168-172 (2003), which is incorporated by reference in its entirety). p5E18 is based on pAAV/Ad. It contains the AAV2 rep and cap genes, with the p5 promoter removed from the 5' end of rep and placed at the 3' end of cap, which results in the presence of a 3 kb spacer sequence between p5 and rep (see Table 3 for specific sequence information). To generate pCLR3K, the human collagen intron was amplified by PCR and then cloned into pAd/AAV at position 1,052. To construct pNLrep, the BamHI/XbaI fragment of p5E18 was replaced with the BamHI/XbaI fragment containing the 3 kb collagen intron from pCLR3k. The rh74 cap gene was PCR amplified and cloned in place of the AAV2 cap gene in pNLrep using Swa I/Not I restriction sites to yield pNL-Rep2-Caprh74. The identity of the AAV rh74 capsid gene was confirmed by DNA plasmid sequencing.

TABLE 3

Molecular Features of plasmid pNLRep2-Caprh.74

| TYPE | START | END | NAME | DESCRIPTION |
|---|---|---|---|---|
| GENE | 84 | 815 | 5' end of Rep78 | 5' end of Rep78 ORF |
| REGION | 816 | 3886 | Col Intron | 3 kb human collagen intron |
| GENE | 3887 | 5017 | 3' end of Rep78 | 3' end of Rep78 ORF |
| GENE | 5037 | 7253 | rh74 Cap | rh74 cap gene |
| REGION | 7428 | 7507 | p5 promoter | AAV2 p5 promoter region |

Adenovirus Helper Plasmid (pHELP)

Plasmid pHELP was obtained from Applied Viromics (Fremont, CA 94538) and is 11,635 bp in size (see Table 4 for specific sequence information). The plasmid contains the regions of adenovirus genome that are important for AAV replication, namely E2A, E4, and VA RNA (the adenovirus E1 functions are provided by 293 cells). The plasmid was based on a pBluescript backbone and also contains, the bla gene encoding the TEM-1 β-lactamase gene conferring resistance to ampicillin (10,182-11,042 bp), a bacterial ColE1 origin of replication (9,315-10,167 bp) and f1 single-strand DNA replication origin (11,172-11,627 bp). The adenovirus sequences present in this plasmid represent only ~28% (9,280/35,938) of the adenovirus genome, and does not contain cis elements critical for replication such as the inverted terminal repeats. The identity of these 3 adenovirus genes were confirmed by DNA plasmid sequencing performed. DNA Analysis revealed 100% homology with the 3 Adenovirus type 5 gene regions (GenBank Accession number AF369965, which is incorporated by reference in its entirety).

TABLE 4

Molecular Features of plasmid pHELP

| TYPE | START | END | NAME | DESCRIPTION |
|---|---|---|---|---|
| REGION | 1 | 5336 | E2A | DNA binding protein, required for AAV helper functions. |
| REGION | 5337 | 8537 | E4 | E4 ORF6 required for AAV helper functions. |
| REGION | 8537 | 9280 | VA RNA | Viral Associated RNA is non-coding RNA that regulates viral translation and is required for AAV helper functions. |
| GENE | 11,042 | 10,182 | Ampr | Ampicillin resistance gene |

Example 2: Manufacturing of Viral Products Using a Dual AAV Vector System

HEK 293 cells were transfected with the 3 production plasmids ((i) AAV vector plasmid, e.g., 5' hDYSF AAV vector or 3' hDYSF AAV vector; (ii) adenovirus (Ad) helper plasmid; and (iii) AAV helper plasmid) using an optimized calcium phosphate co-precipitation method. Transfecting the cells comprises preparing a DNA/calcium solution containing the AAV vector plasmid, Ad helper plasmid, AAV helper plasmid and $CaCl_2$) and mixing with an equal volume of 2×HEPES buffered saline to obtain an optimal precipitate. The precipitate was then added to the HEK 293 cells and incubated. The precipitate was then added to the HEK 293 cells and incubated. Post incubation the medium was exchanged at which time nuclease is added.

Figure 4A:
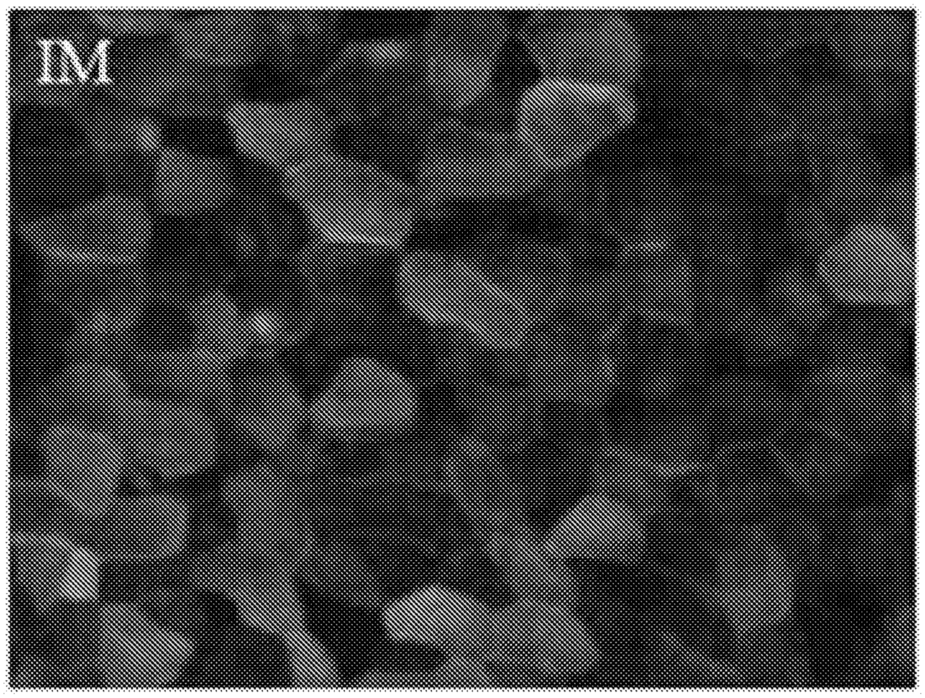
FIGS. 4A-4D show dysferlin expression following delivery of a dual vector system. Robust full-length dysferlin expression was seen following delivery of both vectors by immune staining (FIG. 4A) and western blot (FIG. 4C). Delivery of either vector alone had no aberrant dysferlin expression
Figure 4B:
Figure 4C:
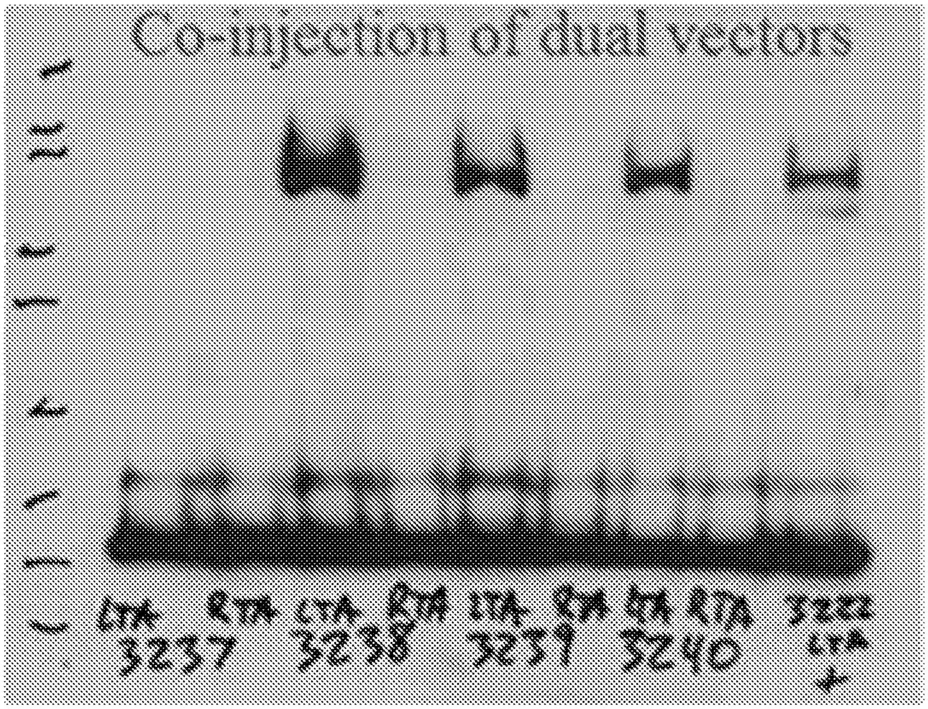
Figure 4D:
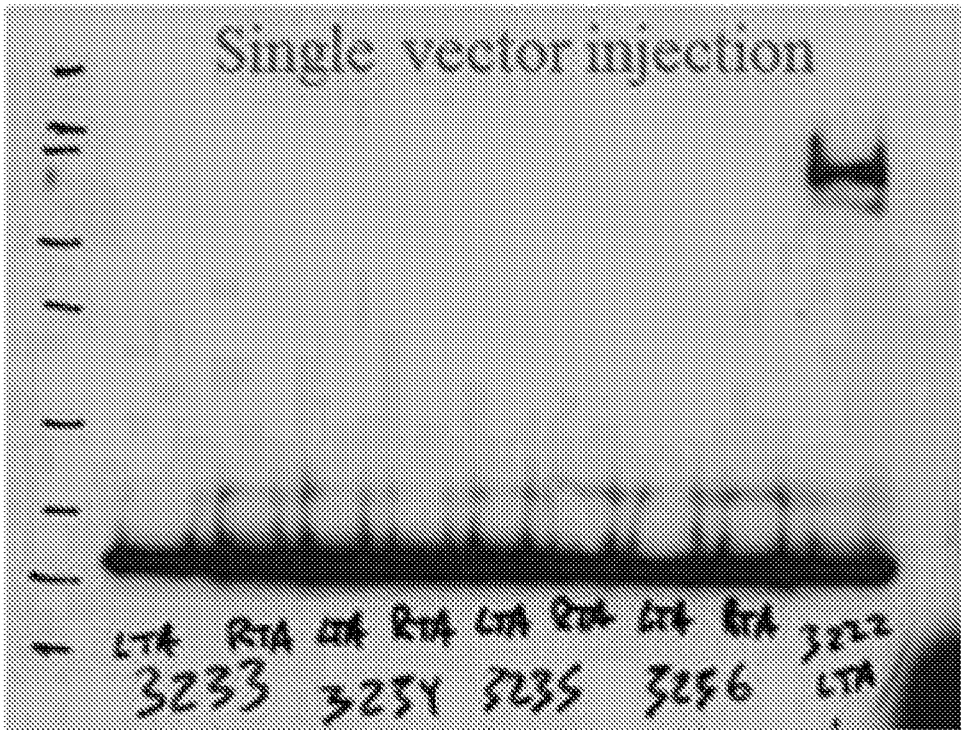

Example 3: Determination of Efficacy of rAAVrh.74.MHCK7.DYSF.DV Intramuscular Delivery The two AAV expression cassettes were generated containing 5' and 3' portions of the MHCK7.DYSF cassette with ~1 kb of overlapping sequence (see FIG. 1). The plasmids were packaging into AAVrh.74 vectors. 4 week old Dysf/ mice were treated with $1\times10^{11}$ vg of each vector by intramuscular injection into the tibialis anterior muscle and necropsied at 1 month. Robust full-length dysferlin expression was seen following delivery of both vectors by immune staining (FIG. 4A) and western blot (FIG. 4C). Delivery of either vector alone had no aberrant dysferlin expression (FIG. 4B, immune staining, and FIG. 4D, western blot). 3222 is the full-length control. The number of muscle fibers expressing dysferlin was quantified and shown in Table 5.

TABLE 5

| Dysferlin expression following IM delivery of rAAVrh.74.MHCK7.DYSF.DV | | | | | |
|---|---|---|---|---|---|
| Test Article (vector | Animal ID (eartag #) | Animal Strain | Endpoint (months) | Dose | % Fibers expressing Dysf* |
| rAAVrh.74.MHCK7.DYSF.DV | 3266 | $Dysf^{-/-}$ | 1 | $2 \times 10^{11}$ vg | 75% |
| | 3267 | | | | 68% |
| | 3268 | | | | 81% |
| | 674 | | | | 63% |
| | 675 | | | | 83% |

*Four 20x fields were counted per muscle (~550-600 fibers per animal)

Figure 5A:
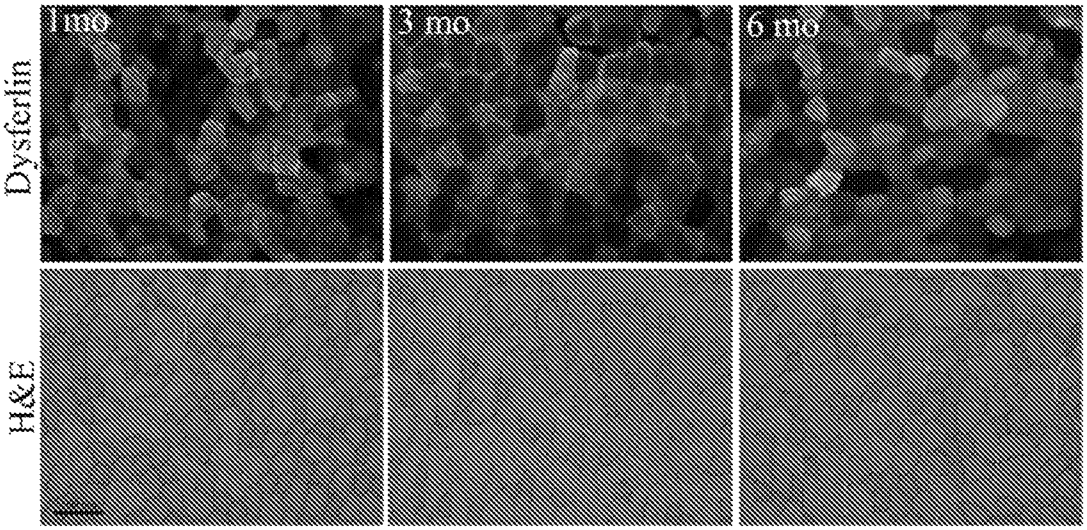
FIGS. 5A-5C show results of timecourse of dysferlin expression following rAAVrh74.MHCK7.DYSF.DV delivery.
Figure 5B:
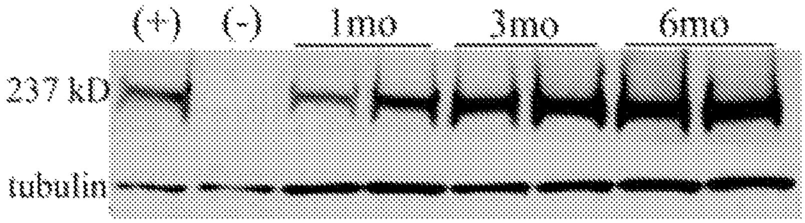
Figure 5C:
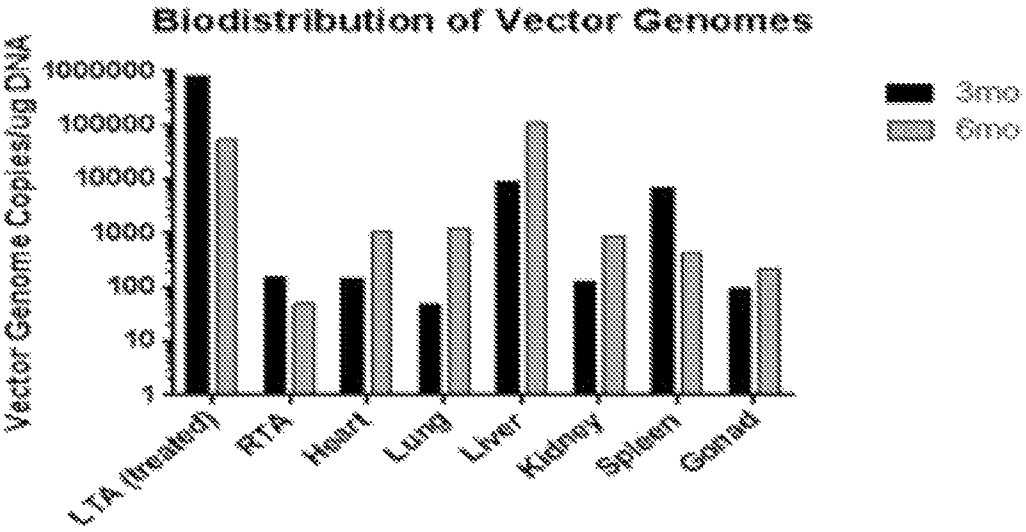

A time course study to assess safety following intramuscular injection to the tibialis anterior muscle was initiated (Table 6). Protein expression and vector biodistribution were also assessed. At 1, 3, 6, 9, and 12 month endpoints animals were fully necropsied and assessed for dysferlin expression (FIGS. 5A-5C (1, 3, and 6 months shown)), vector biodistribution (Table 7) and histopathology on muscle and non-target organs. The tibialis muscle (TA) was injected. Tissues analyzed for histopathology for each animal included: Gonad, liver, heart, lung, spleen, kidney, diaphragm, left (treated) and right tibialis anterior muscles. No findings were identified.

TABLE 6

| rAAVrh.74.MHCK7.DYSF.DV Long-Term Safety Study | | | | | |
|---|---|---|---|---|---|
| Test Article (vector | Animal ID (eartag #) | Animal Strain | Endpoint (months) | Dose | % Fibers expressing Dysf* |
| rAAVrh.74.MHCK7.DYSF.DV | 832 | $Dysf^{+/-}$ | 3 | $2 \times 10^{11}$ vg | 70% |
| | 833 | | | | 78% |
| | 834 | | | | 79% |
| | 835 | | 6 | | 90% |
| | 836 | | | | 91% |
| | 815 | | | | 68% |
| | 816 | | 9 | | 70% |
| | 817 | | | | 79% |
| | 818 | | | | 68% |
| | 819 | | 12 | | 89% |
| | 820 | | | | 87% |
| | 821 | | | | 89% |

*Four 20x fields were counted per muscle (~550-600 fibers per animal)

TABLE 7

| Vector biodistribution in rAAVrh.74.MHCK7.DYSF.DV treated animals at three months | | | |
|---|---|---|---|
| | Vector genome copies/μg | | |
| Tissue | Animal 832 | Animal 833 | Animal 834 |
| LTA (treated muscle) | 1.12E+05 | 1.12E+05 | 2.61E+05 |
| RTA (contralateral muscle) | Undet. | 1.87E+02 | 1.02E+02 |
| Heart | 4.54E+03 | 1.96E+03 | 9.11E+02 |
| Lung | 2.62E+03 | 1.00E+04 | 6.86E+02 |
| Liver | 2.42E+05 | 9.19E+04 | 2.24E+05 |
| Kidney | 6.71E+03 | 2.76E+03 | 1.86E+02 |
| Spleen | 4.13E+03 | 3.43E+03 | 4.49E+02 |
| Gonad | 2.30E+02 | 3.32E+02 | 4.15E+01 |

Figure 6:
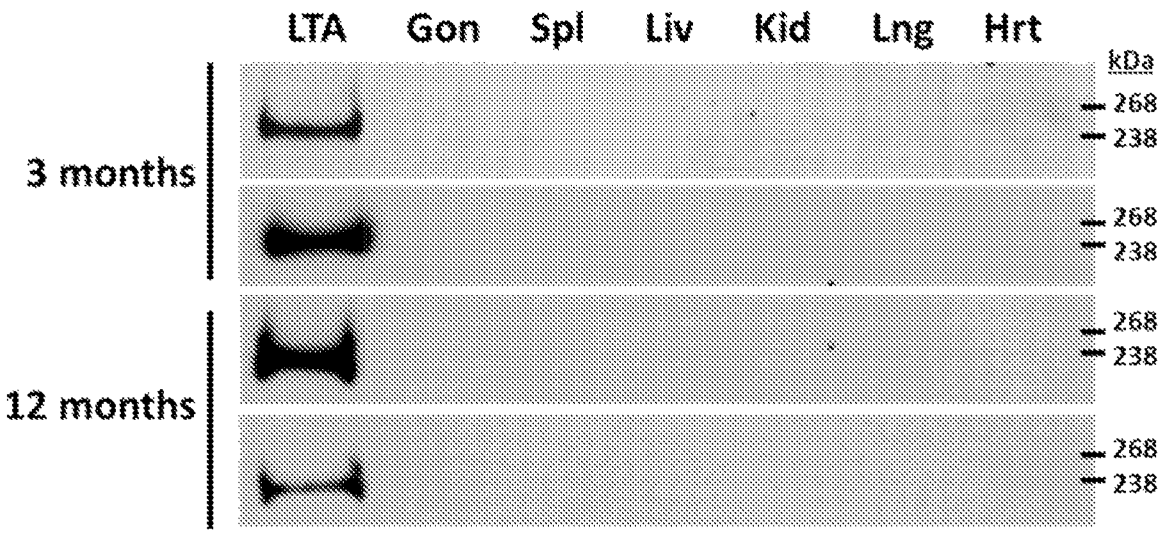
FIG. 6 shows Western blot analysis of target muscle (LTA) and non-target tissues from 4 individual animals treated by intramuscular injection with rAAVrh.74.MHCK7.DYSF.DV at 3 or 12 month endpoints.
Figure 7A:
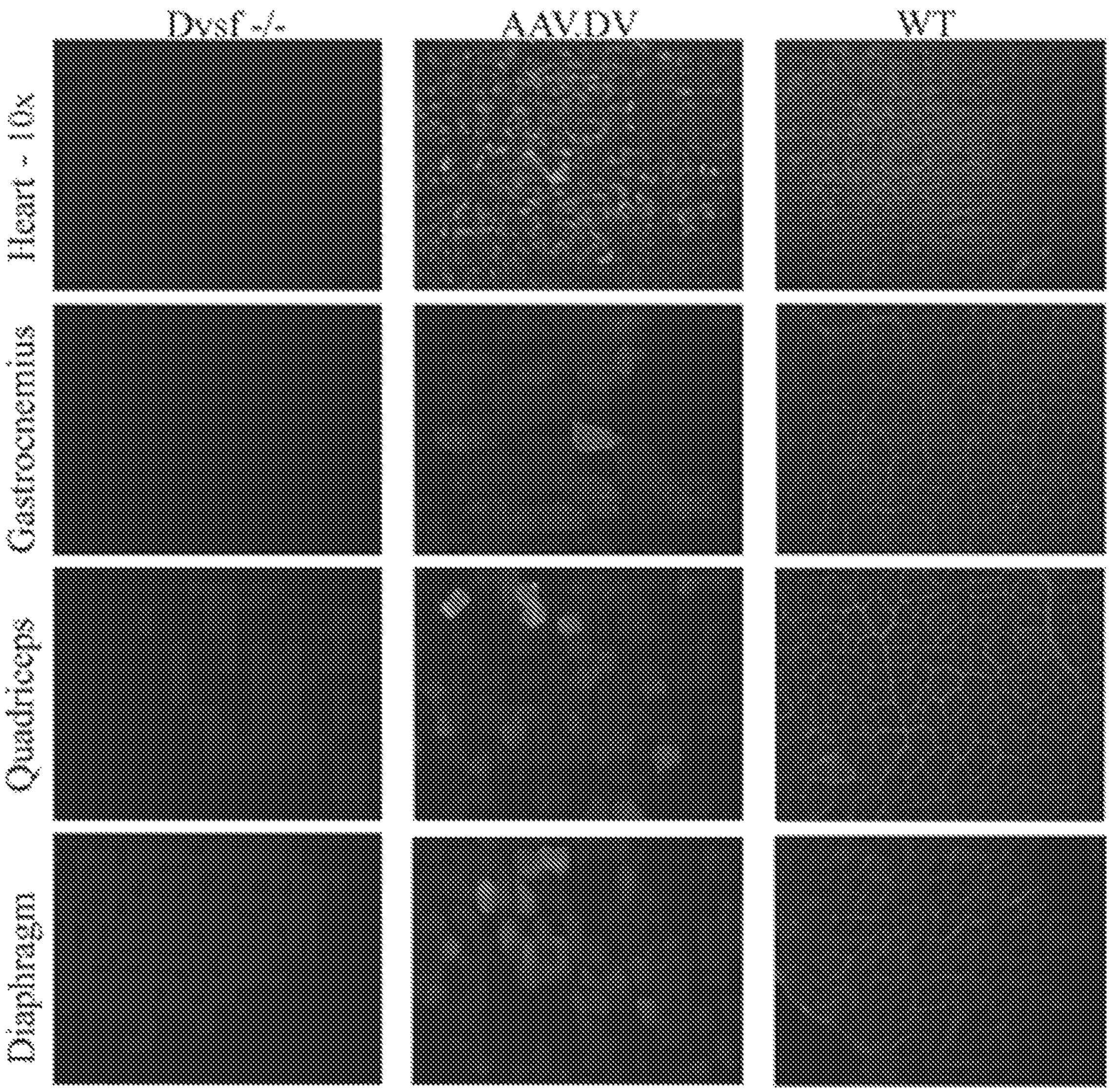
FIGS. 7A-7C show dysferlin expression following systemic delivery of AAVrh.74.MHCK7.DYSF.DV.

Following intramuscular injection, expression of dysferlin was found in the injected tibialis anterior muscle (FIG. 6). Following intravenous delivery, expression of dysferlin was found in skeletal and heart muscle (FIG. 7A).

Figure 8:
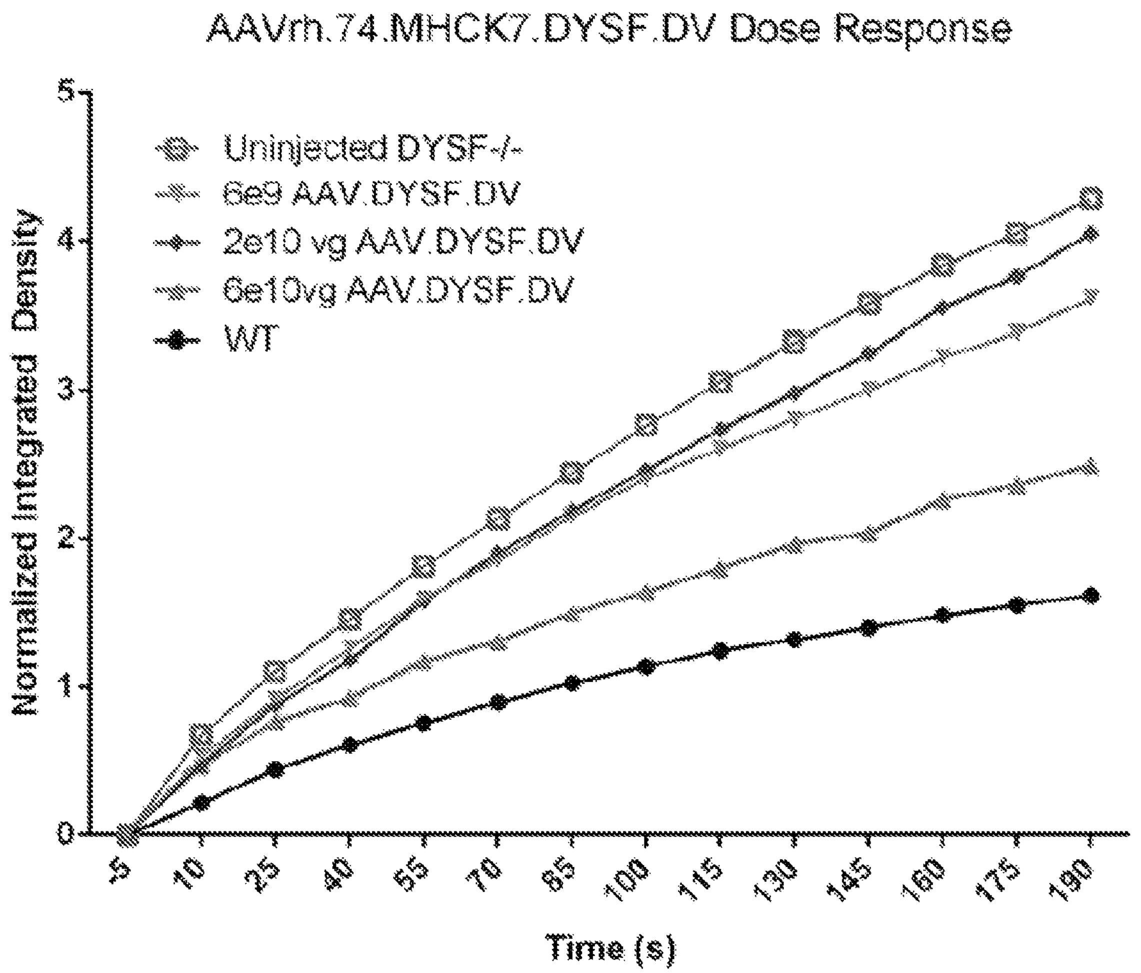
FIG. 8 shows dose-dependent membrane resealing activity following AAVrh.74.DYSF.DV delivery.

Additional cohorts of mice were treated to determine the minimum effective dose for membrane repair. Three doses of AAV vectors were injected into the FDB of 129Dysf−/− mice at 8 weeks of age (n=6 per group). A control Dysf−/− group received saline and a group of 129WT mice served as strain specific normal controls. As shown in FIG. 8, AAVrh.74.DYSF.DV treatment revealed dose dependent membrane resealing. Parallel expression studies show that high dose results in expression >50% of fiber transduction. This dose is equivalent to what was given to the tibialis anterior muscle for the expression and safety studies when normalized for muscle weight (FIGS. 4A-5C).

TABLE 8

| AAVrh.74.MHCK7.Dysferlin.DV Dose Response | | | |
|---|---|---|---|
| Mouse Strain | Treatment | Total Dose (vg) | 12 weeks |
| 129-$Dysf^{tm1Kcam/J}$ | AAvrh.74.MHCK7.Dysf.DV | $6 \times 10^{9}$ | n = 6 |
| 129-$Dysf^{tm1Kcam/J}$ | AAvrh.74.MHCK7.Dysf.DV | $2 \times 10^{10}$ | n = 6 |
| 129-$Dysf^{tm1Kcam/J}$ | AAvrh.74.MHCK7.Dysf.DV | $6 \times 10^{10}$ | n = 6 |
| 129-$Dysf^{tm1Kcam/J}$ | PBS | N/A | n = 6 |
| 129S1/SvImJ Normal Controls | PBS | N/A | n = 6 |

Systemic Delivery of rAAVrh.74.MHCK7.DYSF.DV

A dose finding study was conducted to test the feasibility/effectiveness of systemic delivery of dual vector delivery. BlaJ mice (AJ dysferlin deficient mice backcrossed onto BL6 mice) were used for the study based on an established functional MRI/MRS outcome in this strain. 3 groups of mice (n=6 per group) were treated at 6 weeks of age by tail vein injection with either saline, 2e12 vg total AAV.DYSF DV (8e13 vg/kg, based on a supercoiled DNA or plasmid as the quantitation standard), or 6e12 vg total AAV.DYSF.DV (2.4e13 vg/kg, based on a supercoiled DNA or plasmid as the quantitation standard). Endpoint analysis occurred at 3 months and included diaphragm physiology, membrane repair assay in the FDB, and full necropsies to quantify dysferlin expression and assess histopathology.[4]

Figure 7B:
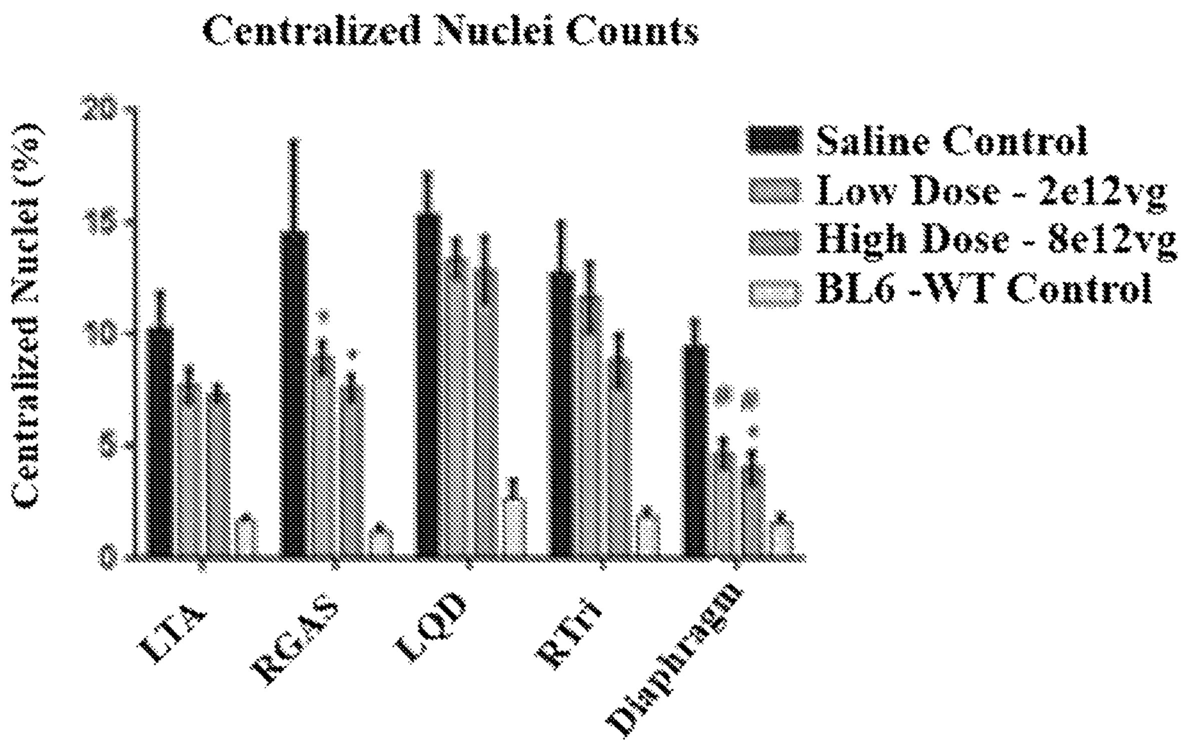
Figure 7C:
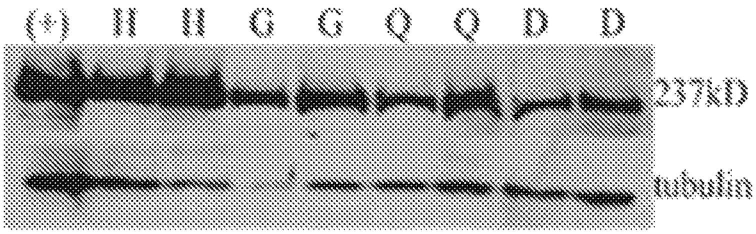
Figure 9:
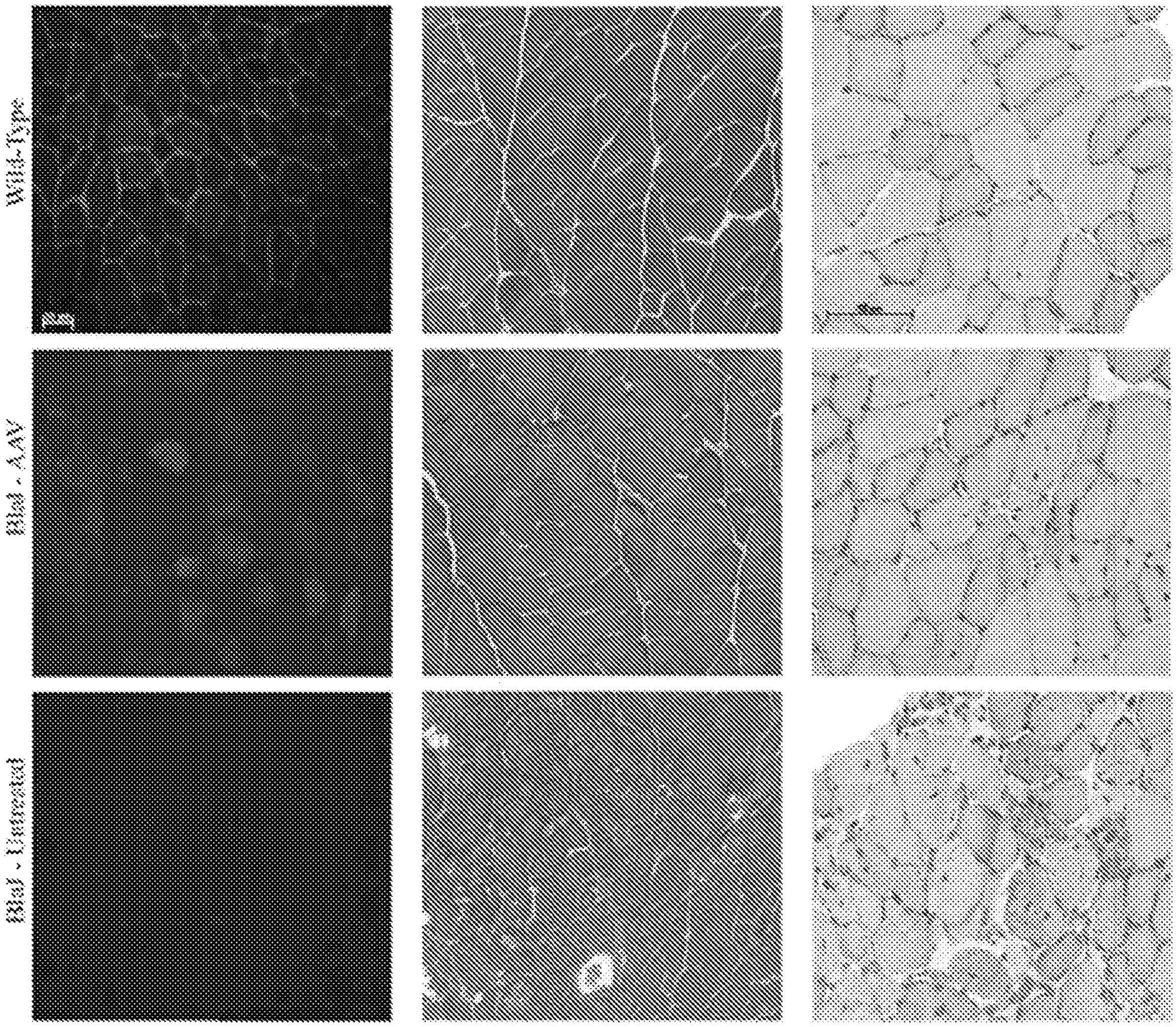
FIG. 9 shows a reversal of fibrosis and inflammation following systemic delivery of AAVrh.74.MHCK7.DYSF.DV. BlaJ mice were treated with $6\times10^{12}$ vg (2.4e13 vg/kg), based on a supercoiled DNA or plasmid as the quantitation standard. AAVrh.74.MHCK7.DYSF.DV (n=6). The psoas muscle was removed and analyzed for the presence of fibrosis (middle column) and CD8 mononuclear cells. There was a significant reduction in both parameters following gene delivery.
Figure 10A:
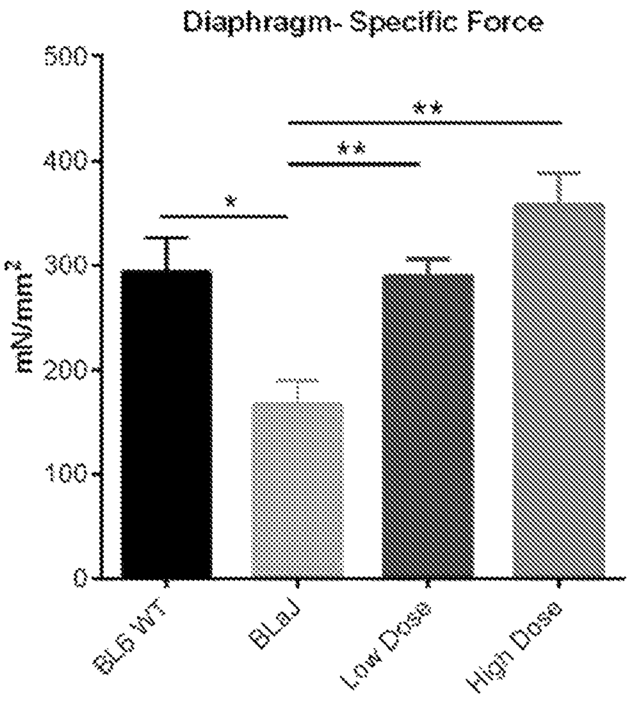
FIGS. 10A-10B demonstrate that systemic delivery of rAAVrh.74.MHCK7.DYSF.DV restores functional deficits in Dysf−/− mice.
Figure 10B:
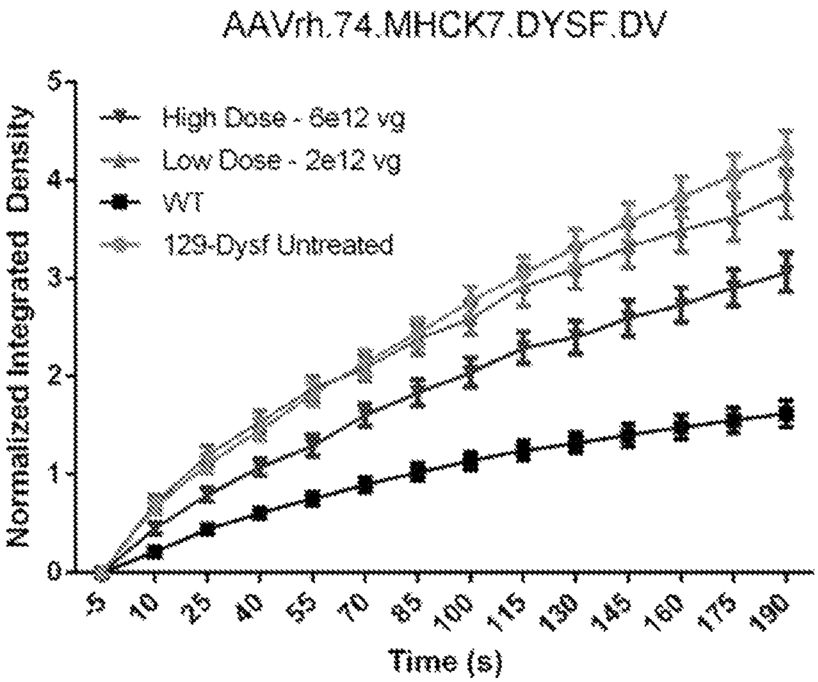
Figure 11A:
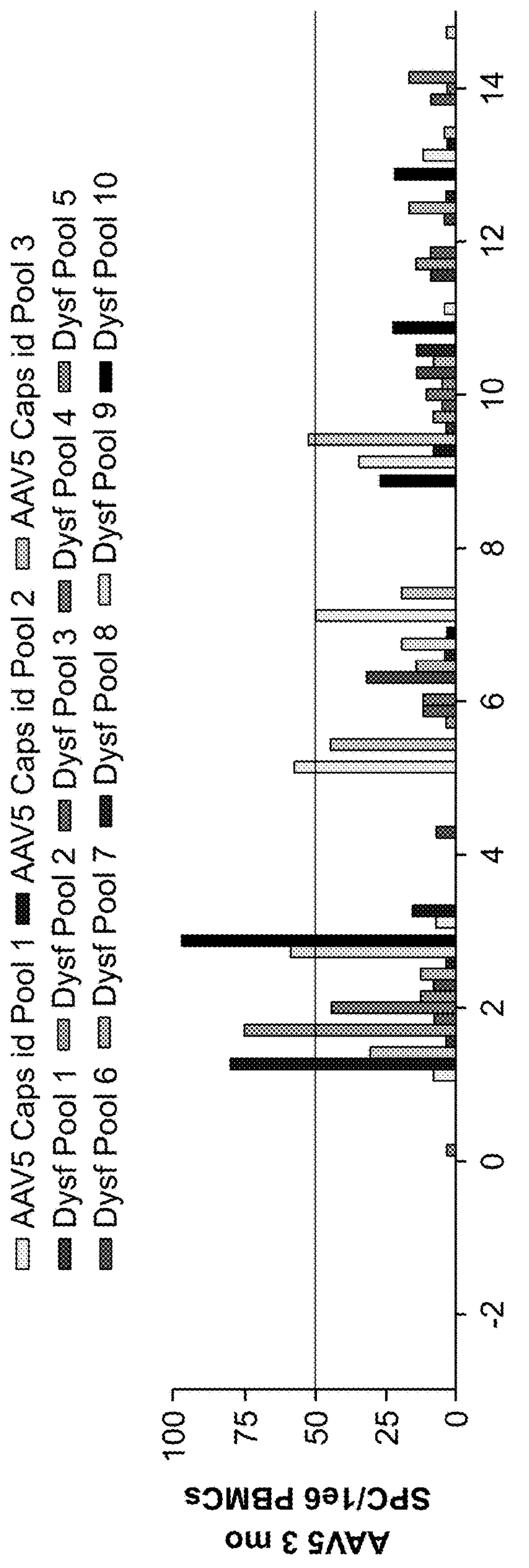
FIGS. 11A-11D shows results from monitoring of T cell responses to AAV capsid and dysferlin. Peripheral blood mononuclear cells were isolated and exposed to peptides comprising the AAV5 and AAVrh.74 capsid (blue bars) as well as human dysferlin (green). T cell responses to AAV5 capsid and dysferlin were monitored at 3 months (FIG. 11A) and 6 months (FIG. 11B). T cell responses to AAVrh.74 capdis and dysferlin were monitored at 3 months (FIG. 11C) and 6 months (FIG. 11D).
Figure 11B:
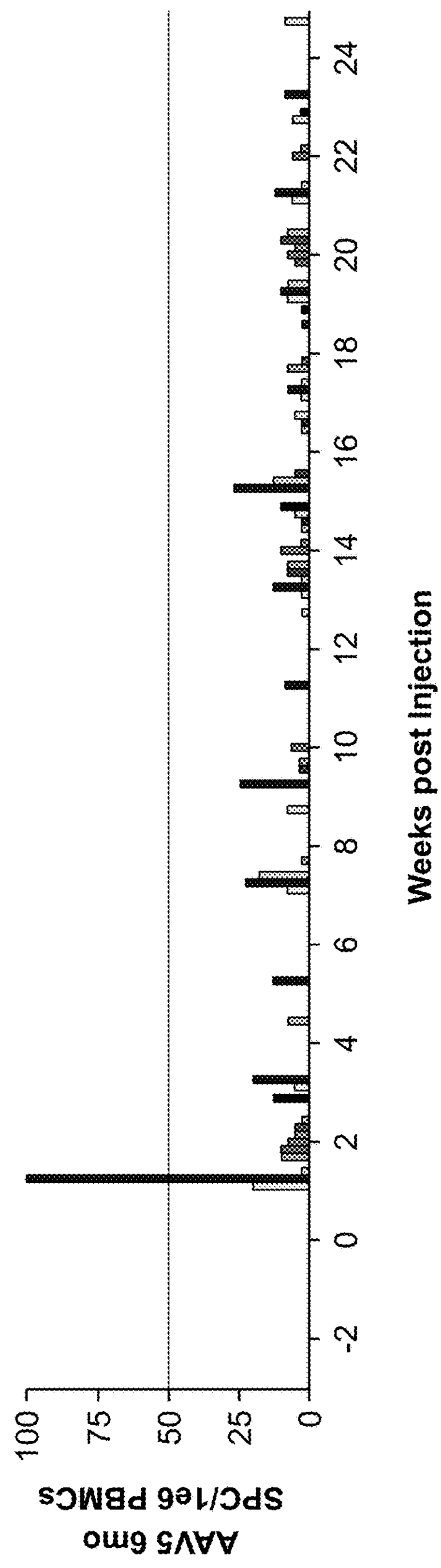
Figures 11C, 11D:
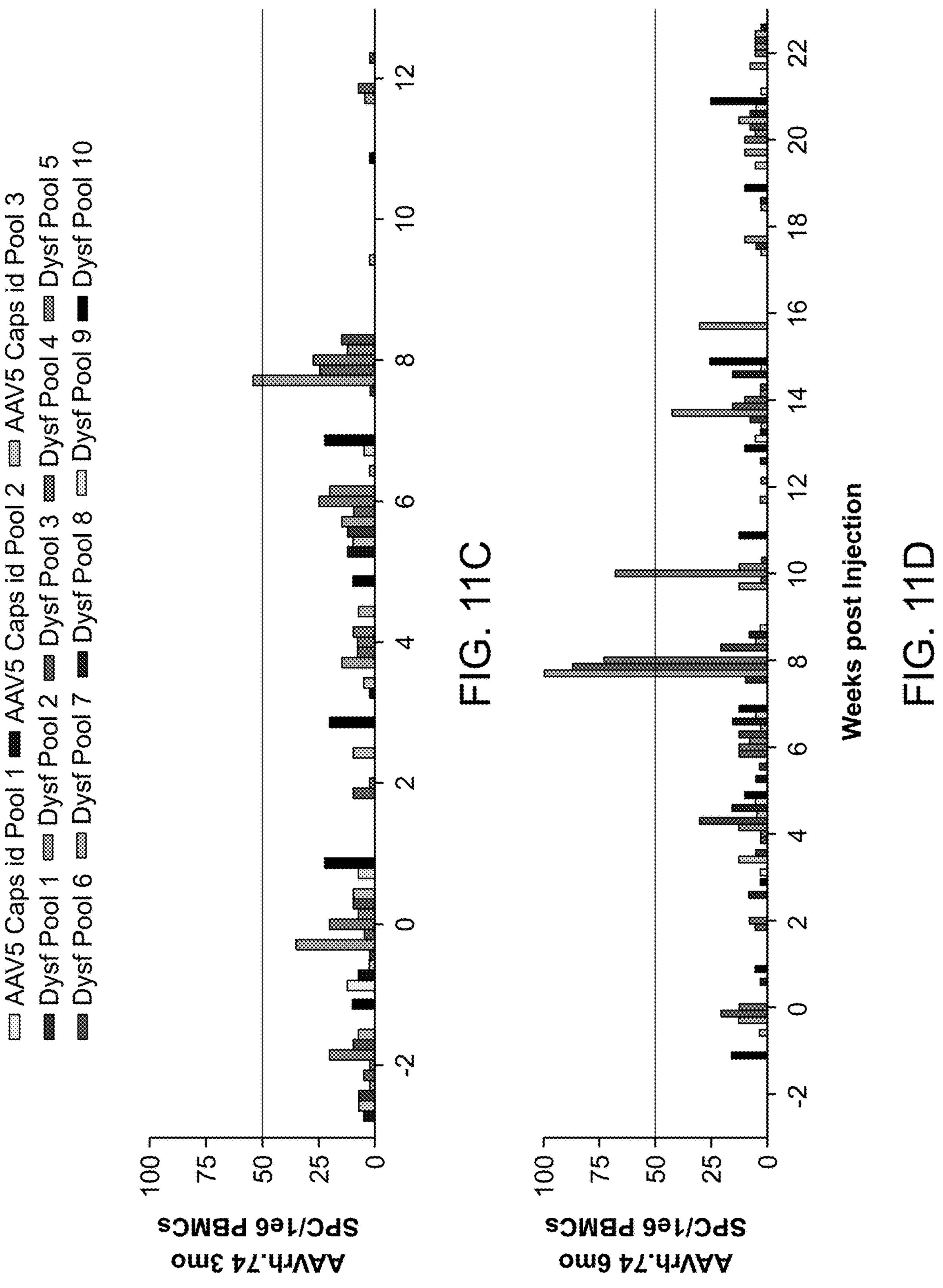

At study endpoint of 4 months, full necropsies were performed. The diaphragm was subjected to force measurements, the FDB muscle was tested for restoration of membrane repair, and muscles and organs were harvested for expression, vector biodistribution, and histopathology. At high dose, dysferlin expression was widespread in all muscles (FIGS. 7A and 7B), while low dose had low level variable expression. At 20 weeks, the BlaJ have a very mild phenotype histologically. There is a significant increase in central nuclei as a marker of regeneration compared to controls. Treated mice showed a significant decrease in central nucleation at high dose (FIG. 7B). The most affected muscle, the psoas demonstrated a reduction in fibrosis and inflammation upon treatment at high dose (6e12 vg) (FIG. 9). The force deficits in the diaphragm were restored at both high and low dose (FIG. 10A) and there was a dose dependent response in membrane repair in the FDB muscle (FIG. 10B).

Example 4: Safety and Efficacy of Full-Length Dysferlin Expression by AAV5 and Aavrh.74.Mhck7.Dysf.Dv Delivery in NHPs Methods: We treated 4 NHPs with AAV.MHCK7.DYSF.FLAG by intramuscular injection. 2 NHPs were treated with AAV5.MHCK7.DYSF and 2 were treated with AAVrh.74. MHCK7.DYSF.FLAG. Mirroring our clinical trial design, one animal was analyzed at 3 months and two at 6 months. Animals received baseline chemistries and immunological studies including ELISpot analysis to measure T cells against AAV5 and rh.74 capsid and dysferlin (FIGS. 11A-11D) and anti-AAV Ab titers (Table 9).

Peptide pools used to stimulate the PBMCs were designed to be 15 amino acids long, overlapping by 10 amino acids so as to capture all possible antigenic epitopes. Cells reacting to the peptides release interferon-γ, quantified as spots through an ELISpot assay. Spots per million cells were counted with 50 spots/$1\times10^6$ cells as the positive reaction threshold. No sustained immune response was observed. All animals had expression at study endpoint (FIG. 16A). These studies were repeated every two weeks for the entire study. At the study endpoint full necropsies were performed on the animals that in addition to gene expression studies included histopathology and biodistribution studies on vital organ tissues.

Figure 12A:
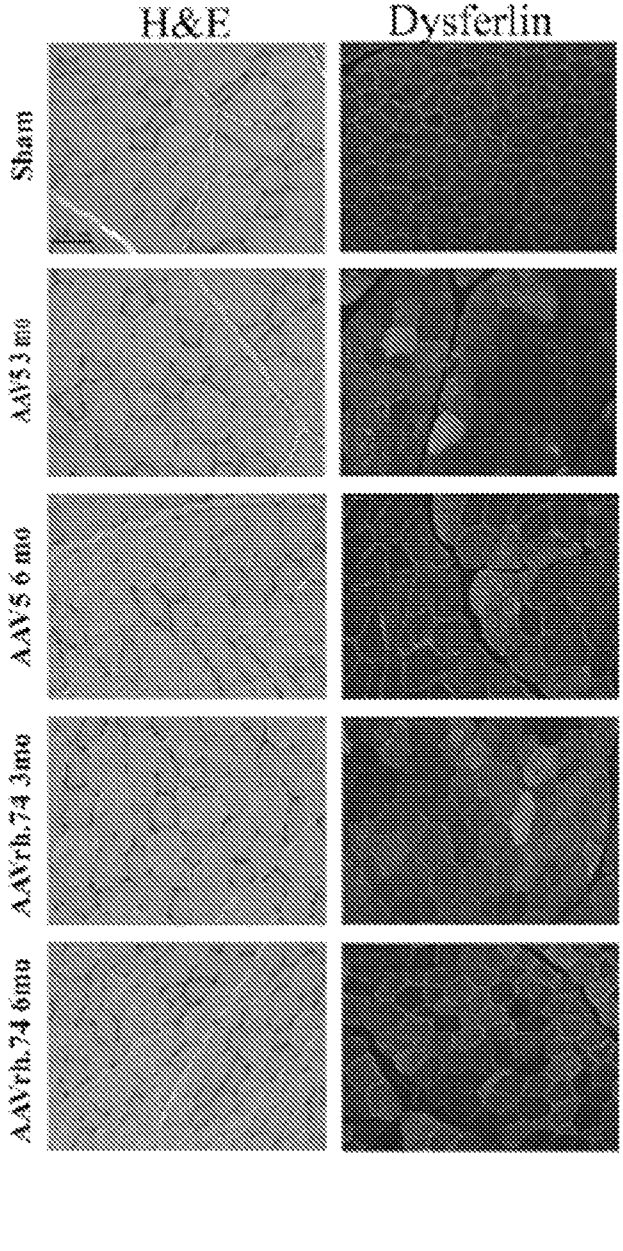
FIGS. 12A-12C show dysferlin expression in non-human primates.
Figure 12B:
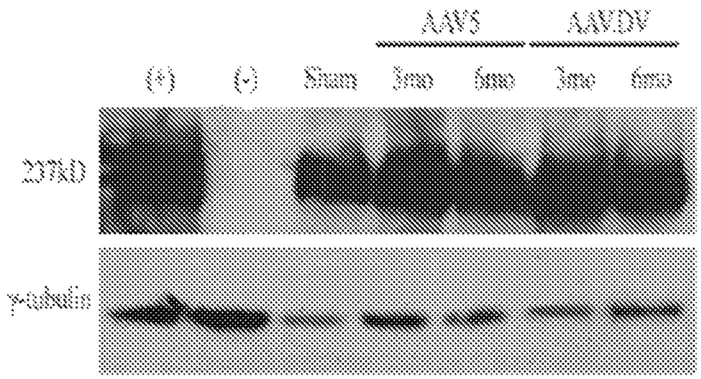
Figure 12C:
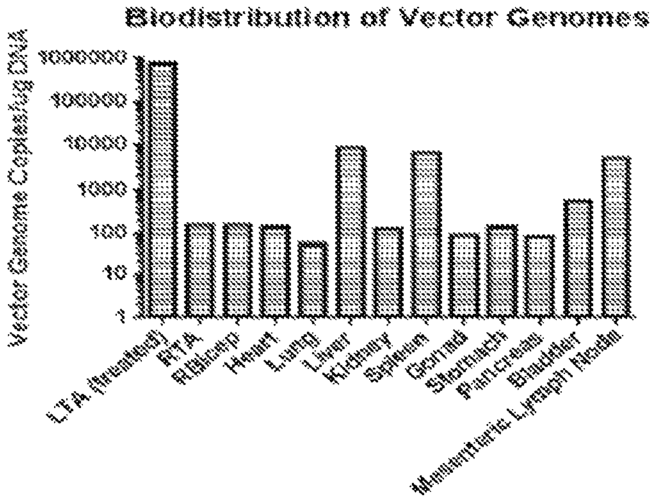
Figure 13:
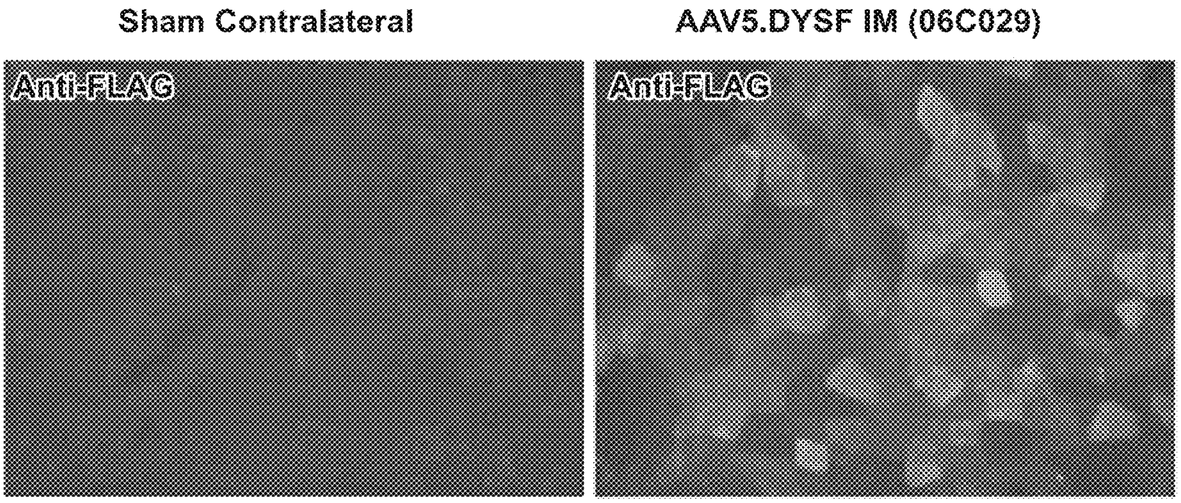
FIG. 13 demonstrates the use of anti-FLAG to confirm vector derived dysferlin expression. An N-terminal FLAG tag was used to discriminate between endogenous and AAV derived dysferlin.

Results: No observable toxicity was found. Applicants used anti-dysferlin antibody that does not distinguish between rhesus and human dysferlin to demonstrate overexpression of dysferlin (FIGS. 12A-12C). Anti-FLAG immune staining was also done to confirm vector derived dysferlin expression (FIG. 13). For AAV5.DYSF injected TAs, the muscles demonstrated 104.9% (3 mo) and 122.6% (6 mo) overexpression of dysferlin while AAVrh.74.DYSF.DV injected TAs had 122.0% (3 mo) and 115.2% (6 mo) overexpression as compared to the uninjected control. No toxicity was observed at the tissue level in the NHPs with a lack of inflammation or muscle fiber necrosis. Immunological assays did not show any aberrant responses to the capsid or transgene by ELISpot (FIGS. 11A-11D). In addition full complete blood count and chemistry panels showed no abnormal values in any of the macaques. As expected, anti-AAV antibody titers were elevated following gene transfer. Endpoint anti-AAVrh.74 titers were lower than those for anti-AAV5.

TABLE 9

Anti-AAV5 and Anti-AAVrh.74 antibodies following intramuscular injection in NHPs.

| Weeks Post | AAV5.hDYSF | | | AAVrh.74.DYSF.DV | |
|---|---|---|---|---|---|
| Injection | 06C011 | 06C029 | 07C019 | 10-158 | 10-172 |
| 0 | <5 | <5 | <5 | <5 | <5 |
| 2 | 1,600 | 6,400 | 6,400 | 400 | 400 |
| 4 | 51,200 | 51,200 | 51,200 | 800 | 800 |
| 6 | 51,200 | 102,400 | 102,400 | 800 | 200 |
| 8 | 51,200 | 204,800 | 102,400 | 800 | 800 |
| 10 | 51,200 | 102,400 | 51,200 | 1,600 | 1,600 |
| 12 | 51,200 | 204,800 | 102,400 | 1,600 | 800 |
| 14 | 51,200 | 204,800 | 51,200 | | 800 |
| 16 | 51,200 | 102,400 | | | 800 |
| 18 | 51,200 | 51,200 | | | 1,600 |
| 20 | 51,200 | 25,600 | | | 1,600 |
| 22 | 51,200 | 25,600 | | | 1,600 |
| 24 | 51,200 | 51,200 | | | 3,200 |

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A dual adeno-associated viral (AAV) vector system comprising:

(a) a first AAV vector, wherein the first AAV vector comprises a first recombinant polynucleotide comprising a fragment of a human dysferlin (hDYSF) gene, wherein the fragment consists of the nucleotide sequence of SEQ ID NO: 1; and (b) a second AAV vector, wherein the second AAV vector comprises a second recombinant polynucleotide comprising a fragment of a hDYSF gene, wherein the fragment consists of the nucleotide sequence of SEQ ID NO: 2.

2. The dual AAV vector system of claim 1, wherein the first and the second recombinant polynucleotides further comprise one or more additional polynucleotide sequences comprising a selection marker, an origin of replication (ORI), or an untranslated region (UTR).

3. A composition comprising the dual AAV vector system of claim 1 and a pharmaceutically acceptable carrier.

4. The dual AAV vector system according to claim 1, wherein the first recombinant polynucleotide comprises the nucleotide sequence of SEQ ID NO: 6, and wherein the second recombinant polynucleotide comprises the nucleotide sequence of SEQ ID NO: 8.

5. An adeno-associated viral (AAV) packaging system comprising:

(a) (i) a first plasmid comprising a first recombinant polynucleotide comprising a fragment of a human dysferlin (hDYSF) gene, wherein the fragment consists of the nucleotide sequence of SEQ ID NO: 1; and (ii) a second plasmid comprising a second recombinant polynucleotide comprising a fragment of a hDYSF gene, wherein the fragment consists of the nucleotide sequence of SEQ ID NO: 2;

(b) an adenovirus helper plasmid; and (c) a rep-cap plasmid.

6. A method for producing an adeno-associated viral (AAV) vector, comprising contacting a cell with the AAV packaging system of claim 5.

7. The method of claim 6, wherein the cell is a host cell.

8. A method for producing an adeno-associated viral (AAV) vector, comprising contacting a packaging cell line with the first plasmid or the second plasmid of claim 5, wherein the packaging cell line expresses an adeno-associated viral rep and cap genes.

9. A cell comprising the dual AAV vector system of claim 1.

10. A method of treating a dysferlinopathy, comprising administering to a subject in need thereof:

(a) an effective amount of a first recombinant polynucleotide, wherein the first recombinant polynucleotide comprises a fragment of a human dysferlin (hDYSF) gene, wherein the fragment consists of the nucleotide sequence of SEQ ID NO: 1; and (b) an effective amount of a second recombinant polynucleotide, wherein the second recombinant polynucleotide comprises a fragment of a hDYSF gene, wherein the fragment consists of the nucleotide sequence of SEQ ID NO: 2.

11. The method of claim 10, wherein the first recombinant polynucleotide and/or second recombinant polynucleotide is administered intramuscularly or intravenously.

12. The method of claim 10, wherein the first and second recombinant polynucleotides are administered simultaneously or sequentially.

13. A method of treating a dysferlinopathy, comprising administering to a subject in need thereof an effective amount of the AAV dual vector system of claim 1.

14. The AAV packaging system of claim 5, wherein the first plasmid comprising the first recombinant polynucleotide comprises the nucleotide sequence of SEQ ID NO: 18, and the second plasmid comprising the second recombinant polynucleotide comprises the nucleotide sequence of SEQ ID NO: 19.

15. The method of claim 6, further comprising culturing the cell to produce a population of transduced cells, collecting supernatant from the population of transduced cells, and subjecting the supernatant to one or more purification steps to produce a purified AAV vector sample.

* * * * *

SEQUENCE LISTING

<160> NUMBER OF SEQ ID NOS: 22

<210> SEQ ID NO 1
<211> LENGTH: 3340
<212> TYPE: DNA
<213> ORGANISM: Homo sapiens
<220> FEATURE:
<223> OTHER INFORMATION: 5' hDYSF DNA fragment v1

<400> SEQUENCE: 1

```
atgctgaggg tcttcatcct ctatgccgag aacgtccaca cacccgacac cgacatcagc     60

gatgcctact gctccgcggt gtttgcaggg gtgaagaaga gaaccaaagt catcaagaac    120

agcgtgaacc ctgtatggaa tgagggattt gaatgggacc tcaagggcat ccccctggac    180

cagggctctg agcttcatgt ggtggtcaaa gaccatgaga cgatggggag gaacaggttc    240

ctgggggaag ccaaggtccc actccgagag gtcctcgcca cccctagtct gtccgccagc    300

ttcaatgccc ccctgctgga caccaagaag cagcccacag ggcctcgct ggtcctgcag     360

gtgtcctaca caccgctgcc tggagctgtg cccctgttcc cgccccctac tcctctggag    420

ccctccccga ctctgcctga cctggatgta gtggcagaca caggaggaga ggaagacaca    480

gaggaccagg gactcactgg agatgaggcg gagccattcc tggatcaaag cggaggcccg    540

ggggctccca ccaccccaag gaaactacct tcacgtcctc cgccccacta ccccgggatc    600

aaaagaaagc gaagtgcgcc tacatctaga aagctgctgt cagacaaacc gcaggatttc    660

cagatcaggg tccaggtgat cgagggggcgc cagctgccgg gggtgaacat caagcctgtg   720

gtcaaggtta ccgctgcagg gcagaccaag cggacgcgga tccacaaggg aaacagccca    780

ctcttcaatg agactctttt cttcaacttg tttgactctc ctggggagct gtttgatgag    840

cccatcttta tcacggtggt agactctcgt tctctcagga cagatgctct cctcggggag    900

ttccggatgg acgtgggcac catttacaga gagccccggc acgcctatct caggaagtgg    960

ctgctgctct cagaccctga tgacttctct gctggggcca gaggctacct gaaaacaagc   1020

ctttgtgtgc tggggcctgg ggacgaagcg cctctggaga gaaaagaccc ctctgaagac   1080

aaggaggaca ttgaaagcaa cctgctccgg cccacaggcg tagccctgcg aggagcccac   1140

ttctgcctga aggtcttccg ggccgaggac ttgccgcaga tggacgatgc cgtgatggac   1200

aacgtgaaac agatctttgg cttcgagagt aacaagaaga acttggtgga cccctttgtg   1260

gaggtcagct ttgcggggaa aatgctgtgc agcaagatct tggagaagac ggccaacccct  1320

cagtggaacc agaacatcac actgcctgcc atgtttccct ccatgtgcga aaaaatgagg   1380

attcgtatca tagactggga ccgcctgact cacaatgaca tcgtggctac cacctacctg   1440

agtatgtcga aaatctctgc ccctggagga gaaatagaag aggagcctgc aggtgctgtc   1500

aagccttcga aagcctcaga cttggatgac tacctgggct tcctccccac ttttgggccc   1560

tgctacatca acctctatgg cagtcccaga gagttcacag gcttcccaga cccctacaca   1620

gagctcaaca caggcaaggg ggaaggtgtg gcttatcgtg gccggcttct gctctccctg   1680

gagaccaagc tggtggagca cagtgaacag aaggtggagg accttcctgc ggatgacatc   1740

ctccgggtgg agaagtacct taggaggcgc aagtactccc tgtttgcggc cttctactca   1800

gccaccatgc tgcaggatgt ggatgatgcc atccagtttg aggtcagcat cgggaactac   1860
```

gggaacaagt tcgacatgac ctgcctgccg ctggcctcca ccactcagta cagccgtgca 1920
gtctttgacg ggtgccacta ctactaccta ccctggggta acgtgaaacc tgtggtggtg 1980
ctgtcatcct actgggagga catcagccat agaatcgaga ctcagaacca gctgcttggg 2040
attgctgacc ggctggaagc tggcctggag caggtccacc tggccctgaa ggcgcagtgc 2100
tccacggagg acgtggactc gctggtggct cagctgacgg atgagctcat cgcaggctgc 2160
agccagcctc tgggtgacat ccatgagaca ccctctgcca cccacctgga ccagtacctg 2220
taccagctgc gcacccatca cctgagccaa atcactgagg ctgccctggc cctgaagctc 2280
ggccacagtg agctccctgc agctctggag caggcggagg actggctcct gcgtctgcgt 2340
gccctggcag aggagcccca gaacagcctg ccggacatcg tcatctggat gctgcaggga 2400
gacaagcgtg tggcatacca gcgggtgccc gcccaccaag tcctcttctc ccggcggggt 2460
gccaactact gtggcaagaa ttgtgggaag ctacagacaa tctttctgaa atatccgatg 2520
gagaaggtgc ctggcgcccg gatgccagtg cagatacggg tcaagctgtg gtttgggctc 2580
tctgtggatg agaaggagtt caaccagttt gctgagggga agctgtctgt ctttgctgaa 2640
acctatgaga acgagactaa gttggccctt gttgggaact ggggcacaac gggcctcacc 2700
taccccaagt tttctgacgt cacgggcaag atcaagctac ccaaggacag cttccgcccc 2760
tcggccggct ggacctgggc tggagattgg ttcgtgtgtc cggagaagac tctgctccat 2820
gacatggacg ccggtcacct gagcttcgtg gaagaggtgt ttgagaacca gacccggctt 2880
cccggaggcc agtggatcta catgagtgac aactacaccg atgtgaacgg ggagaaggtg 2940
cttcccaagg atgacattga gtgcccactg ggctggaagt gggaagatga ggaatggtcc 3000
acagacctca accgggctgt cgatgagcaa ggctgggagt atagcatcac catccccccg 3060
gagcggaagc cgaagcactg ggtccctgct gagaagatgt actacacaca ccgacggcgg 3120
cgctgggtgc gcctgcgcag gagggatctc agccaaatgg aagcactgaa aaggcacagg 3180
caggcggagg cggagggcga gggctgggag tacgcctctc tttttggctg gaagttccac 3240
ctcgagtacc gcaagacaga tgccttccgc cgccgccgct ggcgccgtcg catggagcca 3300
ctggagaaga cggggcctgc agctgtgttt gcccttgagg 3340

<210> SEQ ID NO 2
<211> LENGTH: 3866
<212> TYPE: DNA
<213> ORGANISM: Homo sapiens
<220> FEATURE:
<223> OTHER INFORMATION: 3' hDYSF DNA fragment v1

<400> SEQUENCE: 2
tcgtcatctg gatgctgcag ggagacaagc gtgtggcata ccagcgggtg cccgcccacc 60
aagtcctctt ctcccggcgg ggtgccaact actgtggcaa gaattgtggg aagctacaga 120
caatctttct gaaatatccg atggagaagg tgcctggcgc ccggatgcca gtgcagatac 180
gggtcaagct gtggtttggg ctctctgtgg atgagaagga gttcaaccag tttgctgagg 240
ggaagctgtc tgtctttgct gaaacctatg agaacgagac taagttggcc cttgttggga 300
actggggcac aacgggcctc acctacccca agttttctga cgtcacgggc aagatcaagc 360
tacccaagga cagcttccgc ccctcggccg gctggacctg ggctggagat tggttcgtgt 420
gtccggagaa gactctgctc catgacatgg acgccggtca cctgagcttc gtggaagagg 480
tgtttgagaa ccagacccgg cttcccggag gccagtggat ctacatgagt gacaactaca 540
ccgatgtgaa cggggagaag gtgcttccca aggatgacat tgagtgccca ctgggctgga 600
agtgggaaga tgaggaatgg tccacagacc tcaaccgggc tgtcgatgag caaggctggg 660
agtatagcat caccatcccc ccggagcgga agccgaagca ctgggtccct gctgagaaga 720
tgtactacac acaccgacgg cggcgctggg tgcgcctgcg caggagggat ctcagccaaa 780
tggaagcact gaaaaggcac aggcaggcgg aggcggaggg cgagggctgg gagtacgcct 840
ctctttttgg ctggaagttc cacctcgagt accgcaagac agatgccttc cgccgccgcc 900
gctggcgccg tcgcatggag ccactggaga agacggggcc tgcagctgtg tttgcccttg 960
agggggccct gggcggcgtg atggatgaca agagtgaaga ttccatgtcc gtctccacct 1020
tgagcttcgg tgtgaacaga cccacgattt cctgcatatt cgactatggg aaccgctacc 1080
atctacgctg ctacatgtac caggcccggg acctggctgc gatggacaag gactcttttt 1140
ctgatcccta tgccatcgtc tccttcctgc accagagcca gaagacggtg gtggtgaaga 1200
acacccttaa ccccacctgg gaccagacgc tcatcttcta cgagatcgag atctttggcg 1260
agccggccac agttgctgag caaccgccca gcattgtggt ggagctgtac gaccatgaca 1320
cttatggtgc agacgagttt atgggtcgct gcatctgtca accgagtctg gaacggatgc 1380
cacggctggc ctggttccca ctgacgaggg gcagccagcc gtcgggggag ctgctggcct 1440
cttttgagct catccagaga gagaagccgg ccatccacca tattcctggt tttgaggtgc 1500
aggagacatc aaggatcctg gatgagtctg aggacacaga cctgccctac ccaccacccc 1560
agagggaggc caacatctac atggttcctc agaacatcaa gccagcgctc cagcgtaccg 1620
ccatcgagat cctggcatgg ggcctgcgga acatgaagag ttaccagctg gccaacatct 1680
cctcccccag cctcgtggta gagtgtgggg gccagacggt gcagtcctgt gtcatcagga 1740
acctccggaa gaaccccaac tttgacatct gcaccctctt catggaagtg atgctgccca 1800
gggaggagct ctactgcccc cccatcaccg tcaaggtcat cgataaccgc cagtttggcc 1860
gccggcctgt ggtgggccag tgtaccatcc gctccctgga gagcttcctg tgtgacccct 1920
actcggcgga gagtccatcc ccacagggtg gcccagacga tgtgagccta ctcagtcctg 1980
gggaagacgt gctcatcgac attgatgaca aggagcccct catccccatc caggaggaag 2040
agttcatcga ttggtggagc aaattctttg cctccatagg ggagagggaa aagtgcggct 2100
cctacctgga gaaggatttt gacaccctga aggtctatga cacacagctg gagaatgtgg 2160
aggcctttga gggcctgtct gacttttgta acaccttcaa gctgtaccgg ggcaagacgc 2220
aggaggagac agaagatcca tctgtgattg gtgaatttaa gggcctcttc aaaatttatc 2280
ccctcccaga agacccagcc atccccatgc ccccaagaca gttccaccag ctggccgccc 2340
agggacccca ggagtgcttg gtccgtatct acattgtccg agcatttggc ctgcagccca 2400
aggaccccaa tggaaagtgt gatccttaca tcaagatctc catagggaag aaatcagtga 2460
gtgaccagga taactacatc ccctgcacgc tggagcccgt atttggaaag atgttcgagc 2520
tgacctgcac tctgcctctg gagaaggacc taaagatcac tctctatgac tatgacctcc 2580
tctccaagga cgaaaagatc ggtgagacgg tcgtcgacct ggagaacagg ctgctgtcca 2640
agtttggggc tcgctgtgga ctcccacaga cctactgtgt ctctggaccg aaccagtggc 2700
gggaccagct ccgcccctcc cagctcctcc acctcttctg ccagcagcat agagtcaagg 2760
cacctgtgta ccggacagac cgtgtaatgt ttcaggataa agaatattcc attgaagaga 2820
tagaggctgg caggatccca aacccacacc tgggcccagt ggaggagcgt ctggctctgc 2880
atgtgcttca gcagcagggc ctggtcccgg agcacgtgga gtcacggccc ctctacagcc 2940

```
ccctgcagcc agacatcgag caggggaagc tgcagatgtg ggtcgaccta tttccgaagg   3000
ccctggggcg gcctggacct cccttcaaca tcaccccacg gagagccaga aggtttttcc   3060
tgcgttgtat tatctggaat accagagatg tgatcctgga tgacctgagc ctcacggggg   3120
agaagatgag cgacatttat gtgaaaggtt ggatgattgg ctttgaagaa cacaagcaaa   3180
agacagacgt gcattatcgt tccctgggag gtgaaggcaa cttcaactgg aggttcattt   3240
tccccttcga ctacctgcca gctgagcaag tctgtaccat tgccaagaag gatgccttct   3300
ggaggctgga caagactgag agcaaaatcc cagcacgagt ggtgttccag atctgggaca   3360
atgacaagtt ctcctttgat gattttctgg gctccctgca gctcgatctc aaccgcatgc   3420
ccaagccagc caagacagcc aagaagtgct ccttggacca gctggatgat gctttccacc   3480
cagaatggtt tgtgtccctt tttgagcaga aaacagtgaa gggctggtgg ccctgtgtag   3540
cagaagaggg tgagaagaaa atactggcgg gcaagctgga aatgaccttg gagattgtag   3600
cagagagtga gcatgaggag cggcctgctg gccagggccg ggatgagccc aacatgaacc   3660
ctaagcttga ggacccaagg cgccccgaca cctccttcct gtggtttacc tccccataca   3720
agaccatgaa gttcatcctg tggcggcgtt tccggtgggc catcatcctc ttcatcatcc   3780
tcttcatcct gctgctgttc ctggccatct tcatctacgc cttcccgaac tatgctgcca   3840
tgaagctggt gaagcccttc agctga                                        3866
```

<210> SEQ ID NO 3
<211> LENGTH: 128
<212> TYPE: DNA
<213> ORGANISM: Adeno-associated virus 2
<220> FEATURE:
<223> OTHER INFORMATION: ITR

<400> SEQUENCE: 3

```
gcgcgctcgc tcgctcactg aggccgcccg ggcaaagccc gggcgtcggg cgacctttgg     60
tcgcccggcc tcagtgagcg agcgagcgcg cagagaggga gtggccaact ccatcactag    120
gggttcct                                                             128
```

<210> SEQ ID NO 4
<211> LENGTH: 792
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: promoter

<400> SEQUENCE: 4

```
aagcttgcat gtctaagcta gacccttcag attaaaaata actgaggtaa gggcctgggt     60
aggggaggtg gtgtgagacg ctcctgtctc tcctctatct gcccatcggc cctttgggga    120
ggaggaatgt gcccaaggac taaaaaaagg ccatggagcc agaggggcga gggcaacaga    180
cctttcatgg gcaaaccttg gggccctgct gtctagcatg ccccactacg ggtctaggct    240
gcccatgtaa ggaggcaagg cctggggaca cccgagatgc ctggttataa ttaacccaga    300
catgtggctg cccccccccc cccaacacct gctgcctcta aaaataaccc tgtccctggt    360
ggatcccctg catgcgaaga tcttcgaaca aggctgtggg ggactgaggg caggctgtaa    420
caggcttggg ggccagggct tatacgtgcc tgggactccc aaagtattac tgttccatgt    480
tcccggcgaa gggccagctg tcccccgcca gctagactca gcacttagtt taggaaccag    540
```

tgagcaagtc agcccttggg gcagcccata caaggccatg ggctgggca agctgcacgc 600 ctgggtccgg ggtgggcacg gtgcccgggc aacgagctga aagctcatct gctctcaggg 660
gcccctccct ggggacagcc cctcctggct agtcacaccc tgtaggctcc tctatataac 720
ccaggggcac aggggctgcc ctcattctac caccacctcc acagcacaga cagacactca 780
ggagcagcca gc 792

<210> SEQ ID NO 5
<211> LENGTH: 148
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Intron

<400> SEQUENCE: 5
aggtaagttt agtctttttg tcttttattt caggtcccgg atccggtggt ggtgcaaatc 60
aaagaactgc tcctcagtgg atgttgcctt tacttctagg cctgtacgga agtgttactt 120
ctgctctaaa agctgcggaa ttgtaccc 148

<210> SEQ ID NO 6
<211> LENGTH: 4689
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: DYSF F5' Expression Cassette v1

<400> SEQUENCE: 6
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctctaga gtttaagctt gcatgtctaa 180
gctagaccct tcagattaaa aataactgag gtaagggcct gggtagggga ggtggtgtga 240
gacgctcctg tctctcctct atctgcccat cggccctttg gggaggagga atgtgcccaa 300
ggactaaaaa aaggccatgg agccagaggg gcgagggcaa cagacctttc atgggcaaac 360
cttggggccc tgctgtctag catgccccac tacgggtcta ggctgcccat gtaaggaggc 420
aaggcctggg gacacccgag atgcctggtt ataattaacc cagacatgtg gctgcccccc 480 ccccccaac acctgctgcc tctaaaaata accctgtccc tggtggatcc cctgcatgcg 540
aagatcttcg aacaaggctg tgggggactg agggcaggct gtaacaggct tgggggccag 600
ggcttatacg tgcctgggac tcccaaagta ttactgttcc atgttcccgg cgaagggcca 660
gctgtccccc gccagctaga ctcagcactt agtttaggaa ccagtgagca agtcagccct 720
tggggcagcc catacaaggc catggggctg ggcaagctgc acgcctgggt ccggggtggg 780
cacggtgccc gggcaacgag ctgaaagctc atctgctctc aggggcccct ccctggggac 840
agcccctcct ggctagtcac accctgtagg ctcctctata taacccaggg gcacaggggc 900
tgccctcatt ctaccaccac ctccacagca cagacagaca ctcaggagca gccagcggcg 960
cgcccaggta agtttagtct tttgtcttt tatttcaggt cccggatccg gtggtggtgc 1020
aaatcaaaga actgctcctc agtggatgtt gcctttactt ctaggcctgt acggaagtgt 1080
tacttctgct ctaaaagctg cggaattgta cccgcggccg cggctagcca ccatgctgag 1140

```
ggtcttcatc ctctatgccg agaacgtcca cacacccgac accgacatca gcgatgccta   1200
ctgctccgcg gtgtttgcag ggtgaagaa gagaaccaaa gtcatcaaga acagcgtgaa   1260
ccctgtatgg aatgagggat ttgaatggga cctcaagggc atccccctgg accagggctc   1320
tgagcttcat gtggtggtca aagaccatga gacgatgggg aggaacaggt tcctgggga   1380
agccaaggtc ccactccgag aggtcctcgc cacccctagt ctgtccgcca gcttcaatgc   1440
ccccctgctg gacaccaaga agcagcccac aggggcctcg ctggtcctgc aggtgtccta   1500
cacaccgctg cctggagctg tgcccctgtt cccgcccct actcctctgg agccctcccc   1560
gactctgcct gacctggatg tagtggcaga cacaggagga gaggaagaca cagaggacca   1620
gggactcact ggagatgagg cggagccatt cctggatcaa agcggaggcc cgggggctcc   1680
caccaccca aggaaactac cttcacgtcc tccgccccac taccccggga tcaaaagaaa   1740
gcgaagtgcg cctacatcta gaaagctgct gtcagacaaa ccgcaggatt tccagatcag   1800
ggtccaggtg atcgaggggc gccagctgcc gggggtgaac atcaagcctg tggtcaaggt   1860
taccgctgca gggcagacca agcggacgcg gatccacaag ggaaacagcc cactcttcaa   1920
tgagactctt ttcttcaact tgtttgactc tcctggggag ctgtttgatg agcccatctt   1980
tatcacggtg gtagactctc gttctctcag gacagatgct ctcctcgggg agttccggat   2040
ggacgtgggc accatttaca gagagccccg gcacgcctat ctcaggaagt ggctgctgct   2100
ctcagaccct gatgacttct ctgctggggc cagaggctac ctgaaaacaa gcctttgtgt   2160
gctggggcct ggggacgaag cgcctctgga gagaaaagac ccctctgaag acaaggagga   2220
cattgaaagc aacctgctcc ggcccacagg cgtagccctg cgaggagccc acttctgcct   2280
gaaggtcttc cgggccgagg acttgccgca gatggacgat gccgtgatgg acaacgtgaa   2340
acagatcttt ggcttcgaga gtaacaagaa gaacttggtg gacccctttg tggaggtcag   2400
ctttgcgggg aaaatgctgt gcagcaagat cttggagaag acggccaacc ctcagtggaa   2460
ccagaacatc acactgcctg ccatgtttcc ctccatgtgc gaaaaaatga ggattcgtat   2520
catagactgg gaccgcctga ctcacaatga catcgtggct accacctacc tgagtatgtc   2580
gaaaatctct gcccctggag gagaaataga agaggagcct gcaggtgctg tcaagccttc   2640
gaaagcctca gacttggatg actacctggg cttcctcccc acttttgggc cctgctacat   2700
caacctctat ggcagtccca gagagttcac aggcttccca gacccctaca cagagctcaa   2760
cacaggcaag gggaaggtg tggcttatcg tggccggctt ctgctctccc tggagaccaa   2820
gctggtggag cacagtgaac agaaggtgga ggaccttcct gcggatgaca tcctccgggt   2880
ggagaagtac cttaggaggc gcaagtactc cctgtttgcg gccttctact cagccaccat   2940
gctgcaggat gtggatgatg ccatccagtt tgaggtcagc atcgggaact acgggaacaa   3000
gttcgacatg acctgcctgc cgctggcctc caccactcag tacagccgtg cagtctttga   3060
cgggtgccac tactactacc taccctgggg taacgtgaaa cctgtggtgg tgctgtcatc   3120
ctactgggag gacatcagcc atagaatcga gactcagaac cagctgcttg ggattgctga   3180
ccggctggaa gctggcctgg agcaggtcca cctggccctg aaggcgcagt gctccacgga   3240
ggacgtggac tcgctggtgg ctcagctgac ggatgagctc atcgcaggct gcagccagcc   3300
tctgggtgac atccatgaga caccctctgc cacccacctg gaccagtacc tgtaccagct   3360
gcgcacccat cacctgagcc aaatcactga ggctgccctg gccctgaagc tcggccacag   3420
tgagctccct gcagctctgg agcaggcgga ggactggctc ctgcgtctgc gtgccctggc   3480
```

agaggagccc cagaacagcc tgccggacat cgtcatctgg atgctgcagg gagacaagcg 3540
tgtggcatac cagcgggtgc ccgcccacca agtcctcttc tcccggcggg gtgccaacta 3600
ctgtggcaag aattgtggga agctacagac aatctttctg aaatatccga tggagaaggt 3660
gcctggcgcc cggatgccag tgcagatacg ggtcaagctg tggtttgggc tctctgtgga 3720
tgagaaggag ttcaaccagt ttgctgaggg gaagctgtct gtctttgctg aaacctatga 3780
gaacgagact aagttggccc ttgttgggaa ctggggcaca acgggcctca cctaccccaa 3840
gttttctgac gtcacgggca agatcaagct acccaaggac agcttccgcc cctcggccgg 3900
ctggacctgg gctggagatt ggttcgtgtg tccggagaag actctgctcc atgacatgga 3960
cgccggtcac ctgagcttcg tggaagaggt gtttgagaac cagacccggc ttcccggagg 4020
ccagtggatc tacatgagtg acaactacac cgatgtgaac ggggagaagg tgcttcccaa 4080
ggatgacatt gagtgcccac tgggctggaa gtgggaagat gaggaatggt ccacagacct 4140
caaccgggct gtcgatgagc aaggctggga gtatagcatc accatccccc cggagcggaa 4200
gccgaagcac tgggtccctg ctgagaagat gtactacaca caccgacggc ggcgctgggt 4260
gcgcctgcgc aggagggatc tcagccaaat ggaagcactg aaaaggcaca ggcaggcgga 4320
ggcggagggc gagggctggg agtacgcctc tctttttggc tggaagttcc acctcgagta 4380
ccgcaagaca gatgccttcc gccgccgccg ctggcgccgt cgcatggagc cactggagaa 4440
gacggggcct gcagctgtgt ttgcccttga gggcggccgc aataaaagat ctttattttc 4500
attagatctg tgtgttggtt ttttgtgtgt ctagagcatg gcgggttaat cattaactac 4560
aaggaacccc tagtgatgga gttggccact ccctctctgc gcgctcgctc gctcactgag 4620
gccgggcgac caaaggtcgc ccgacgcccg ggctttgccc gggcggcctc agtgagcgag 4680
cgagcgcgc 4689

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: PolyA Signal

<400> SEQUENCE: 7
aataaaagat ctttattttc attagatctg tgtgttggtt ttttgtgtg 49

<210> SEQ ID NO 8
<211> LENGTH: 4592
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: DYSF F3' Expression Cassette v1

<400> SEQUENCE: 8
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtagc catgctctgg 180
tcgactctag agttttcgtc atctggatgc tgcagggaga caagcgtgtg gcataccagc 240
gggtgcccgc ccaccaagtc ctcttctccc ggcggggtgc caactactgt ggcaagaatt 300

```
gtgggaagct acagacaatc tttctgaaat atccgatgga gaaggtgcct ggcgcccgga    360
tgccagtgca gatacgggtc aagctgtggt ttgggctctc tgtggatgag aaggagttca    420
accagtttgc tgaggggaag ctgtctgtct ttgctgaaac ctatgagaac gagactaagt    480
tggcccttgt tgggaactgg ggcacaacgg gcctcaccta ccccaagttt tctgacgtca    540
cgggcaagat caagctaccc aaggacagct tccgcccctc ggccggctgg acctgggctg    600
gagattggtt cgtgtgtccg gagaagactc tgctccatga catggacgcc ggtcacctga    660
gcttcgtgga agaggtgttt gagaaccaga cccggcttcc cggaggccag tggatctaca    720
tgagtgacaa ctacaccgat gtgaacgggg agaaggtgct tcccaaggat gacattgagt    780
gcccactggg ctggaagtgg gaagatgagg aatggtccac agacctcaac cgggctgtcg    840
atgagcaagg ctgggagtat agcatcacca tccccccgga gcggaagccg aagcactggg    900
tccctgctga gaagatgtac tacacacacc gacggcggcg ctgggtgcgc ctgcgcagga    960
gggatctcag ccaaatggaa gcactgaaaa ggcacaggca ggcggaggcg gagggcgagg   1020
gctgggagta cgcctctctt tttggctgga agttccacct cgagtaccgc aagacagatg   1080
ccttccgccg ccgccgctgg cgccgtcgca tggagccact ggagaagacg gggcctgcag   1140
ctgtgtttgc ccttgagggg gccctgggcg gcgtgatgga tgacaagagt gaagattcca   1200
tgtccgtctc caccttgagc ttcggtgtga acagacccac gatttcctgc atattcgact   1260
atgggaaccg ctaccatcta cgctgctaca tgtaccaggc ccgggacctg gctgcgatgg   1320
acaaggactc tttttctgat ccctatgcca tcgtctcctt cctgcaccag agccagaaga   1380
cggtggtggt gaagaacacc cttaacccca cctgggacca gacgctcatc ttctacgaga   1440
tcgagatctt tggcgagccg gccacagttg ctgagcaacc gcccagcatt gtggtggagc   1500
tgtacgacca tgacacttat ggtgcagacg agtttatggg tcgctgcatc tgtcaaccga   1560
gtctggaacg gatgccacgg ctggcctggt tcccactgac gaggggcagc cagccgtcgg   1620
gggagctgct ggcctctttt gagctcatcc agagagagaa gccggccatc caccatattc   1680
ctggttttga ggtgcaggag acatcaagga tcctggatga gtctgaggac acagacctgc   1740
cctacccacc accccagagg gaggccaaca tctacatggt tcctcagaac atcaagccag   1800
cgctccagcg taccgccatc gagatcctgg catggggcct gcggaacatg aagagttacc   1860
agctggccaa catctcctcc cccagcctcg tggtagagtg tgggggccag acggtgcagt   1920
cctgtgtcat caggaacctc cggaagaacc ccaactttga catctgcacc ctcttcatgg   1980
aagtgatgct gcccagggag gagctctact gcccccccat caccgtcaag gtcatcgata   2040
accgccagtt tggccgccgg cctgtggtgg gccagtgtac catccgctcc ctggagagct   2100
tcctgtgtga cccctactcg gcggagagtc catccccaca gggtggccca gacgatgtga   2160
gcctactcag tcctggggaa gacgtgctca tcgacattga tgacaaggag cccctcatcc   2220
ccatccagga ggaagagttc atcgattggt ggagcaaatt ctttgcctcc ataggggaga   2280
gggaaaagtg cggctcctac ctggagaagg attttgacac cctgaaggtc tatgacacac   2340
agctggagaa tgtggaggcc tttgagggcc tgtctgactt ttgtaacacc ttcaagctgt   2400
accggggcaa gacgcaggag gagacagaag atccatctgt gattggtgaa tttaagggcc   2460
tcttcaaaat ttatcccctc ccagaagacc cagccatccc catgccccca agacagttcc   2520
accagctggc cgcccaggga ccccaggagt gcttggtccg tatctacatt gtccgagcat   2580
ttggcctgca gcccaaggac cccaatggaa agtgtgatcc ttacatcaag atctccatag   2640
```

```
ggaagaaatc agtgagtgac caggataact acatcccctg cacgctggag cccgtatttg   2700
gaaagatgtt cgagctgacc tgcactctgc ctctggagaa ggacctaaag atcactctct   2760
atgactatga cctcctctcc aaggacgaaa agatcggtga gacggtcgtc gacctggaga   2820
acaggctgct gtccaagttt ggggctcgct gtggactccc acagacctac tgtgtctctg   2880
gaccgaacca gtggcgggac cagctccgcc cctcccagct cctccacctc ttctgccagc   2940
agcatagagt caaggcacct gtgtaccgga cagaccgtgt aatgtttcag gataaagaat   3000
attccattga agagatagag gctggcagga tcccaaaccc acacctgggc ccagtggagg   3060
agcgtctggc tctgcatgtg cttcagcagc agggcctggt cccggagcac gtggagtcac   3120
ggcccctcta cagccccctg cagccagaca tcgagcaggg gaagctgcag atgtgggtcg   3180
acctatttcc gaaggccctg gggcggcctg gacctccctt caacatcacc ccacggagag   3240
ccagaaggtt tttcctgcgt tgtattatct ggaataccag agatgtgatc ctggatgacc   3300
tgagcctcac gggggagaag atgagcgaca tttatgtgaa aggttggatg attggctttg   3360
aagaacacaa gcaaaagaca gacgtgcatt atcgttccct gggaggtgaa ggcaacttca   3420
actggaggtt cattttcccc ttcgactacc tgccagctga gcaagtctgt accattgcca   3480
agaaggatgc cttctggagg ctggacaaga ctgagagcaa aatcccagca cgagtggtgt   3540
tccagatctg ggacaatgac aagttctcct ttgatgattt tctgggctcc ctgcagctcg   3600
atctcaaccg catgcccaag ccagccaaga cagccaagaa gtgctccttg gaccagctgg   3660
atgatgcttt ccacccagaa tggtttgtgt cccttttga gcagaaaaca gtgaagggct    3720
ggtggccctg tgtagcagaa gagggtgaga agaaaatact ggcgggcaag ctggaaatga   3780
ccttggagat tgtagcagag agtgagcatg aggagcggcc tgctggccag ggccgggatg   3840
agcccaacat gaaccctaag cttgaggacc caaggcgccc cgacacctcc ttcctgtggt   3900
ttacctcccc atacaagacc atgaagttca tcctgtggcg gcgtttccgg tgggccatca   3960
tcctcttcat catcctcttc atcctgctgc tgttcctggc catcttcatc tacgccttcc   4020
cgaactatgc tgccatgaag ctggtgaagc ccttcagctg aggactctcc tgccctgtag   4080
aaggggccgt ggggtcccct ccagcatggg actggcctgc ctcctccgcc cagctcggcg   4140
agctcctcca gacctcctag gcctgattgt cctgccaggg tgggcagaca gacagatgga   4200
ccggcccaca ctcccagagt tgctaacatg gagctctgag atcaccccac ttccatcatt   4260
tccttctccc ccaacccaac gctttttgg atcagctcag acatatttca gtataaaaca    4320
gttggaacca caaaaaaaaa aaaaaaaagt cgacgcggcc gcaataaaag atctttattt   4380
tcattagatc tgtgtgttgg tttttgtgt gtctagagca tggctacgta gataagtagc    4440
atggcgggtt aatcattaac tacaaggaac ccctagtgat ggagttggcc actccctctc   4500
tgcgcgctcg ctcgctcact gaggccgggc gaccaaaggt cgcccgacgc ccgggctttg   4560
cccgggcggc ctcagtgagc gagcgagcgc gc                                 4592
```

<210> SEQ ID NO 9
<211> LENGTH: 1113
<212> TYPE: PRT
<213> ORGANISM: Homo sapiens
<220> FEATURE:
<223> OTHER INFORMATION: 5' hDYSF protein fragment

<400> SEQUENCE: 9

```
Met Leu Arg Val Phe Ile Leu Tyr Ala Glu Asn Val His Thr Pro Asp
1               5                   10                  15
```

-continued

```
Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu
    50                  55                  60

Leu His Val Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Pro Thr Pro Leu Glu Pro Ser Pro Thr
    130                 135                 140

Leu Pro Asp Leu Asp Val Val Ala Asp Thr Gly Gly Glu Glu Asp Thr
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Asp Phe Gln Ile Arg Val
    210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
        275                 280                 285

Ser Arg Ser Leu Arg Thr Asp Ala Leu Leu Gly Glu Phe Arg Met Asp
    290                 295                 300

Val Gly Thr Ile Tyr Arg Glu Pro Arg His Ala Tyr Leu Arg Lys Trp
305                 310                 315                 320

Leu Leu Leu Ser Asp Pro Asp Asp Phe Ser Ala Gly Ala Arg Gly Tyr
                325                 330                 335

Leu Lys Thr Ser Leu Cys Val Leu Gly Pro Gly Asp Glu Ala Pro Leu
            340                 345                 350

Glu Arg Lys Asp Pro Ser Glu Asp Lys Glu Asp Ile Glu Ser Asn Leu
        355                 360                 365

Leu Arg Pro Thr Gly Val Ala Leu Arg Gly Ala His Phe Cys Leu Lys
    370                 375                 380

Val Phe Arg Ala Glu Asp Leu Pro Gln Met Asp Asp Ala Val Met Asp
385                 390                 395                 400

Asn Val Lys Gln Ile Phe Gly Phe Glu Ser Asn Lys Lys Asn Leu Val
                405                 410                 415

Asp Pro Phe Val Glu Val Ser Phe Ala Gly Lys Met Leu Cys Ser Lys
            420                 425                 430

Ile Leu Glu Lys Thr Ala Asn Pro Gln Trp Asn Gln Asn Ile Thr Leu
```

```
        435                 440                 445

Pro Ala Met Phe Pro Ser Met Cys Glu Lys Met Arg Ile Arg Ile Ile
    450                 455                 460

Asp Trp Asp Arg Leu Thr His Asn Asp Ile Val Ala Thr Thr Tyr Leu
465                 470                 475                 480

Ser Met Ser Lys Ile Ser Ala Pro Gly Gly Glu Ile Glu Glu Glu Pro
                485                 490                 495

Ala Gly Ala Val Lys Pro Ser Lys Ala Ser Asp Leu Asp Asp Tyr Leu
            500                 505                 510

Gly Phe Leu Pro Thr Phe Gly Pro Cys Tyr Ile Asn Leu Tyr Gly Ser
        515                 520                 525

Pro Arg Glu Phe Thr Gly Phe Pro Asp Pro Tyr Thr Glu Leu Asn Thr
    530                 535                 540

Gly Lys Gly Glu Gly Val Ala Tyr Arg Gly Arg Leu Leu Leu Ser Leu
545                 550                 555                 560

Glu Thr Lys Leu Val Glu His Ser Glu Gln Lys Val Glu Asp Leu Pro
                565                 570                 575

Ala Asp Asp Ile Leu Arg Val Glu Lys Tyr Leu Arg Arg Arg Lys Tyr
            580                 585                 590

Ser Leu Phe Ala Ala Phe Tyr Ser Ala Thr Met Leu Gln Asp Val Asp
        595                 600                 605

Asp Ala Ile Gln Phe Glu Val Ser Ile Gly Asn Tyr Gly Asn Lys Phe
    610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Tyr Leu Pro Trp Gly Asn Val Lys
                645                 650                 655

Pro Val Val Val Leu Ser Ser Tyr Trp Glu Asp Ile Ser His Arg Ile
            660                 665                 670

Glu Thr Gln Asn Gln Leu Leu Gly Ile Ala Asp Arg Leu Glu Ala Gly
        675                 680                 685

Leu Glu Gln Val His Leu Ala Leu Lys Ala Gln Cys Ser Thr Glu Asp
    690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
                725                 730                 735

Asp Gln Tyr Leu Tyr Gln Leu Arg Thr His His Leu Ser Gln Ile Thr
            740                 745                 750

Glu Ala Ala Leu Ala Leu Lys Leu Gly His Ser Glu Leu Pro Ala Ala
        755                 760                 765

Leu Glu Gln Ala Glu Asp Trp Leu Leu Arg Leu Arg Ala Leu Ala Glu
    770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
            820                 825                 830

Thr Ile Phe Leu Lys Tyr Pro Met Glu Lys Val Pro Gly Ala Arg Met
        835                 840                 845

Pro Val Gln Ile Arg Val Lys Leu Trp Phe Gly Leu Ser Val Asp Glu
    850                 855                 860
```

Lys Glu Phe Asn Gln Phe Ala Glu Gly Lys Leu Ser Val Phe Ala Glu
865 870 875 880

Thr Tyr Glu Asn Glu Thr Lys Leu Ala Leu Val Gly Asn Trp Gly Thr
885 890 895

Thr Gly Leu Thr Tyr Pro Lys Phe Ser Asp Val Thr Gly Lys Ile Lys
900 905 910

Leu Pro Lys Asp Ser Phe Arg Pro Ser Ala Gly Trp Thr Trp Ala Gly
915 920 925

Asp Trp Phe Val Cys Pro Glu Lys Thr Leu Leu His Asp Met Asp Ala
930 935 940

Gly His Leu Ser Phe Val Glu Glu Val Phe Glu Asn Gln Thr Arg Leu
945 950 955 960

Pro Gly Gly Gln Trp Ile Tyr Met Ser Asp Asn Tyr Thr Asp Val Asn
965 970 975

Gly Glu Lys Val Leu Pro Lys Asp Asp Ile Glu Cys Pro Leu Gly Trp
980 985 990

Lys Trp Glu Asp Glu Glu Trp Ser Thr Asp Leu Asn Arg Ala Val Asp
995 1000 1005

Glu Gln Gly Trp Glu Tyr Ser Ile Thr Ile Pro Pro Glu Arg Lys
1010 1015 1020

Pro Lys His Trp Val Pro Ala Glu Lys Met Tyr Tyr Thr His Arg
1025 1030 1035

Arg Arg Arg Trp Val Arg Leu Arg Arg Arg Asp Leu Ser Gln Met
1040 1045 1050

Glu Ala Leu Lys Arg His Arg Gln Ala Glu Ala Glu Gly Glu Gly
1055 1060 1065

Trp Glu Tyr Ala Ser Leu Phe Gly Trp Lys Phe His Leu Glu Tyr
1070 1075 1080

Arg Lys Thr Asp Ala Phe Arg Arg Arg Arg Trp Arg Arg Arg Met
1085 1090 1095

Glu Pro Leu Glu Lys Thr Gly Pro Ala Ala Val Phe Ala Leu Glu
1100 1105 1110

<210> SEQ ID NO 10
<211> LENGTH: 1287
<212> TYPE: PRT
<213> ORGANISM: Homo sapiens
<220> FEATURE:
<223> OTHER INFORMATION: 3' hDYSF protein fragment

<400> SEQUENCE: 10

Val Ile Trp Met Leu Gln Gly Asp Lys Arg Val Ala Tyr Gln Arg Val
1 5 10 15

Pro Ala His Gln Val Leu Phe Ser Arg Arg Gly Ala Asn Tyr Cys Gly
20 25 30

Lys Asn Cys Gly Lys Leu Gln Thr Ile Phe Leu Lys Tyr Pro Met Glu
35 40 45

Lys Val Pro Gly Ala Arg Met Pro Val Gln Ile Arg Val Lys Leu Trp
50 55 60

Phe Gly Leu Ser Val Asp Glu Lys Glu Phe Asn Gln Phe Ala Glu Gly
65 70 75 80

Lys Leu Ser Val Phe Ala Glu Thr Tyr Glu Asn Glu Thr Lys Leu Ala
85 90 95

Leu Val Gly Asn Trp Gly Thr Thr Gly Leu Thr Tyr Pro Lys Phe Ser
100 105 110

```
Asp Val Thr Gly Lys Ile Lys Leu Pro Lys Asp Ser Phe Arg Pro Ser
        115                 120                 125

Ala Gly Trp Thr Trp Ala Gly Asp Trp Phe Val Cys Pro Glu Lys Thr
    130                 135                 140

Leu Leu His Asp Met Asp Ala Gly His Leu Ser Phe Val Glu Glu Val
145                 150                 155                 160

Phe Glu Asn Gln Thr Arg Leu Pro Gly Gly Gln Trp Ile Tyr Met Ser
                165                 170                 175

Asp Asn Tyr Thr Asp Val Asn Gly Glu Lys Val Leu Pro Lys Asp Asp
            180                 185                 190

Ile Glu Cys Pro Leu Gly Trp Lys Trp Glu Asp Glu Glu Trp Ser Thr
        195                 200                 205

Asp Leu Asn Arg Ala Val Asp Glu Gln Gly Trp Glu Tyr Ser Ile Thr
    210                 215                 220

Ile Pro Pro Glu Arg Lys Pro Lys His Trp Val Pro Ala Glu Lys Met
225                 230                 235                 240

Tyr Tyr Thr His Arg Arg Arg Arg Trp Val Arg Leu Arg Arg Arg Asp
                245                 250                 255

Leu Ser Gln Met Glu Ala Leu Lys Arg His Arg Gln Ala Glu Ala Glu
            260                 265                 270

Gly Glu Gly Trp Glu Tyr Ala Ser Leu Phe Gly Trp Lys Phe His Leu
        275                 280                 285

Glu Tyr Arg Lys Thr Asp Ala Phe Arg Arg Arg Arg Trp Arg Arg Arg
    290                 295                 300

Met Glu Pro Leu Glu Lys Thr Gly Pro Ala Ala Val Phe Ala Leu Glu
305                 310                 315                 320

Gly Ala Leu Gly Gly Val Met Asp Asp Lys Ser Glu Asp Ser Met Ser
                325                 330                 335

Val Ser Thr Leu Ser Phe Gly Val Asn Arg Pro Thr Ile Ser Cys Ile
            340                 345                 350

Phe Asp Tyr Gly Asn Arg Tyr His Leu Arg Cys Tyr Met Tyr Gln Ala
        355                 360                 365

Arg Asp Leu Ala Ala Met Asp Lys Asp Ser Phe Ser Asp Pro Tyr Ala
    370                 375                 380

Ile Val Ser Phe Leu His Gln Ser Gln Lys Thr Val Val Val Lys Asn
385                 390                 395                 400

Thr Leu Asn Pro Thr Trp Asp Gln Thr Leu Ile Phe Tyr Glu Ile Glu
                405                 410                 415

Ile Phe Gly Glu Pro Ala Thr Val Ala Glu Gln Pro Pro Ser Ile Val
            420                 425                 430

Val Glu Leu Tyr Asp His Asp Thr Tyr Gly Ala Asp Glu Phe Met Gly
        435                 440                 445

Arg Cys Ile Cys Gln Pro Ser Leu Glu Arg Met Pro Arg Leu Ala Trp
    450                 455                 460

Phe Pro Leu Thr Arg Gly Ser Gln Pro Ser Gly Glu Leu Leu Ala Ser
465                 470                 475                 480

Phe Glu Leu Ile Gln Arg Glu Lys Pro Ala Ile His His Ile Pro Gly
                485                 490                 495

Phe Glu Val Gln Glu Thr Ser Arg Ile Leu Asp Glu Ser Glu Asp Thr
            500                 505                 510

Asp Leu Pro Tyr Pro Pro Pro Gln Arg Glu Ala Asn Ile Tyr Met Val
        515                 520                 525
```

-continued

Pro Gln Asn Ile Lys Pro Ala Leu Gln Arg Thr Ala Ile Glu Ile Leu
530 535 540

Ala Trp Gly Leu Arg Asn Met Lys Ser Tyr Gln Leu Ala Asn Ile Ser
545 550 555 560

Ser Pro Ser Leu Val Val Glu Cys Gly Gly Gln Thr Val Gln Ser Cys
565 570 575

Val Ile Arg Asn Leu Arg Lys Asn Pro Asn Phe Asp Ile Cys Thr Leu
580 585 590

Phe Met Glu Val Met Leu Pro Arg Glu Glu Leu Tyr Cys Pro Pro Ile
595 600 605

Thr Val Lys Val Ile Asp Asn Arg Gln Phe Gly Arg Arg Pro Val Val
610 615 620

Gly Gln Cys Thr Ile Arg Ser Leu Glu Ser Phe Leu Cys Asp Pro Tyr
625 630 635 640

Ser Ala Glu Ser Pro Ser Pro Gln Gly Gly Pro Asp Asp Val Ser Leu
645 650 655

Leu Ser Pro Gly Glu Asp Val Leu Ile Asp Ile Asp Asp Lys Glu Pro
660 665 670

Leu Ile Pro Ile Gln Glu Glu Glu Phe Ile Asp Trp Trp Ser Lys Phe
675 680 685

Phe Ala Ser Ile Gly Glu Arg Glu Lys Cys Gly Ser Tyr Leu Glu Lys
690 695 700

Asp Phe Asp Thr Leu Lys Val Tyr Asp Thr Gln Leu Glu Asn Val Glu
705 710 715 720

Ala Phe Glu Gly Leu Ser Asp Phe Cys Asn Thr Phe Lys Leu Tyr Arg
725 730 735

Gly Lys Thr Gln Glu Glu Thr Glu Asp Pro Ser Val Ile Gly Glu Phe
740 745 750

Lys Gly Leu Phe Lys Ile Tyr Pro Leu Pro Glu Asp Pro Ala Ile Pro
755 760 765

Met Pro Pro Arg Gln Phe His Gln Leu Ala Ala Gln Gly Pro Gln Glu
770 775 780

Cys Leu Val Arg Ile Tyr Ile Val Arg Ala Phe Gly Leu Gln Pro Lys
785 790 795 800

Asp Pro Asn Gly Lys Cys Asp Pro Tyr Ile Lys Ile Ser Ile Gly Lys
805 810 815

Lys Ser Val Ser Asp Gln Asp Asn Tyr Ile Pro Cys Thr Leu Glu Pro
820 825 830

Val Phe Gly Lys Met Phe Glu Leu Thr Cys Thr Leu Pro Leu Glu Lys
835 840 845

Asp Leu Lys Ile Thr Leu Tyr Asp Tyr Asp Leu Leu Ser Lys Asp Glu
850 855 860

Lys Ile Gly Glu Thr Val Val Asp Leu Glu Asn Arg Leu Leu Ser Lys
865 870 875 880

Phe Gly Ala Arg Cys Gly Leu Pro Gln Thr Tyr Cys Val Ser Gly Pro
885 890 895

Asn Gln Trp Arg Asp Gln Leu Arg Pro Ser Gln Leu Leu His Leu Phe
900 905 910

Cys Gln Gln His Arg Val Lys Ala Pro Val Tyr Arg Thr Asp Arg Val
915 920 925

Met Phe Gln Asp Lys Glu Tyr Ser Ile Glu Glu Ile Glu Ala Gly Arg
930 935 940

Ile Pro Asn Pro His Leu Gly Pro Val Glu Glu Arg Leu Ala Leu His

```
945                 950                 955                 960

Val Leu Gln Gln Gln Gly Leu Val Pro Glu His Val Glu Ser Arg Pro
                965                 970                 975

Leu Tyr Ser Pro Leu Gln Pro Asp Ile Glu Gln Gly Lys Leu Gln Met
            980                 985                 990

Trp Val Asp Leu Phe Pro Lys Ala  Leu Gly Arg Pro Gly  Pro Pro Phe
        995                 1000                1005

Asn Ile  Thr Pro Arg Arg Ala  Arg Arg Phe Phe Leu  Arg Cys Ile
    1010                 1015                 1020

Ile Trp  Asn Thr Arg Asp Val  Ile Leu Asp Asp Leu  Ser Leu Thr
    1025                 1030                 1035

Gly Glu  Lys Met Ser Asp Ile  Tyr Val Lys Gly Trp  Met Ile Gly
    1040                 1045                 1050

Phe Glu  Glu His Lys Gln Lys  Thr Asp Val His Tyr  Arg Ser Leu
    1055                 1060                 1065

Gly Gly  Glu Gly Asn Phe Asn  Trp Arg Phe Ile Phe  Pro Phe Asp
    1070                 1075                 1080

Tyr Leu  Pro Ala Glu Gln Val  Cys Thr Ile Ala Lys  Lys Asp Ala
    1085                 1090                 1095

Phe Trp  Arg Leu Asp Lys Thr  Glu Ser Lys Ile Pro  Ala Arg Val
    1100                 1105                 1110

Val Phe  Gln Ile Trp Asp Asn  Asp Lys Phe Ser Phe  Asp Asp Phe
    1115                 1120                 1125

Leu Gly  Ser Leu Gln Leu Asp  Leu Asn Arg Met Pro  Lys Pro Ala
    1130                 1135                 1140

Lys Thr  Ala Lys Lys Cys Ser  Leu Asp Gln Leu Asp  Asp Ala Phe
    1145                 1150                 1155

His Pro  Glu Trp Phe Val Ser  Leu Phe Glu Gln Lys  Thr Val Lys
    1160                 1165                 1170

Gly Trp  Trp Pro Cys Val Ala  Glu Glu Gly Glu Lys  Lys Ile Leu
    1175                 1180                 1185

Ala Gly  Lys Leu Glu Met Thr  Leu Glu Ile Val Ala  Glu Ser Glu
    1190                 1195                 1200

His Glu  Glu Arg Pro Ala Gly  Gln Gly Arg Asp Glu  Pro Asn Met
    1205                 1210                 1215

Asn Pro  Lys Leu Glu Asp Pro  Arg Arg Pro Asp Thr  Ser Phe Leu
    1220                 1225                 1230

Trp Phe  Thr Ser Pro Tyr Lys  Thr Met Lys Phe Ile  Leu Trp Arg
    1235                 1240                 1245

Arg Phe  Arg Trp Ala Ile Ile  Leu Phe Ile Ile Leu  Phe Ile Leu
    1250                 1255                 1260

Leu Leu  Phe Leu Ala Ile Phe  Ile Tyr Ala Phe Pro  Asn Tyr Ala
    1265                 1270                 1275

Ala Met  Lys Leu Val Lys Pro  Phe Ser
    1280                 1285
```

<210> SEQ ID NO 11
<211> LENGTH: 6914
<212> TYPE: DNA
<213> ORGANISM: Homo sapiens
<220> FEATURE:
<223> OTHER INFORMATION: hDYSF DNA full length

<400> SEQUENCE: 11
gcggccgccg cccagccagg tgcaaaatgc cgtgtcattg ggagactccg cagccggagc     60

```
attagattac agctcgacgg agctcgggaa gggcggcggg ggtggaagat gagcagaagc    120
ccctgttctc ggaacgccgg ctgacaagcg gggtgagcgc agccggggcg gggacccagc    180
ctagcccact ggagcagccg ggggtggccc gttcccccttt aagagcaact gctctaagcc   240
aggagccaga gattcgagcc ggcctcgccc agccagccct ctccagcgag gggacccaca    300
agcggcgcct cggccctccc gacctttccg agccctcttt gcgccctggg cgcacggggc    360
cctacacgcg ccaagcatgc tgagggtctt catcctctat gccgagaacg tccacacacc    420
cgacaccgac atcagcgatg cctactgctc cgcggtgttt gcaggggtga agaagagaac    480
caaagtcatc aagaacagcg tgaaccctgt atggaatgag ggatttgaat gggacctcaa    540
gggcatcccc ctggaccagg gctctgagct tcatgtggtg gtcaaagacc atgagacgat    600
ggggaggaac aggttcctgg gggaagccaa ggtcccactc cgagaggtcc tcgccacccc    660
tagtctgtcc gccagcttca atgcccccct gctggacacc aagaagcagc ccacaggggc    720
ctcgctggtc ctgcaggtgt cctacacacc gctgcctgga gctgtgcccc tgttcccgcc    780
ccctactcct ctggagccct ccccgactct gcctgacctg gatgtagtgg cagacacagg    840
aggagaggaa gacacagagg accagggact cactggagat gaggcggagc cattcctgga    900
tcaaagcgga ggcccggggg ctcccaccac cccaaggaaa ctaccttcac gtcctccgcc    960
ccactacccc gggatcaaaa gaaagcgaag tgcgcctaca tctagaaagc tgctgtcaga   1020
caaaccgcag gatttccaga tcagggtcca ggtgatcgag gggcgccagc tgccgggggt   1080
gaacatcaag cctgtggtca aggttaccgc tgcagggcag accaagcgga cgcggatcca   1140
caagggaaac agcccactct tcaatgagac tcttttcttc aacttgtttg actctcctgg   1200
ggagctgttt gatgagccca tctttatcac ggtggtagac tctcgttctc tcaggacaga   1260
tgctctcctc ggggagttcc ggatggacgt gggcaccatt tacagagagc cccggcacgc   1320
ctatctcagg aagtggctgc tgctctcaga ccctgatgac ttctctgctg gggccagagg   1380
ctacctgaaa acaagccttt gtgtgctggg gcctggggac gaagcgcctc tggagagaaa   1440
agacccctct gaagacaagg aggacattga aagcaacctg ctccggccca caggcgtagc   1500
cctgcgagga gcccacttct gcctgaaggt cttccgggcc gaggacttgc cgcagatgga   1560
cgatgccgtg atggacaacg tgaaacagat ctttggcttc gagagtaaca agaagaactt   1620
ggtggacccc tttgtggagg tcagctttgc ggggaaaatg ctgtgcagca agatcttgga   1680
gaagacggcc aaccctcagt ggaaccagaa catcacactg cctgccatgt ttccctccat   1740
gtgcgaaaaa atgaggattc gtatcataga ctgggaccgc ctgactcaca atgacatcgt   1800
ggctaccacc tacctgagta tgtcgaaaat ctctgcccct ggaggagaaa tagaagagga   1860
gcctgcaggt gctgtcaagc cttcgaaagc ctcagacttg gatgactacc tgggcttcct   1920
ccccactttt gggccctgct acatcaacct ctatggcagt cccagagagt tcacaggctt   1980
cccagacccc tacacagagc tcaacacagg caagggggaa ggtgtggctt atcgtggccg   2040
gcttctgctc tccctggaga ccaagctggt ggagcacagt gaacagaagg tggaggacct   2100
tcctgcggat gacatcctcc gggtggagaa gtaccttagg aggcgcaagt actccctgtt   2160
tgcggccttc tactcagcca ccatgctgca ggatgtggat gatgccatcc agtttgaggt   2220
cagcatcggg aactacggga acaagttcga catgacctgc ctgccgctgg cctccaccac   2280
tcagtacagc cgtgcagtct ttgacgggtg ccactactac tacctaccct ggggtaacgt   2340
gaaacctgtg gtggtgctgt catcctactg ggaggacatc agccatagaa tcgagactca   2400
```

gaaccagctg cttgggattg ctgaccggct ggaagctggc ctggagcagg tccacctggc 2460
cctgaaggcg cagtgctcca cggaggacgt ggactcgctg gtggctcagc tgacggatga 2520
gctcatcgca ggctgcagcc agcctctggg tgacatccat gagacaccct ctgccaccca 2580
cctggaccag tacctgtacc agctgcgcac ccatcacctg agccaaatca ctgaggctgc 2640
cctggccctg aagctcggcc acagtgagct ccctgcagct ctggagcagg cggaggactg 2700
gctcctgcgt ctgcgtgccc tggcagagga gccccagaac agcctgccgg acatcgtcat 2760
ctggatgctg cagggagaca agcgtgtggc ataccagcgg gtgcccgccc accaagtcct 2820
cttctcccgg cggggtgcca actactgtgg caagaattgt gggaagctac agacaatctt 2880
tctgaaatat ccgatggaga aggtgcctgg cgcccggatg ccagtgcaga tacgggtcaa 2940
gctgtggttt gggctctcag tggatgagaa ggagttcaac cagtttgctg aggggaagct 3000
gtctgtcttt gctgaaacct atgagaacga gactaagttg gcccttgttg ggaactgggg 3060
cacaacgggc ctcacctacc ccaagttttc tgacgtcacg ggcaagatca agctacccaa 3120
ggacagcttc cgcccctcgg ccggctggac ctgggctgga gattggttcg tgtgtccgga 3180
gaagactctg ctccatgaca tggacgccgg tcacctgagc ttcgtggaag aggtgtttga 3240
gaaccagacc cggcttcccg gaggccagtg gatctacatg agtgacaact acaccgatgt 3300
gaacggggag aaggtgcttc ccaaggatga cattgagtgc ccactgggct ggaagtggga 3360
agatgaggaa tggtccacag acctcaaccg ggctgtcgat gagcaaggct gggagtatag 3420
catcaccatc cccccggagc ggaagccgaa gcactgggtc cctgctgaga agatgtacta 3480
cacacaccga cggcggcgct gggtgcgcct gcgcaggagg gatctcagcc aaatggaagc 3540
actgaaaagg cacaggcagg cggaggcgga gggcgagggc tgggagtacg cctctctttt 3600
tggctggaag ttccacctcg agtaccgcaa gacagatgcc ttccgccgcc gccgctggcg 3660
ccgtcgcatg gagccactgg agaagacggg gcctgcagct gtgtttgccc ttgagggggc 3720
cctgggcggc gtgatggatg acaagagtga agattccatg tccgtctcca ccttgagctt 3780
cggtgtgaac agacccacga tttcctgcat attcgactat gggaaccgct accatctacg 3840
ctgctacatg taccaggccc gggacctggc tgcgatggac aaggactctt tttctgatcc 3900
ctatgccatc gtctccttcc tgcaccagag ccagaagacg gtggtggtga agaacaccct 3960
taaccccacc tgggaccaga cgctcatctt ctacgagatc gagatctttg gcgagccggc 4020
cacagttgct gagcaaccgc ccagcattgt ggtggagctg tacgaccatg acacttatgg 4080
tgcagacgag tttatgggtc gctgcatctg tcaaccgagt ctggaacgga tgccacggct 4140
ggcctggttc ccactgacga ggggcagcca gccgtcgggg gagctgctgg cctcttttga 4200
gctcatccag agagagaagc cggccatcca ccatattcct ggttttgagg tgcaggagac 4260
atcaaggatc ctggatgagt ctgaggacac agacctgccc tacccaccac cccagaggga 4320
ggccaacatc tacatggttc ctcagaacat caagccagcg ctccagcgta ccgccatcga 4380
gatcctggca tggggcctgc ggaacatgaa gagttaccag ctggccaaca tctcctcccc 4440
cagcctcgtg gtagagtgtg gggccagac ggtgcagtcc tgtgtcatca ggaacctccg 4500
gaagaacccc aactttgaca tctgcaccct cttcatggaa gtgatgctgc ccagggagga 4560
gctctactgc ccccccatca ccgtcaaggt catcgataac cgccagtttg gccgccggcc 4620
tgtggtgggc cagtgtacca tccgctccct ggagagcttc ctgtgtgacc cctactcggc 4680
ggagagtcca tccccacagg gtggcccaga cgatgtgagc ctactcagtc ctggggaaga 4740
cgtgctcatc gacattgatg acaaggagcc cctcatcccc atccaggagg aagagttcat 4800

```
cgattggtgg agcaaattct ttgcctccat aggggagagg gaaaagtgcg gctcctacct   4860
ggagaaggat tttgacaccc tgaaggtcta tgacacacag ctggagaatg tggaggcctt   4920
tgagggcctg tctgactttt gtaacacctt caagctgtac cggggcaaga cgcaggagga   4980
gacagaagat ccatctgtga ttggtgaatt taagggcctc ttcaaaattt atcccctccc   5040
agaagaccca gccatcccca tgcccccaag acagttccac cagctggccg cccagggacc   5100
ccaggagtgc ttggtccgta tctacattgt ccgagcattt ggcctgcagc ccaaggaccc   5160
caatggaaag tgtgatcctt acatcaagat ctccataggg aagaaatcag tgagtgacca   5220
ggataactac atcccctgca cgctggagcc cgtatttgga aagatgttcg agctgacctg   5280
cactctgcct ctggagaagg acctaaagat cactctctat gactatgacc tcctctccaa   5340
ggacgaaaag atcggtgaga cggtcgtcga cctggagaac aggctgctgt ccaagtttgg   5400
ggctcgctgt ggactcccac agacctactg tgtctctgga ccgaaccagt ggcgggacca   5460
gctccgcccc tcccagctcc tccacctctt ctgccagcag catagagtca aggcacctgt   5520
gtaccggaca gaccgtgtaa tgtttcagga taaagaatat tccattgaag agatagaggc   5580
tggcaggatc ccaaacccac acctgggccc agtggaggag cgtctggctc tgcatgtgct   5640
tcagcagcag ggcctggtcc cggagcacgt ggagtcacgg cccctctaca gccccctgca   5700
gccagacatc gagcagggga agctgcagat gtgggtcgac ctatttccga aggccctggg   5760
gcggcctgga cctcccttca acatcacccc acggagagcc agaaggtttt tcctgcgttg   5820
tattatctgg aataccagag atgtgatcct ggatgacctg agcctcacgg gggagaagat   5880
gagcgacatt tatgtgaaag gttggatgat tggctttgaa gaacacaagc aaaagacaga   5940
cgtgcattat cgttccctgg gaggtgaagg caacttcaac tggaggttca ttttcccctt   6000
cgactacctg ccagctgagc aagtctgtac cattgccaag aaggatgcct tctggaggct   6060
ggacaagact gagagcaaaa tcccagcacg agtggtgttc cagatctggg acaatgacaa   6120
gttctccttt gatgattttc tgggctccct gcagctcgat ctcaaccgca tgcccaagcc   6180
agccaagaca gccaagaagt gctccttgga ccagctggat gatgctttcc acccagaatg   6240
gtttgtgtcc ctttttgagc agaaaacagt gaagggctgg tggccctgtg tagcagaaga   6300
gggtgagaag aaaatactgg cgggcaagct ggaaatgacc ttggagattg tagcagagag   6360
tgagcatgag gagcggcctg ctggccaggg ccgggatgag cccaacatga accctaagct   6420
tgaggaccca aggcgccccg acacctcctt cctgtggttt acctccccat acaagaccat   6480
gaagttcatc ctgtggcggc gtttccggtg ggccatcatc ctcttcatca tcctcttcat   6540
cctgctgctg ttcctggcca tcttcatcta cgccttcccg aactatgctg ccatgaagct   6600
ggtgaagccc ttcagctgag gactctcctg ccctgtagaa ggggccgtgg ggtcccctcc   6660
agcatgggac tggcctgcct cctccgccca gctcggcgag ctcctccaga cctcctaggc   6720
ctgattgtcc tgccagggtg ggcagacaga cagatggacc ggcccacact cccagagttg   6780
ctaacatgga gctctgagat caccccactt ccatcatttc cttctccccc aacccaacgc   6840
tttttggat cagctcagac atatttcagt ataaaacagt tggaaccaca aaaaaaaaaa   6900
aaaaaaaaaa aaaa                                                     6914
```

<210> SEQ ID NO 12
<211> LENGTH: 2080
<212> TYPE: PRT
<213> ORGANISM: Homo sapiens
<220> FEATURE:

<223> OTHER INFORMATION: hDYSF protein full length

<400> SEQUENCE: 12

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu
    50                  55                  60

Leu His Val Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Pro Thr Pro Leu Glu Pro Ser Pro Thr
    130                 135                 140

Leu Pro Asp Leu Asp Val Val Ala Asp Thr Gly Gly Glu Glu Asp Thr
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Asp Phe Gln Ile Arg Val
    210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
        275                 280                 285

Ser Arg Ser Leu Arg Thr Asp Ala Leu Leu Gly Glu Phe Arg Met Asp
    290                 295                 300

Val Gly Thr Ile Tyr Arg Glu Pro Arg His Ala Tyr Leu Arg Lys Trp
305                 310                 315                 320

Leu Leu Leu Ser Asp Pro Asp Asp Phe Ser Ala Gly Ala Arg Gly Tyr
                325                 330                 335

Leu Lys Thr Ser Leu Cys Val Leu Gly Pro Gly Asp Glu Ala Pro Leu
            340                 345                 350

Glu Arg Lys Asp Pro Ser Glu Asp Lys Glu Asp Ile Glu Ser Asn Leu
        355                 360                 365

Leu Arg Pro Thr Gly Val Ala Leu Arg Gly Ala His Phe Cys Leu Lys
    370                 375                 380

Val Phe Arg Ala Glu Asp Leu Pro Gln Met Asp Asp Ala Val Met Asp
385                 390                 395                 400

```
Asn Val Lys Gln Ile Phe Gly Phe Glu Ser Asn Lys Lys Asn Leu Val
                405                 410                 415

Asp Pro Phe Val Glu Val Ser Phe Ala Gly Lys Met Leu Cys Ser Lys
            420                 425                 430

Ile Leu Glu Lys Thr Ala Asn Pro Gln Trp Asn Gln Asn Ile Thr Leu
        435                 440                 445

Pro Ala Met Phe Pro Ser Met Cys Glu Lys Met Arg Ile Arg Ile Ile
    450                 455                 460

Asp Trp Asp Arg Leu Thr His Asn Asp Ile Val Ala Thr Thr Tyr Leu
465                 470                 475                 480

Ser Met Ser Lys Ile Ser Ala Pro Gly Gly Glu Ile Glu Glu Glu Pro
                485                 490                 495

Ala Gly Ala Val Lys Pro Ser Lys Ala Ser Asp Leu Asp Asp Tyr Leu
            500                 505                 510

Gly Phe Leu Pro Thr Phe Gly Pro Cys Tyr Ile Asn Leu Tyr Gly Ser
        515                 520                 525

Pro Arg Glu Phe Thr Gly Phe Pro Asp Pro Tyr Thr Glu Leu Asn Thr
    530                 535                 540

Gly Lys Gly Glu Gly Val Ala Tyr Arg Gly Arg Leu Leu Leu Ser Leu
545                 550                 555                 560

Glu Thr Lys Leu Val Glu His Ser Glu Gln Lys Val Glu Asp Leu Pro
                565                 570                 575

Ala Asp Asp Ile Leu Arg Val Glu Lys Tyr Leu Arg Arg Arg Lys Tyr
            580                 585                 590

Ser Leu Phe Ala Ala Phe Tyr Ser Ala Thr Met Leu Gln Asp Val Asp
        595                 600                 605

Asp Ala Ile Gln Phe Glu Val Ser Ile Gly Asn Tyr Gly Asn Lys Phe
    610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Tyr Leu Pro Trp Gly Asn Val Lys
                645                 650                 655

Pro Val Val Val Leu Ser Ser Tyr Trp Glu Asp Ile Ser His Arg Ile
            660                 665                 670

Glu Thr Gln Asn Gln Leu Leu Gly Ile Ala Asp Arg Leu Glu Ala Gly
        675                 680                 685

Leu Glu Gln Val His Leu Ala Leu Lys Ala Gln Cys Ser Thr Glu Asp
    690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
                725                 730                 735

Asp Gln Tyr Leu Tyr Gln Leu Arg Thr His His Leu Ser Gln Ile Thr
            740                 745                 750

Glu Ala Ala Leu Ala Leu Lys Leu Gly His Ser Glu Leu Pro Ala Ala
        755                 760                 765

Leu Glu Gln Ala Glu Asp Trp Leu Leu Arg Leu Arg Ala Leu Ala Glu
    770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
```

```
            820                 825                 830

Thr Ile Phe Leu Lys Tyr Pro Met Glu Lys Val Pro Gly Ala Arg Met
        835                 840                 845

Pro Val Gln Ile Arg Val Lys Leu Trp Phe Gly Leu Ser Val Asp Glu
    850                 855                 860

Lys Glu Phe Asn Gln Phe Ala Glu Gly Lys Leu Ser Val Phe Ala Glu
865                 870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
            900                 905                 910

Leu Pro Lys Asp Ser Phe Arg Pro Ser Ala Gly Trp Thr Trp Ala Gly
        915                 920                 925

Asp Trp Phe Val Cys Pro Glu Lys Thr Leu Leu His Asp Met Asp Ala
    930                 935                 940

Gly His Leu Ser Phe Val Glu Glu Val Phe Glu Asn Gln Thr Arg Leu
945                 950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Asp Ile Glu Cys Pro Leu Gly Trp
            980                 985                 990

Lys Trp Glu Asp Glu Glu Trp Ser  Thr Asp Leu Asn Arg  Ala Val Asp
        995                 1000                1005

Glu Gln  Gly Trp Glu Tyr Ser  Ile Thr Ile Pro Pro  Glu Arg Lys
    1010                 1015                1020

Pro Lys  His Trp Val Pro Ala  Glu Lys Met Tyr Tyr  Thr His Arg
    1025                 1030                1035

Arg Arg  Arg Trp Val Arg Leu  Arg Arg Arg Asp Leu  Ser Gln Met
    1040                 1045                1050

Glu Ala  Leu Lys Arg His Arg  Gln Ala Glu Ala Glu  Gly Glu Gly
    1055                 1060                1065

Trp Glu  Tyr Ala Ser Leu Phe  Gly Trp Lys Phe His  Leu Glu Tyr
    1070                 1075                1080

Arg Lys  Thr Asp Ala Phe Arg  Arg Arg Arg Trp Arg  Arg Arg Met
    1085                 1090                1095

Glu Pro  Leu Glu Lys Thr Gly  Pro Ala Ala Val Phe  Ala Leu Glu
    1100                 1105                1110

Gly Ala  Leu Gly Gly Val Met  Asp Asp Lys Ser Glu  Asp Ser Met
    1115                 1120                1125

Ser Val  Ser Thr Leu Ser Phe  Gly Val Asn Arg Pro  Thr Ile Ser
    1130                 1135                1140

Cys Ile  Phe Asp Tyr Gly Asn  Arg Tyr His Leu Arg  Cys Tyr Met
    1145                 1150                1155

Tyr Gln  Ala Arg Asp Leu Ala  Ala Met Asp Lys Asp  Ser Phe Ser
    1160                 1165                1170

Asp Pro  Tyr Ala Ile Val Ser  Phe Leu His Gln Ser  Gln Lys Thr
    1175                 1180                1185

Val Val  Val Lys Asn Thr Leu  Asn Pro Thr Trp Asp  Gln Thr Leu
    1190                 1195                1200

Ile Phe  Tyr Glu Ile Glu Ile  Phe Gly Glu Pro Ala  Thr Val Ala
    1205                 1210                1215

Glu Gln  Pro Pro Ser Ile Val  Val Glu Leu Tyr Asp  His Asp Thr
    1220                 1225                1230
```

```
Tyr Gly  Ala Asp Glu Phe Met  Gly Arg Cys Ile Cys  Gln Pro Ser
    1235                 1240                 1245

Leu Glu  Arg Met Pro Arg Leu  Ala Trp Phe Pro Leu  Thr Arg Gly
    1250                 1255                 1260

Ser Gln  Pro Ser Gly Glu Leu  Leu Ala Ser Phe Glu  Leu Ile Gln
    1265                 1270                 1275

Arg Glu  Lys Pro Ala Ile His  His Ile Pro Gly Phe  Glu Val Gln
    1280                 1285                 1290

Glu Thr  Ser Arg Ile Leu Asp  Glu Ser Glu Asp Thr  Asp Leu Pro
    1295                 1300                 1305

Tyr Pro  Pro Pro Gln Arg Glu  Ala Asn Ile Tyr Met  Val Pro Gln
    1310                 1315                 1320

Asn Ile  Lys Pro Ala Leu Gln  Arg Thr Ala Ile Glu  Ile Leu Ala
    1325                 1330                 1335

Trp Gly  Leu Arg Asn Met Lys  Ser Tyr Gln Leu Ala  Asn Ile Ser
    1340                 1345                 1350

Ser Pro  Ser Leu Val Val Glu  Cys Gly Gly Gln Thr  Val Gln Ser
    1355                 1360                 1365

Cys Val  Ile Arg Asn Leu Arg  Lys Asn Pro Asn Phe  Asp Ile Cys
    1370                 1375                 1380

Thr Leu  Phe Met Glu Val Met  Leu Pro Arg Glu Glu  Leu Tyr Cys
    1385                 1390                 1395

Pro Pro  Ile Thr Val Lys Val  Ile Asp Asn Arg Gln  Phe Gly Arg
    1400                 1405                 1410

Arg Pro  Val Val Gly Gln Cys  Thr Ile Arg Ser Leu  Glu Ser Phe
    1415                 1420                 1425

Leu Cys  Asp Pro Tyr Ser Ala  Glu Ser Pro Ser Pro  Gln Gly Gly
    1430                 1435                 1440

Pro Asp  Asp Val Ser Leu Leu  Ser Pro Gly Glu Asp  Val Leu Ile
    1445                 1450                 1455

Asp Ile  Asp Asp Lys Glu Pro  Leu Ile Pro Ile Gln  Glu Glu Glu
    1460                 1465                 1470

Phe Ile  Asp Trp Trp Ser Lys  Phe Phe Ala Ser Ile  Gly Glu Arg
    1475                 1480                 1485

Glu Lys  Cys Gly Ser Tyr Leu  Glu Lys Asp Phe Asp  Thr Leu Lys
    1490                 1495                 1500

Val Tyr  Asp Thr Gln Leu Glu  Asn Val Glu Ala Phe  Glu Gly Leu
    1505                 1510                 1515

Ser Asp  Phe Cys Asn Thr Phe  Lys Leu Tyr Arg Gly  Lys Thr Gln
    1520                 1525                 1530

Glu Glu  Thr Glu Asp Pro Ser  Val Ile Gly Glu Phe  Lys Gly Leu
    1535                 1540                 1545

Phe Lys  Ile Tyr Pro Leu Pro  Glu Asp Pro Ala Ile  Pro Met Pro
    1550                 1555                 1560

Pro Arg  Gln Phe His Gln Leu  Ala Ala Gln Gly Pro  Gln Glu Cys
    1565                 1570                 1575

Leu Val  Arg Ile Tyr Ile Val  Arg Ala Phe Gly Leu  Gln Pro Lys
    1580                 1585                 1590

Asp Pro  Asn Gly Lys Cys Asp  Pro Tyr Ile Lys Ile  Ser Ile Gly
    1595                 1600                 1605

Lys Lys  Ser Val Ser Asp Gln  Asp Asn Tyr Ile Pro  Cys Thr Leu
    1610                 1615                 1620
```

```
Glu Pro  Val Phe Gly Lys Met  Phe Glu Leu Thr Cys  Thr Leu Pro
    1625                 1630                 1635

Leu Glu  Lys Asp Leu Lys Ile  Thr Leu Tyr Asp Tyr  Asp Leu Leu
    1640                 1645                 1650

Ser Lys  Asp Glu Lys Ile Gly  Glu Thr Val Val Asp  Leu Glu Asn
    1655                 1660                 1665

Arg Leu  Leu Ser Lys Phe Gly  Ala Arg Cys Gly Leu  Pro Gln Thr
    1670                 1675                 1680

Tyr Cys  Val Ser Gly Pro Asn  Gln Trp Arg Asp Gln  Leu Arg Pro
    1685                 1690                 1695

Ser Gln  Leu Leu His Leu Phe  Cys Gln Gln His Arg  Val Lys Ala
    1700                 1705                 1710

Pro Val  Tyr Arg Thr Asp Arg  Val Met Phe Gln Asp  Lys Glu Tyr
    1715                 1720                 1725

Ser Ile  Glu Glu Ile Glu Ala  Gly Arg Ile Pro Asn  Pro His Leu
    1730                 1735                 1740

Gly Pro  Val Glu Glu Arg Leu  Ala Leu His Val Leu  Gln Gln Gln
    1745                 1750                 1755

Gly Leu  Val Pro Glu His Val  Glu Ser Arg Pro Leu  Tyr Ser Pro
    1760                 1765                 1770

Leu Gln  Pro Asp Ile Glu Gln  Gly Lys Leu Gln Met  Trp Val Asp
    1775                 1780                 1785

Leu Phe  Pro Lys Ala Leu Gly  Arg Pro Gly Pro Pro  Phe Asn Ile
    1790                 1795                 1800

Thr Pro  Arg Arg Ala Arg Arg  Phe Phe Leu Arg Cys  Ile Ile Trp
    1805                 1810                 1815

Asn Thr  Arg Asp Val Ile Leu  Asp Asp Leu Ser Leu  Thr Gly Glu
    1820                 1825                 1830

Lys Met  Ser Asp Ile Tyr Val  Lys Gly Trp Met Ile  Gly Phe Glu
    1835                 1840                 1845

Glu His  Lys Gln Lys Thr Asp  Val His Tyr Arg Ser  Leu Gly Gly
    1850                 1855                 1860

Glu Gly  Asn Phe Asn Trp Arg  Phe Ile Phe Pro Phe  Asp Tyr Leu
    1865                 1870                 1875

Pro Ala  Glu Gln Val Cys Thr  Ile Ala Lys Lys Asp  Ala Phe Trp
    1880                 1885                 1890

Arg Leu  Asp Lys Thr Glu Ser  Lys Ile Pro Ala Arg  Val Val Phe
    1895                 1900                 1905

Gln Ile  Trp Asp Asn Asp Lys  Phe Ser Phe Asp Asp  Phe Leu Gly
    1910                 1915                 1920

Ser Leu  Gln Leu Asp Leu Asn  Arg Met Pro Lys Pro  Ala Lys Thr
    1925                 1930                 1935

Ala Lys  Lys Cys Ser Leu Asp  Gln Leu Asp Asp Ala  Phe His Pro
    1940                 1945                 1950

Glu Trp  Phe Val Ser Leu Phe  Glu Gln Lys Thr Val  Lys Gly Trp
    1955                 1960                 1965

Trp Pro  Cys Val Ala Glu Glu  Gly Glu Lys Lys Ile  Leu Ala Gly
    1970                 1975                 1980

Lys Leu  Glu Met Thr Leu Glu  Ile Val Ala Glu Ser  Glu His Glu
    1985                 1990                 1995

Glu Arg  Pro Ala Gly Gln Gly  Arg Asp Glu Pro Asn  Met Asn Pro
    2000                 2005                 2010

Lys Leu  Glu Asp Pro Arg Arg  Pro Asp Thr Ser Phe  Leu Trp Phe
```

```
    2015                2020                2025

Thr Ser  Pro Tyr Lys Thr Met  Lys Phe Ile Leu Trp  Arg Arg Phe
    2030                2035                2040

Arg Trp  Ala Ile Ile Leu Phe  Ile Ile Leu Phe Ile  Leu Leu Leu
    2045                2050                2055

Phe Leu  Ala Ile Phe Ile Tyr  Ala Phe Pro Asn Tyr  Ala Ala Met
    2060                2065                2070

Lys Leu  Val Lys Pro Phe Ser
    2075                2080


<210> SEQ ID NO 13
<211> LENGTH: 3340
<212> TYPE: DNA
<213> ORGANISM: Homo sapiens
<220> FEATURE:
<223> OTHER INFORMATION: 5' hDYSF DNA fragment v2

<400> SEQUENCE: 13

atgctgaggg tcttcatcct ctatgccgag aacgtccaca cacccgacac cgacatcagc     60

gatgcctact gctccgcggt gtttgcaggg gtgaagaaga gaaccaaagt catcaagaac    120

agcgtgaacc ctgtatggaa tgagggattt gaatgggacc tcaagggcat ccccctggac    180

cagggctctg agcttcatgt ggtggtcaaa gaccatgaga cgatggggag gaacaggttc    240

ctgggggaag ccaaggtccc actccgagag gtcctcgcca cccctagtct gtccgccagc    300

ttcaatgccc ccctgctgga caccaagaag cagcccacag ggcctcgct ggtcctgcag     360

gtgtcctaca caccgctgcc tggagctgtg cccctgttcc cgccccctac tcctctggag    420

ccctccccga ctctgcctga cctggatgta gtggcagaca caggaggaga ggaagacaca    480

gaggaccagg gactcactgg agatgaggcg gagccattcc tggatcaaag cggaggcccg    540

ggggctccca ccaccccaag gaaactacct tcacgtcctc cgccccacta ccccgggatc    600

aaaagaaagc gaagtgcgcc tacatctaga aagctgctgt cagacaaacc gcaggatttc    660

cagatcaggg tccaggtgat cgaggggcgc cagctgccgg gggtgaacat caagcctgtg    720

gtcaaggtta ccgctgcagg gcagaccaag cggacgcgga tccacaaggg aaacagccca    780

ctcttcaatg agactctttt cttcaacttg tttgactctc ctggggagct gtttgatgag    840

cccatcttta tcacggtggt agactctcgt tctctcagga cagatgctct cctcggggag    900

ttccggatgg acgtgggcac catttacaga gagccccggc acgcctatct caggaagtgg    960

ctgctgctct cagaccctga tgacttctct gctggggcca gaggctacct gaaaacaagc   1020

ctttgtgtgc tggggcctgg ggacgaagcg cctctggaga gaaaagaccc ctctgaagac   1080

aaggaggaca ttgaaagcaa cctgctccgg cccacaggcg tagccctgcg aggagcccac   1140

ttctgcctga aggtcttccg ggccgaggac ttgccgcaga tggacgatgc cgtgatggac   1200

aacgtgaaac agatctttgg cttcgagagt aacaagaaga acttggtgga cccctttgtg   1260

gaggtcagct ttgcggggaa aatgctgtgc agcaagatct tggagaagac ggccaaccct   1320

cagtggaacc agaacatcac actgcctgcc atgtttccct ccatgtgcga aaaaatgagg   1380

attcgtatca tagactggga ccgcctgact cacaatgaca tcgtggctac cacctacctg   1440

agtatgtcga aaatctctgc ccctggagga gaaatagaag aggagcctgc aggtgctgtc   1500

aagccttcga aagcctcaga cttggatgac tacctgggct tcctccccac ttttgggccc   1560

tgctacatca acctctatgg cagtcccaga gagttcacag gcttcccaga cccctacaca   1620

gagctcaaca caggcaaggg ggaaggtgtg gcttatcgtg gccggcttct gctctccctg   1680
```

gagaccaagc tggtggagca cagtgaacag aaggtggagg accttcctgc ggatgacatc 1740
ctccgggtgg agaagtacct taggaggcgc aagtactccc tgtttgcggc cttctactca 1800
gccaccatgc tgcaggatgt ggatgatgcc atccagtttg aggtcagcat cgggaactac 1860
gggaacaagt tcgacatgac ctgcctgccg ctggcctcca ccactcagta cagccgtgca 1920
gtctttgacg ggtgccacta ctactaccta ccctggggta acgtgaaacc tgtggtggtg 1980
ctgtcatcct actgggagga catcagccat agaatcgaga ctcagaacca gctgcttggg 2040
attgctgacc ggctggaagc tggcctggag caggtccacc tggccctgaa ggcgcagtgc 2100
tccacggagg acgtggactc gctggtggct cagctgacgg atgagctcat cgcaggctgc 2160
agccagcctc tgggtgacat ccatgagaca ccctctgcca cccacctgga ccagtacctg 2220
taccagctgc gcacccatca cctgagccaa atcactgagg ctgccctggc cctgaagctc 2280
ggccacagtg agctccctgc agctctggag caggcggagg actggctcct gcgtctgcgt 2340
gccctggcag aggagcccca gaacagcctg ccggacatcg tcatctggat gctgcaggga 2400
gacaagcgtg tggcatacca gcgggtgccc gcccaccaag tcctcttctc ccggcggggt 2460
gccaactact gtggcaagaa ttgtgggaag ctacagacaa tctttctgaa atatccgatg 2520
gagaaggtgc ctggcgcccg gatgccagtg cagatacggg tcaagctgtg gtttgggctc 2580
tcagtggatg agaaggagtt caaccagttt gctgagggga agctgtctgt ctttgctgaa 2640
acctatgaga acgagactaa gttggccctt gttgggaact ggggcacaac gggcctcacc 2700
taccccaagt tttctgacgt cacgggcaag atcaagctac ccaaggacag cttccgcccc 2760
tcggccggct ggacctgggc tggagattgg ttcgtgtgtc cggagaagac tctgctccat 2820
gacatggacg ccggtcacct gagcttcgtg gaagaggtgt ttgagaacca gacccggctt 2880
cccggaggcc agtggatcta catgagtgac aactacaccg atgtgaacgg ggagaaggtg 2940
cttcccaagg atgacattga gtgcccactg ggctggaagt gggaagatga ggaatggtcc 3000
acagacctca accgggctgt cgatgagcaa ggctgggagt atagcatcac catccccccg 3060
gagcggaagc cgaagcactg ggtccctgct gagaagatgt actacacaca ccgacggcgg 3120
cgctgggtgc gcctgcgcag gagggatctc agccaaatgg aagcactgaa aaggcacagg 3180
caggcggagg cggagggcga gggctgggag tacgcctctc tttttggctg gaagttccac 3240
ctcgagtacc gcaagacaga tgccttccgc cgccgccgct ggcgccgtcg catggagcca 3300
ctggagaaga cggggcctgc agctgtgttt gcccttgagg 3340

<210> SEQ ID NO 14
<211> LENGTH: 3866
<212> TYPE: DNA
<213> ORGANISM: Homo sapiens
<220> FEATURE:
<223> OTHER INFORMATION: 3' hDYSF DNA fragment v2

<400> SEQUENCE: 14
tcgtcatctg gatgctgcag ggagacaagc gtgtggcata ccagcgggtg cccgcccacc 60
aagtcctctt ctcccggcgg ggtgccaact actgtggcaa gaattgtggg aagctacaga 120
caatctttct gaaatatccg atggagaagg tgcctggcgc ccggatgcca gtgcagatac 180
gggtcaagct gtggtttggg ctctcagtgg atgagaagga gttcaaccag tttgctgagg 240
ggaagctgtc tgtctttgct gaaacctatg agaacgagac taagttggcc cttgttggga 300
actggggcac aacgggcctc acctacccca agttttctga cgtcacgggc aagatcaagc 360

```
tacccaagga cagcttccgc ccctcggccg gctggacctg ggctggagat tggttcgtgt    420

gtccggagaa gactctgctc catgacatgg acgccggtca cctgagcttc gtggaagagg    480

tgtttgagaa ccagacccgg cttcccggag gccagtggat ctacatgagt gacaactaca    540

ccgatgtgaa cggggagaag gtgcttccca aggatgacat tgagtgccca ctgggctgga    600

agtgggaaga tgaggaatgg tccacagacc tcaaccgggc tgtcgatgag caaggctggg    660

agtatagcat caccatcccc ccggagcgga agccgaagca ctgggtccct gctgagaaga    720

tgtactacac acaccgacgg cggcgctggg tgcgcctgcg caggagggat ctcagccaaa    780

tggaagcact gaaaaggcac aggcaggcgg aggcggaggg cgagggctgg gagtacgcct    840

ctctttttgg ctggaagttc cacctcgagt accgcaagac agatgccttc cgccgccgcc    900

gctggcgccg tcgcatggag ccactggaga agacggggcc tgcagctgtg tttgcccttg    960

agggggccct gggcggcgtg atggatgaca agagtgaaga ttccatgtcc gtctccacct   1020

tgagcttcgg tgtgaacaga cccacgattt cctgcatatt cgactatggg aaccgctacc   1080

atctacgctg ctacatgtac caggcccggg acctggctgc gatggacaag gactcttttt   1140

ctgatcccta tgccatcgtc tccttcctgc accagagcca gaagacggtg gtggtgaaga   1200

acacccttaa ccccacctgg gaccagacgc tcatcttcta cgagatcgag atctttggcg   1260

agccggccac agttgctgag caaccgccca gcattgtggt ggagctgtac gaccatgaca   1320

cttatggtgc agacgagttt atgggtcgct gcatctgtca accgagtctg gaacggatgc   1380

cacggctggc ctggttccca ctgacgaggg gcagccagcc gtcgggggag ctgctggcct   1440

cttttgagct catccagaga gagaagccgg ccatccacca tattcctggt tttgaggtgc   1500

aggagacatc aaggatcctg gatgagtctg aggacacaga cctgccctac ccaccacccc   1560

agagggaggc caacatctac atggttcctc agaacatcaa gccagcgctc cagcgtaccg   1620

ccatcgagat cctggcatgg ggcctgcgga acatgaagag ttaccagctg gccaacatct   1680

cctcccccag cctcgtggta gagtgtgggg gccagacggt gcagtcctgt gtcatcagga   1740

acctccggaa gaaccccaac tttgacatct gcaccctctt catggaagtg atgctgccca   1800

gggaggagct ctactgcccc cccatcaccg tcaaggtcat cgataaccgc cagtttggcc   1860

gccggcctgt ggtgggccag tgtaccatcc gctccctgga gagcttcctg tgtgacccct   1920

actcggcgga gagtccatcc ccacagggtg gcccagacga tgtgagccta ctcagtcctg   1980

gggaagacgt gctcatcgac attgatgaca aggagcccct catccccatc caggaggaag   2040

agttcatcga ttggtggagc aaattctttg cctccatagg ggagagggaa aagtgcggct   2100

cctacctgga gaaggatttt gacaccctga aggtctatga cacacagctg gagaatgtgg   2160

aggcctttga gggcctgtct gacttttgta acaccttcaa gctgtaccgg ggcaagacgc   2220

aggaggagac agaagatcca tctgtgattg gtgaatttaa gggcctcttc aaaatttatc   2280

ccctcccaga agacccagcc atccccatgc cccaagaca gttccaccag ctggccgccc   2340

agggacccca ggagtgcttg gtccgtatct acattgtccg agcatttggc ctgcagccca   2400

aggaccccaa tggaaagtgt gatccttaca tcaagatctc catagggaag aaatcagtga   2460

gtgaccagga taactacatc ccctgcacgc tggagcccgt atttggaaag atgttcgagc   2520

tgacctgcac tctgcctctg gagaaggacc taaagatcac tctctatgac tatgacctcc   2580

tctccaagga cgaaaagatc ggtgagacgg tcgtcgacct ggagaacagg ctgctgtcca   2640

agtttggggc tcgctgtgga ctcccacaga cctactgtgt ctctggaccg aaccagtggc   2700

gggaccagct ccgcccctcc cagctcctcc acctcttctg ccagcagcat agagtcaagg   2760
```

cacctgtgta ccggacagac cgtgtaatgt ttcaggataa agaatattcc attgaagaga 2820
tagaggctgg caggatccca aacccacacc tgggcccagt ggaggagcgt ctggctctgc 2880
atgtgcttca gcagcagggc ctggtcccgg agcacgtgga gtcacggccc ctctacagcc 2940
ccctgcagcc agacatcgag caggggaagc tgcagatgtg ggtcgaccta tttccgaagg 3000
ccctggggcg gcctggacct cccttcaaca tcaccccacg gagagccaga aggtttttcc 3060
tgcgttgtat tatctggaat accagagatg tgatcctgga tgacctgagc ctcacggggg 3120
agaagatgag cgacatttat gtgaaaggtt ggatgattgg ctttgaagaa cacaagcaaa 3180
agacagacgt gcattatcgt tccctgggag gtgaaggcaa cttcaactgg aggttcattt 3240
tccccttcga ctacctgcca gctgagcaag tctgtaccat tgccaagaag gatgccttct 3300
ggaggctgga caagactgag agcaaaatcc cagcacgagt ggtgttccag atctgggaca 3360
atgacaagtt ctcctttgat gattttctgg gctccctgca gctcgatctc aaccgcatgc 3420
ccaagccagc caagacagcc aagaagtgct ccttggacca gctggatgat gctttccacc 3480
cagaatggtt tgtgtccctt tttgagcaga aaacagtgaa gggctggtgg ccctgtgtag 3540
cagaagaggg tgagaagaaa atactggcgg gcaagctgga aatgaccttg gagattgtag 3600
cagagagtga gcatgaggag cggcctgctg gccagggccg ggatgagccc aacatgaacc 3660
ctaagcttga ggacccaagg cgccccgaca cctccttcct gtggtttacc tccccataca 3720
agaccatgaa gttcatcctg tggcggcgtt tccggtgggc catcatcctc ttcatcatcc 3780
tcttcatcct gctgctgttc ctggccatct tcatctacgc cttcccgaac tatgctgcca 3840
tgaagctggt gaagcccttc agctga 3866

<210> SEQ ID NO 15
<211> LENGTH: 4689
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: DYSF F5' Expresson Cassette v2

<400> SEQUENCE: 15
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctctaga gtttaagctt gcatgtctaa 180
gctagaccct tcagattaaa aataactgag gtaagggcct gggtagggga ggtggtgtga 240
gacgctcctg tctctcctct atctgcccat cggccctttg gggaggagga atgtgcccaa 300
ggactaaaaa aaggccatgg agccagaggg gcgagggcaa cagacctttc atgggcaaac 360
cttggggccc tgctgtctag catgccccac tacgggtcta ggctgcccat gtaaggaggc 420
aaggcctggg gacacccgag atgcctggtt ataattaacc cagacatgtg gctgcccccc 480
cccccccaac acctgctgcc tctaaaaata accctgtccc tggtggatcc cctgcatgcg 540
aagatcttcg aacaaggctg tgggggactg agggcaggct gtaacaggct tgggggccag 600
ggcttatacg tgcctgggac tcccaaagta ttactgttcc atgttcccgg cgaagggcca 660
gctgtccccc gccagctaga ctcagcactt agtttaggaa ccagtgagca agtcagccct 720
tggggcagcc catacaaggc catggggctg ggcaagctgc acgcctgggt ccggggtggg 780
cacggtgccc gggcaacgag ctgaaagctc atctgctctc aggggcccct ccctggggac 840

```
agcccctcct ggctagtcac accctgtagg ctcctctata taacccaggg gcacaggggc    900
tgccctcatt ctaccaccac ctccacagca cagacagaca ctcaggagca gccagcggcg    960
cgcccaggta agtttagtct ttttgtcttt tatttcaggt cccggatccg gtggtggtgc   1020
aaatcaaaga actgctcctc agtggatgtt gcctttactt ctaggcctgt acggaagtgt   1080
tacttctgct ctaaaagctg cggaattgta cccgcggccg cggctagcca ccatgctgag   1140
ggtcttcatc ctctatgccg agaacgtcca cacacccgac accgacatca gcgatgccta   1200
ctgctccgcg gtgtttgcag ggtgaagaa gagaaccaaa gtcatcaaga acagcgtgaa    1260
ccctgtatgg aatgagggat ttgaatggga cctcaagggc atccccctgg accagggctc   1320
tgagcttcat gtggtggtca aagaccatga gacgatgggg aggaacaggt tcctgggggga  1380
agccaaggtc ccactccgag aggtcctcgc cacccctagt ctgtccgcca gcttcaatgc   1440
ccccctgctg gacaccaaga agcagcccac aggggcctcg ctggtcctgc aggtgtccta   1500
cacaccgctg cctggagctg tgcccctgtt cccgcccccct actcctctgg agccctcccc  1560
gactctgcct gacctggatg tagtggcaga cacaggagga gaggaagaca cagaggacca   1620
gggactcact ggagatgagg cggagccatt cctggatcaa agcggaggcc cgggggctcc   1680
caccacccca aggaaactac cttcacgtcc tccgccccac taccccggga tcaaaagaaa   1740
gcgaagtgcg cctacatcta gaaagctgct gtcagacaaa ccgcaggatt tccagatcag   1800
ggtccaggtg atcgaggggc gccagctgcc gggggtgaac atcaagcctg tggtcaaggt   1860
taccgctgca gggcagacca agcggacgcg gatccacaag ggaaacagcc cactcttcaa   1920
tgagactctt ttcttcaact tgtttgactc tcctggggag ctgtttgatg agcccatctt   1980
tatcacggtg gtagactctc gttctctcag gacagatgct ctcctcgggg agttccggat   2040
ggacgtgggc accatttaca gagagccccg gcacgcctat ctcaggaagt ggctgctgct   2100
ctcagaccct gatgacttct ctgctggggc cagaggctac ctgaaaacaa gcctttgtgt   2160
gctggggcct ggggacgaag cgcctctgga gagaaaagac ccctctgaag acaaggagga   2220
cattgaaagc aacctgctcc ggcccacagg cgtagccctg cgaggagccc acttctgcct   2280
gaaggtcttc cgggccgagg acttgccgca gatggacgat gccgtgatgg acaacgtgaa   2340
acagatcttt ggcttcgaga gtaacaagaa gaacttggtg gaccccttg tggaggtcag    2400
ctttgcgggg aaaatgctgt gcagcaagat cttggagaag acggccaacc ctcagtggaa   2460
ccagaacatc acactgcctg ccatgtttcc ctccatgtgc gaaaaaatga ggattcgtat   2520
catagactgg gaccgcctga ctcacaatga catcgtggct accacctacc tgagtatgtc   2580
gaaaatctct gcccctggag gagaaataga agaggagcct gcaggtgctg tcaagccttc   2640
gaaagcctca gacttggatg actacctggg cttcctcccc acttttgggc cctgctacat   2700
caacctctat ggcagtccca gagagttcac aggcttccca gacccctaca cagagctcaa   2760
cacaggcaag gggaaggtg tggcttatcg tggccggctt ctgctctccc tggagaccaa    2820
gctggtggag cacagtgaac agaaggtgga ggaccttcct gcggatgaca tcctccgggt   2880
ggagaagtac cttaggaggc gcaagtactc cctgtttgcg gccttctact cagccaccat   2940
gctgcaggat gtggatgatg ccatccagtt tgaggtcagc atcgggaact acgggaacaa   3000
gttcgacatg acctgcctgc cgctggcctc caccactcag tacagccgtg cagtctttga   3060
cgggtgccac tactactacc taccctgggg taacgtgaaa cctgtggtgg tgctgtcatc   3120
ctactgggag gacatcagcc atagaatcga gactcagaac cagctgcttg ggattgctga   3180
```

ccggctggaa gctggcctgg agcaggtcca cctggccctg aaggcgcagt gctccacgga 3240
ggacgtggac tcgctggtgg ctcagctgac ggatgagctc atcgcaggct gcagccagcc 3300
tctgggtgac atccatgaga caccctctgc cacccacctg gaccagtacc tgtaccagct 3360
gcgcacccat cacctgagcc aaatcactga ggctgccctg gccctgaagc tcggccacag 3420
tgagctccct gcagctctgg agcaggcgga ggactggctc ctgcgtctgc gtgccctggc 3480
agaggagccc cagaacagcc tgccggacat cgtcatctgg atgctgcagg gagacaagcg 3540
tgtggcatac cagcgggtgc ccgcccacca agtcctcttc tcccggcggg gtgccaacta 3600
ctgtggcaag aattgtggga agctacagac aatctttctg aaatatccga tggagaaggt 3660
gcctggcgcc cggatgccag tgcagatacg ggtcaagctg tggtttgggc tctcagtgga 3720
tgagaaggag ttcaaccagt ttgctgaggg gaagctgtct gtctttgctg aaacctatga 3780
gaacgagact aagttggccc ttgttgggaa ctggggcaca acgggcctca cctaccccaa 3840
gttttctgac gtcacgggca agatcaagct acccaaggac agcttccgcc cctcggccgg 3900
ctggacctgg gctggagatt ggttcgtgtg tccggagaag actctgctcc atgacatgga 3960
cgccggtcac ctgagcttcg tggaagaggt gtttgagaac cagacccggc ttcccggagg 4020
ccagtggatc tacatgagtg acaactacac cgatgtgaac ggggagaagg tgcttcccaa 4080
ggatgacatt gagtgcccac tgggctggaa gtgggaagat gaggaatggt ccacagacct 4140
caaccgggct gtcgatgagc aaggctggga gtatagcatc accatccccc cggagcggaa 4200
gccgaagcac tgggtccctg ctgagaagat gtactacaca caccgacggc ggcgctgggt 4260
gcgcctgcgc aggagggatc tcagccaaat ggaagcactg aaaaggcaca ggcaggcgga 4320
ggcggagggc gagggctggg agtacgcctc tctttttggc tggaagttcc acctcgagta 4380
ccgcaagaca gatgccttcc gccgccgccg ctggcgccgt cgcatggagc cactggagaa 4440
gacggggcct gcagctgtgt ttgcccttga gggcggccgc aataaaagat ctttattttc 4500
attagatctg tgtgttggtt ttttgtgtgt ctagagcatg gcgggttaat cattaactac 4560
aaggaacccc tagtgatgga gttggccact ccctctctgc gcgctcgctc gctcactgag 4620
gccgggcgac caaaggtcgc ccgacgcccg ggctttgccc gggcggcctc agtgagcgag 4680
cgagcgcgc 4689

<210> SEQ ID NO 16
<211> LENGTH: 4592
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: DYSF F3' Expression Cassette v2

<400> SEQUENCE: 16
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtagc catgctctgg 180
tcgactctag agttttcgtc atctggatgc tgcagggaga caagcgtgtg gcataccagc 240
gggtgcccgc ccaccaagtc ctcttctccc ggcggggtgc caactactgt ggcaagaatt 300
gtgggaagct acagacaatc tttctgaaat atccgatgga gaaggtgcct ggcgcccgga 360
tgccagtgca gatacgggtc aagctgtggt ttgggctctc agtggatgag aaggagttca 420

```
accagtttgc tgaggggaag ctgtctgtct ttgctgaaac ctatgagaac gagactaagt    480
tggcccttgt tgggaactgg ggcacaacgg gcctcaccta ccccaagttt tctgacgtca    540
cgggcaagat caagctaccc aaggacagct tccgcccctc ggccggctgg acctgggctg    600
gagattggtt cgtgtgtccg gagaagactc tgctccatga catggacgcc ggtcacctga    660
gcttcgtgga agaggtgttt gagaaccaga cccggcttcc cggaggccag tggatctaca    720
tgagtgacaa ctacaccgat gtgaacgggg agaaggtgct tcccaaggat gacattgagt    780
gcccactggg ctggaagtgg gaagatgagg aatggtccac agacctcaac cgggctgtcg    840
atgagcaagg ctgggagtat agcatcacca tccccccgga gcggaagccg aagcactggg    900
tccctgctga gaagatgtac tacacacacc gacggcggcg ctgggtgcgc ctgcgcagga    960
gggatctcag ccaaatggaa gcactgaaaa ggcacaggca ggcggaggcg gagggcgagg   1020
gctgggagta cgcctctctt tttggctgga agttccacct cgagtaccgc aagacagatg   1080
ccttccgccg ccgccgctgg cgccgtcgca tggagccact ggagaagacg gggcctgcag   1140
ctgtgtttgc ccttgagggg gccctgggcg gcgtgatgga tgacaagagt gaagattcca   1200
tgtccgtctc caccttgagc ttcggtgtga acagacccac gatttcctgc atattcgact   1260
atgggaaccg ctaccatcta cgctgctaca tgtaccaggc ccgggacctg gctgcgatgg   1320
acaaggactc tttttctgat ccctatgcca tcgtctcctt cctgcaccag agccagaaga   1380
cggtggtggt gaagaacacc cttaacccca cctgggacca gacgctcatc ttctacgaga   1440
tcgagatctt tggcgagccg gccacagttg ctgagcaacc gcccagcatt gtggtggagc   1500
tgtacgacca tgacacttat ggtgcagacg agtttatggg tcgctgcatc tgtcaaccga   1560
gtctggaacg gatgccacgg ctggcctggt tcccactgac gaggggcagc cagccgtcgg   1620
gggagctgct ggcctctttt gagctcatcc agagagagaa gccggccatc caccatattc   1680
ctggttttga ggtgcaggag acatcaagga tcctggatga gtctgaggac acagacctgc   1740
cctacccacc accccagagg gaggccaaca tctacatggt tcctcagaac atcaagccag   1800
cgctccagcg taccgccatc gagatcctgg catggggcct gcggaacatg aagagttacc   1860
agctggccaa catctcctcc cccagcctcg tggtagagtg tgggggccag acggtgcagt   1920
cctgtgtcat caggaacctc cggaagaacc ccaactttga catctgcacc ctcttcatgg   1980
aagtgatgct gcccagggag gagctctact gccccccat caccgtcaag gtcatcgata   2040
accgccagtt tggccgccgg cctgtggtgg gccagtgtac catccgctcc ctggagagct   2100
tcctgtgtga cccctactcg gcggagagtc catccccaca gggtggccca gacgatgtga   2160
gcctactcag tcctggggaa gacgtgctca tcgacattga tgacaaggag cccctcatcc   2220
ccatccagga ggaagagttc atcgattggt ggagcaaatt ctttgcctcc ataggggaga   2280
gggaaaagtg cggctcctac ctggagaagg attttgacac cctgaaggtc tatgacacac   2340
agctggagaa tgtggaggcc tttgagggcc tgtctgactt ttgtaacacc ttcaagctgt   2400
accggggcaa gacgcaggag gagacagaag atccatctgt gattggtgaa tttaagggcc   2460
tcttcaaaat ttatcccctc ccagaagacc cagccatccc catgccccca agacagttcc   2520
accagctggc cgcccaggga ccccaggagt gcttggtccg tatctacatt gtccgagcat   2580
ttggcctgca gcccaaggac cccaatggaa agtgtgatcc ttacatcaag atctccatag   2640
ggaagaaatc agtgagtgac caggataact acatcccctg cacgctggag cccgtatttg   2700
gaaagatgtt cgagctgacc tgcactctgc ctctggagaa ggacctaaag atcactctct   2760
atgactatga cctcctctcc aaggacgaaa agatcggtga gacggtcgtc gacctggaga   2820
```

acaggctgct gtccaagttt ggggctcgct gtggactccc acagacctac tgtgtctctg 2880
gaccgaacca gtggcgggac cagctccgcc cctcccagct cctccacctc ttctgccagc 2940
agcatagagt caaggcacct gtgtaccgga cagaccgtgt aatgtttcag gataaagaat 3000
attccattga agagatagag gctggcagga tcccaaaccc acacctgggc ccagtggagg 3060
agcgtctggc tctgcatgtg cttcagcagc agggcctggt cccggagcac gtggagtcac 3120
ggcccctcta cagccccctg cagccagaca tcgagcaggg gaagctgcag atgtgggtcg 3180
acctatttcc gaaggccctg gggcggcctg gacctccctt caacatcacc ccacggagag 3240
ccagaaggtt tttcctgcgt tgtattatct ggaataccag agatgtgatc ctggatgacc 3300
tgagcctcac gggggagaag atgagcgaca tttatgtgaa aggttggatg attggctttg 3360
aagaacacaa gcaaaagaca gacgtgcatt atcgttccct gggaggtgaa ggcaacttca 3420
actggaggtt cattttcccc ttcgactacc tgccagctga gcaagtctgt accattgcca 3480
agaaggatgc cttctggagg ctggacaaga ctgagagcaa aatcccagca cgagtggtgt 3540
tccagatctg ggacaatgac aagttctcct ttgatgattt tctgggctcc ctgcagctcg 3600
atctcaaccg catgcccaag ccagccaaga cagccaagaa gtgctccttg gaccagctgg 3660
atgatgcttt ccacccagaa tggtttgtgt ccctttttga gcagaaaaca gtgaagggct 3720
ggtggccctg tgtagcagaa gagggtgaga agaaaatact ggcgggcaag ctggaaatga 3780
ccttggagat tgtagcagag agtgagcatg aggagcggcc tgctggccag ggccgggatg 3840
agcccaacat gaaccctaag cttgaggacc caaggcgccc cgacacctcc ttcctgtggt 3900
ttacctcccc atacaagacc atgaagttca tcctgtggcg gcgtttccgg tgggccatca 3960
tcctcttcat catcctcttc atcctgctgc tgttcctggc catcttcatc tacgccttcc 4020
cgaactatgc tgccatgaag ctggtgaagc ccttcagctg aggactctcc tgccctgtag 4080
aaggggccgt ggggtcccct ccagcatggg actggcctgc ctcctccgcc cagctcggcg 4140
agctcctcca gacctcctag gcctgattgt cctgccaggg tgggcagaca gacagatgga 4200
ccggcccaca ctcccagagt tgctaacatg gagctctgag atcaccccac ttccatcatt 4260
tccttctccc ccaacccaac gctttttgg atcagctcag acatatttca gtataaaaca 4320
gttggaacca caaaaaaaaa aaaaaaaagt cgacgcggcc gcaataaaag atctttattt 4380
tcattagatc tgtgtgttgg tttttgtgt gtctagagca tggctacgta gataagtagc 4440
atggcgggtt aatcattaac tacaaggaac ccctagtgat ggagttggcc actccctctc 4500
tgcgcgctcg ctcgctcact gaggccgggc gaccaaaggt cgcccgacgc ccgggctttg 4560
cccgggcggc ctcagtgagc gagcgagcgc gc 4592

<210> SEQ ID NO 17
<211> LENGTH: 128
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 3' ITR

<400> SEQUENCE: 17
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgc 128

<210> SEQ ID NO 18
<211> LENGTH: 8341
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Plasmid sequence for DYS F5 Expression Cassette

<400> SEQUENCE: 18
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctctaga gtttaagctt gcatgtctaa 180
gctagaccct tcagattaaa aataactgag gtaagggcct gggtagggga ggtggtgtga 240
gacgctcctg tctctcctct atctgcccat cggccctttg gggaggagga atgtgcccaa 300
ggactaaaaa aaggccatgg agccagaggg gcgagggcaa cagacctttc atgggcaaac 360
cttggggccc tgctgtctag catgccccac tacgggtcta ggctgcccat gtaaggaggc 420
aaggcctggg gacacccgag atgcctggtt ataattaacc cagacatgtg gctgcccccc 480
cccccccaac acctgctgcc tctaaaaata accctgtccc tggtggatcc cctgcatgcg 540
aagatcttcg aacaaggctg tgggggactg agggcaggct gtaacaggct tgggggccag 600
ggcttatacg tgcctgggac tcccaaagta ttactgttcc atgttcccgg cgaagggcca 660
gctgtccccc gccagctaga ctcagcactt agtttaggaa ccagtgagca agtcagccct 720
tggggcagcc catacaaggc catggggctg ggcaagctgc acgcctgggt ccggggtggg 780
cacggtgccc gggcaacgag ctgaaagctc atctgctctc aggggcccct ccctggggac 840
agcccctcct ggctagtcac accctgtagg ctcctctata taacccaggg gcacaggggc 900
tgccctcatt ctaccaccac ctccacagca cagacagaca ctcaggagca gccagcggcg 960
cgcccaggta agtttagtct ttttgtcttt tatttcaggt cccggatccg gtggtggtgc 1020
aaatcaaaga actgctcctc agtggatgtt gcctttactt ctaggcctgt acggaagtgt 1080
tacttctgct ctaaaagctg cggaattgta cccgcggccg cggctagcca ccatgctgag 1140
ggtcttcatc ctctatgccg agaacgtcca cacacccgac accgacatca gcgatgccta 1200
ctgctccgcg gtgtttgcag ggtgaagaa gagaaccaaa gtcatcaaga acagcgtgaa 1260
ccctgtatgg aatgagggat ttgaatggga cctcaagggc atccccctgg accagggctc 1320
tgagcttcat gtggtggtca aagaccatga gacgatgggg aggaacaggt tcctggggga 1380
agccaaggtc ccactccgag aggtcctcgc caccccctagt ctgtccgcca gcttcaatgc 1440
ccccctgctg gacaccaaga agcagcccac aggggcctcg ctggtcctgc aggtgtccta 1500
cacaccgctg cctggagctg tgcccctgtt cccgcccccct actcctctgg agccctcccc 1560
gactctgcct gacctggatg tagtggcaga cacaggagga gaggaagaca cagaggacca 1620
gggactcact ggagatgagg cggagccatt cctggatcaa agcggaggcc cgggggctcc 1680
caccacccca aggaaactac cttcacgtcc tccgccccac taccccggga tcaaaagaaa 1740
gcgaagtgcg cctacatcta gaaagctgct gtcagacaaa ccgcaggatt tccagatcag 1800
ggtccaggtg atcgaggggc gccagctgcc gggggtgaac atcaagcctg tggtcaaggt 1860
taccgctgca gggcagacca agcggacgcg gatccacaag ggaaacagcc cactcttcaa 1920
tgagactctt ttcttcaact tgtttgactc tcctggggag ctgtttgatg agcccatctt 1980
tatcacggtg gtagactctc gttctctcag gacagatgct ctcctcgggg agttccggat 2040
ggacgtgggc accatttaca gagagccccg gcacgcctat ctcaggaagt ggctgctgct 2100
ctcagaccct gatgacttct ctgctggggc cagaggctac ctgaaaacaa gcctttgtgt 2160
gctggggcct ggggacgaag cgcctctgga gagaaaagac ccctctgaag acaaggagga 2220
cattgaaagc aacctgctcc ggcccacagg cgtagccctg cgaggagccc acttctgcct 2280
gaaggtcttc cgggccgagg acttgccgca gatggacgat gccgtgatgg acaacgtgaa 2340
acagatcttt ggcttcgaga gtaacaagaa gaacttggtg gaccccttttg tggaggtcag 2400
ctttgcgggg aaaatgctgt gcagcaagat cttggagaag acggccaacc ctcagtggaa 2460
ccagaacatc acactgcctg ccatgtttcc ctccatgtgc gaaaaaatga ggattcgtat 2520
catagactgg gaccgcctga ctcacaatga catcgtggct accacctacc tgagtatgtc 2580
gaaaatctct gcccctggag gagaaataga agaggagcct gcaggtgctg tcaagccttc 2640
gaaagcctca gacttggatg actacctggg cttcctcccc acttttgggc cctgctacat 2700
caacctctat ggcagtccca gagagttcac aggcttccca gacccctaca cagagctcaa 2760
cacaggcaag gggaaggtg tggcttatcg tggccggctt ctgctctccc tggagaccaa 2820
gctggtggag cacagtgaac agaaggtgga ggaccttcct gcggatgaca tcctccgggt 2880
ggagaagtac cttaggaggc gcaagtactc cctgtttgcg gccttctact cagccaccat 2940
gctgcaggat gtggatgatg ccatccagtt tgaggtcagc atcgggaact acgggaacaa 3000
gttcgacatg acctgcctgc cgctggcctc caccactcag tacagccgtg cagtctttga 3060
cgggtgccac tactactacc taccctgggg taacgtgaaa cctgtggtgg tgctgtcatc 3120
ctactgggag gacatcagcc atagaatcga gactcagaac cagctgcttg ggattgctga 3180
ccggctggaa gctggcctgg agcaggtcca cctggccctg aaggcgcagt gctccacgga 3240
ggacgtggac tcgctggtgg ctcagctgac ggatgagctc atcgcaggct gcagccagcc 3300
tctgggtgac atccatgaga caccctctgc cacccacctg gaccagtacc tgtaccagct 3360
gcgcacccat cacctgagcc aaatcactga ggctgccctg gccctgaagc tcggccacag 3420
tgagctccct gcagctctgg agcaggcgga ggactggctc ctgcgtctgc gtgccctggc 3480
agaggagccc cagaacagcc tgccggacat cgtcatctgg atgctgcagg gagacaagcg 3540
tgtggcatac cagcgggtgc ccgcccacca agtcctcttc tcccggcggg gtgccaacta 3600
ctgtggcaag aattgtggga agctacagac aatctttctg aaatatccga tggagaaggt 3660
gcctggcgcc cggatgccag tgcagatacg ggtcaagctg tggtttgggc tctctgtgga 3720
tgagaaggag ttcaaccagt ttgctgaggg gaagctgtct gtctttgctg aaacctatga 3780
gaacgagact aagttggccc ttgttgggaa ctggggcaca acgggcctca cctaccccaa 3840
gttttctgac gtcacgggca agatcaagct acccaaggac agcttccgcc cctcggccgg 3900
ctggacctgg gctggagatt ggttcgtgtg tccggagaag actctgctcc atgacatgga 3960
cgccggtcac ctgagcttcg tggaagaggt gtttgagaac cagacccggc ttcccggagg 4020
ccagtggatc tacatgagtg acaactacac cgatgtgaac ggggagaagg tgcttcccaa 4080
ggatgacatt gagtgcccac tgggctggaa gtgggaagat gaggaatggt ccacagacct 4140
caaccgggct gtcgatgagc aaggctggga gtatagcatc accatccccc cggagcggaa 4200
gccgaagcac tgggtccctg ctgagaagat gtactacaca caccgacggc ggcgctgggt 4260
gcgcctgcgc aggagggatc tcagccaaat ggaagcactg aaaaggcaca ggcaggcgga 4320
ggcggagggc gagggctggg agtacgcctc tctttttggc tggaagttcc acctcgagta 4380
ccgcaagaca gatgccttcc gccgccgccg ctggcgccgt cgcatggagc cactggagaa 4440
gacggggcct gcagctgtgt ttgcccttga gggcggccgc aataaaagat ctttattttc 4500
attagatctg tgtgttggtt ttttgtgtgt ctagagcatg gcgggttaat cattaactac 4560
aaggaacccc tagtgatgga gttggccact ccctctctgc gcgctcgctc gctcactgag 4620
gccgggcgac caaaggtcgc ccgacgcccg ggctttgccc gggcggcctc agtgagcgag 4680
cgagcgcgca gctgcattaa tgaatcggcc aacgcgcggg gagaggcggt ttgcgtattg 4740
ggcgctcttc cgcttcctcg ctcactgact cgctgcgctc ggtcgttcgg ctgcggcgag 4800
cggtatcagc tcactcaaag gcggtaatac ggttatccac agaatcaggg gataacgcag 4860
gaaagaacat gtgagcaaaa ggccagcaaa aggccaggaa ccgtaaaaag gccgcgttgc 4920
tggcgttttt ccataggctc cgcccccctg acgagcatca caaaaatcga cgctcaagtc 4980
agaggtggcg aaacccgaca ggactataaa gataccaggc gtttccccct ggaagctccc 5040
tcgtgcgctc tcctgttccg accctgccgc ttaccggata cctgtccgcc tttctccctt 5100
cgggaagcgt ggcgctttct catagctcac gctgtaggta tctcagttcg gtgtaggtcg 5160
ttcgctccaa gctgggctgt gtgcacgaac cccccgttca gcccgaccgc tgcgccttat 5220
ccggtaacta tcgtcttgag tccaacccgg taagacacga cttatcgcca ctggcagcag 5280
ccactggtaa caggattagc agagcgaggt atgtaggcgg tgctacagag ttcttgaagt 5340
ggtggcctaa ctacggctac actagaagaa cagtatttgg tatctgcgct ctgctgaagc 5400
cagttacctt cggaaaaaga gttggtagct cttgatccgg caaacaaacc accgctggta 5460
gcggtggttt ttttgtttgc aagcagcaga ttacgcgcag aaaaaaagga tctcaagaag 5520
atcctttgat cttttctacg gggtctgacg ctcagtggaa cgaaaactca cgttaaggga 5580
ttttggtcat gagattatca aaaaggatct tcacctagat ccttttaaat taaaaatgaa 5640
gttttaaatc aatctaaagt atatatgagt aaaaatattc cggaattgcc agctggggcg 5700
ccctctggta aggttgggaa gccctgcaaa gtaaactgga tggctttctt gccgccaagg 5760
atctgatggc gcaggggatc aagatctgat caagagacag gatgaggatc gtttcgcatg 5820
attgaacaag atggattgca cgcaggttct ccggccgctt gggtggagag gctattcggc 5880
tatgactggg cacaacagac aatcggctgc tctgatgccg ccgtgttccg gctgtcagcg 5940
caggggcgcc cggttctttt tgtcaagacc gacctgtccg gtgccctgaa tgaactgcag 6000
gacgaggcag cgcggctatc gtggctggcc acgacgggcg ttccttgcgc agctgtgctc 6060
gacgttgtca ctgaagcggg aagggactgg ctgctattgg gcgaagtgcc ggggcaggat 6120
ctcctgtcat cccaccttgc tcctgccgag aaagtatcca tcatggctga tgcaatgcgg 6180
cggctgcata cgcttgatcc ggctacctgc ccattcgacc accaagcgaa acatcgcatc 6240
gagcgagcac gtactcggat ggaagccggt cttgtcgatc aggatgatct ggacgaagag 6300
catcaggggc tcgcgccagc cgaactgttc gccaggctca aggcgcgcat gcccgacggc 6360
gaggatctcg tcgtgaccca tggcgatgcc tgcttgccga atatcatggt ggaaaatggc 6420
cgcttttctg gattcatcga ctgtggccgg ctgggtgtgg cggaccgcta tcaggacata 6480
gcgttggcta cccgtgatat tgctgaagag cttggcggcg aatgggctga ccgcttcctc 6540
gtgctttacg gtatcgccgc tcccgattcg cagcgcatcg ccttctatcg ccttcttgac 6600
gagttcttct gaaccggtaa tattattgaa gcatttatca gggttattgt ctcatgagcg 6660
gatacatatt tgaatgtatt tagaaaaata aacaaatagg ggttccgcgc acatttcccc 6720
gaaaagtgcc acctgacgtc taagaaacca ttattatcat gacattaacc tataaaaata 6780
ggcgtatcac gaggcccttt cgtctcgcgc gtttcggtga tgacggtgaa aacctctgac 6840
acatgcagct cccggagacg gtcacagctt gtctgtaagc ggatgccggg agcagacaag 6900
cccgtcaggg cgcgtcagcg ggtgttggcg ggtgtcgggg ctggcttaac tatgcggcat 6960
cagagcagat tgtactgaga gtgcaccata tgcggtgtga aataccgcac agatgcgtaa 7020
ggagaaaata ccgcatcagg cgattccaac atccaataaa tcatacaggc aaggcaaaga 7080
attagcaaaa ttaagcaata aagcctcaga gcataaagct aaatcggttg taccaaaaac 7140
attatgaccc tgtaatactt ttgcgggaga agcctttatt tcaacgcaag gataaaaatt 7200
tttagaaccc tcatatattt taaatgcaat gcctgagtaa tgtgtaggta aagattcaaa 7260
cgggtgagaa aggccggaga cagtcaaatc accatcaata tgatattcaa ccgttctagc 7320
tgataaattc atgccggaga gggtagctat ttttgagagg tctctacaaa ggctatcagg 7380
tcattgcctg agagtctgga gcaaacaaga gaatcgatga acggtaatcg taaaactagc 7440
atgtcaatca tatgtacccc ggttgataat cagaaaagcc ccaaaaacag gaagattgta 7500
taagcaaata tttaaattgt aagcgttaat attttgttaa aattcgcgtt aaatttttgt 7560
taaatcagct cattttttaa ccaataggcc gaaatcggca aaatccctta taaatcaaaa 7620
gaatagaccg agatagggtt gagtgttgtt ccagtttgga acaagagtcc actattaaag 7680
aacgtggact ccaacgtcaa agggcgaaaa accgtctatc agggcgatgg cccactacgt 7740
gaaccatcac cctaatcaag ttttttgggg tcgaggtgcc gtaaagcact aaatcggaac 7800
cctaaaggga gcccccgatt tagagcttga cggggaaagc cggcgaacgt ggcgagaaag 7860
gaagggaaga aagcgaaagg agcgggcgct agggcgctgg caagtgtagc ggtcacgctg 7920
cgcgtaacca ccacacccgc cgcgcttaat gcgccgctac agggcgcgta ctatggttgc 7980
tttgacgagc acgtataacg tgctttcctc gttagaatca gagcgggagc taaacaggag 8040
gccgattaaa gggattttag acaggaacgg tacgccagaa tcctgagaag tgtttttata 8100
atcagtgagg ccaccgagta aaagagtctg tccatcacgc aaattaaccg ttgtcgcaat 8160
acttctttga ttagtaataa catcacttgc ctgagtagaa gaactcaaac tatcggcctt 8220
gctggtaata tccagaacaa tattaccgcc agccattgca acggaatcgc cattcgccat 8280
tcaggctgcg caactgttgg gaagggcgat cggtgcgggc ctcttcgcta ttacgccagc 8340
t 8341

<210> SEQ ID NO 19
<211> LENGTH: 8244
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Plasmid sequence for DYS F3 Expression Cassette

<400> SEQUENCE: 19
gtagccatgc tctggtcgac tctagagttt tcgtcatctg gatgctgcag ggagacaagc 60
gtgtggcata ccagcgggtg cccgcccacc aagtcctctt ctcccggcgg ggtgccaact 120
actgtggcaa gaattgtggg aagctacaga caatctttct gaaatatccg atggagaagg 180
tgcctggcgc ccggatgcca gtgcagatac gggtcaagct gtggtttggg ctctctgtgg 240
atgagaagga gttcaaccag tttgctgagg ggaagctgtc tgtctttgct gaaacctatg 300

```
agaacgagac taagttggcc cttgttggga actggggcac aacgggcctc acctacccca    360
agttttctga cgtcacgggc aagatcaagc tacccaagga cagcttccgc ccctcggccg    420
gctggacctg ggctggagat tggttcgtgt gtccggagaa gactctgctc catgacatgg    480
acgccggtca cctgagcttc gtggaagagg tgtttgagaa ccagacccgg cttcccggag    540
gccagtggat ctacatgagt gacaactaca ccgatgtgaa cggggagaag gtgcttccca    600
aggatgacat tgagtgccca ctgggctgga agtgggaaga tgaggaatgg tccacagacc    660
tcaaccgggc tgtcgatgag caaggctggg agtatagcat caccatcccc ccggagcgga    720
agccgaagca ctgggtccct gctgagaaga tgtactacac acaccgacgg cggcgctggg    780
tgcgcctgcg caggagggat ctcagccaaa tggaagcact gaaaaggcac aggcaggcgg    840
aggcggaggg cgagggctgg gagtacgcct ctctttttgg ctggaagttc cacctcgagt    900
accgcaagac agatgccttc cgccgccgcc gctggcgccg tcgcatggag ccactggaga    960
agacggggcc tgcagctgtg tttgcccttg agggggccct gggcggcgtg atggatgaca   1020
agagtgaaga ttccatgtcc gtctccacct tgagcttcgg tgtgaacaga cccacgattt   1080
cctgcatatt cgactatggg aaccgctacc atctacgctg ctacatgtac caggcccggg   1140
acctggctgc gatggacaag gactcttttt ctgatcccta tgccatcgtc tccttcctgc   1200
accagagcca gaagacggtg gtggtgaaga acacccttaa ccccacctgg gaccagacgc   1260
tcatcttcta cgagatcgag atctttggcg agccggccac agttgctgag caaccgccca   1320
gcattgtggt ggagctgtac gaccatgaca cttatggtgc agacgagttt atgggtcgct   1380
gcatctgtca accgagtctg gaacggatgc cacggctggc ctggttccca ctgacgaggg   1440
gcagccagcc gtcgggggag ctgctggcct cttttgagct catccagaga gagaagccgg   1500
ccatccacca tattcctggt tttgaggtgc aggagacatc aaggatcctg gatgagtctg   1560
aggacacaga cctgccctac ccaccacccc agagggaggc caacatctac atggttcctc   1620
agaacatcaa gccagcgctc cagcgtaccg ccatcgagat cctggcatgg ggcctgcgga   1680
acatgaagag ttaccagctg gccaacatct cctcccccag cctcgtggta gagtgtgggg   1740
gccagacggt gcagtcctgt gtcatcagga acctccggaa gaaccccaac tttgacatct   1800
gcaccctctt catggaagtg atgctgccca gggaggagct ctactgcccc cccatcaccg   1860
tcaaggtcat cgataaccgc cagtttggcc gccggcctgt ggtgggccag tgtaccatcc   1920
gctccctgga gagcttcctg tgtgacccct actcggcgga gagtccatcc ccacagggtg   1980
gcccagacga tgtgagccta ctcagtcctg gggaagacgt gctcatcgac attgatgaca   2040
aggagcccct catccccatc caggaggaag agttcatcga ttggtggagc aaattctttg   2100
cctccatagg ggagagggaa aagtgcggct cctacctgga gaaggatttt gacaccctga   2160
aggtctatga cacacagctg gagaatgtgg aggcctttga gggcctgtct gacttttgta   2220
acaccttcaa gctgtaccgg ggcaagacgc aggaggagac agaagatcca tctgtgattg   2280
gtgaatttaa gggcctcttc aaaatttatc ccctcccaga agacccagcc atccccatgc   2340
ccccaagaca gttccaccag ctggccgccc agggacccca ggagtgcttg gtccgtatct   2400
acattgtccg agcatttggc ctgcagccca aggaccccaa tggaaagtgt gatccttaca   2460
tcaagatctc catagggaag aaatcagtga gtgaccagga taactacatc ccctgcacgc   2520
tggagcccgt atttggaaag atgttcgagc tgacctgcac tctgcctctg gagaaggacc   2580
taaagatcac tctctatgac tatgacctcc tctccaagga cgaaaagatc ggtgagacgg   2640
```

tcgtcgacct ggagaacagg ctgctgtcca agtttggggc tcgctgtgga ctcccacaga 2700
cctactgtgt ctctggaccg aaccagtggc gggaccagct ccgcccctcc cagctcctcc 2760
acctcttctg ccagcagcat agagtcaagg cacctgtgta ccggacagac cgtgtaatgt 2820
ttcaggataa agaatattcc attgaagaga tagaggctgg caggatccca aacccacacc 2880
tgggcccagt ggaggagcgt ctggctctgc atgtgcttca gcagcagggc ctggtcccgg 2940
agcacgtgga gtcacggccc ctctacagcc ccctgcagcc agacatcgag caggggaagc 3000
tgcagatgtg ggtcgaccta tttccgaagg ccctggggcg gcctggacct cccttcaaca 3060
tcaccccacg gagagccaga aggtttttcc tgcgttgtat tatctggaat accagagatg 3120
tgatcctgga tgacctgagc ctcacggggg agaagatgag cgacatttat gtgaaaggtt 3180
ggatgattgg ctttgaagaa cacaagcaaa agacagacgt gcattatcgt tccctgggag 3240
gtgaaggcaa cttcaactgg aggttcattt tccccttcga ctacctgcca gctgagcaag 3300
tctgtaccat tgccaagaag gatgccttct ggaggctgga caagactgag agcaaaatcc 3360
cagcacgagt ggtgttccag atctgggaca atgacaagtt ctcctttgat gatttttctgg 3420
gctccctgca gctcgatctc aaccgcatgc ccaagccagc caagacagcc aagaagtgct 3480
ccttggacca gctggatgat gctttccacc cagaatggtt tgtgtccctt tttgagcaga 3540
aaacagtgaa gggctggtgg ccctgtgtag cagaagaggg tgagaagaaa atactggcgg 3600
gcaagctgga aatgaccttg gagattgtag cagagagtga gcatgaggag cggcctgctg 3660
gccagggccg ggatgagccc aacatgaacc ctaagcttga ggacccaagg cgccccgaca 3720
cctccttcct gtggtttacc tccccataca agaccatgaa gttcatcctg tggcggcgtt 3780
tccggtgggc catcatcctc ttcatcatcc tcttcatcct gctgctgttc ctggccatct 3840
tcatctacgc cttcccgaac tatgctgcca tgaagctggt gaagcccttc agctgaggac 3900
tctcctgccc tgtagaaggg gccgtggggt cccctccagc atgggactgg cctgcctcct 3960
ccgcccagct cggcgagctc ctccagacct cctaggcctg attgtcctgc cagggtgggc 4020
agacagacag atggaccggc ccacactccc agagttgcta acatggagct ctgagatcac 4080
cccacttcca tcatttcctt ctcccccaac ccaacgcttt tttggatcag ctcagacata 4140
tttcagtata aaacagttgg aaccacaaaa aaaaaaaaaa aaagtcgacg cggccgcaat 4200
aaaagatctt tattttcatt agatctgtgt gttggttttt tgtgtgtcta gagcatggct 4260
acgtagataa gtagcatggc gggttaatca ttaactacaa ggaaccccta gtgatggagt 4320
tggccactcc ctctctgcgc gctcgctcgc tcactgaggc cgggcgacca aaggtcgccc 4380
gacgcccggg ctttgcccgg gcggcctcag tgagcgagcg agcgcgcagc tgcattaatg 4440
aatcggccaa cgcgcgggga gaggcggttt gcgtattggg cgctcttccg cttcctcgct 4500
cactgactcg ctgcgctcgg tcgttcggct gcggcgagcg gtatcagctc actcaaaggc 4560
ggtaatacgg ttatccacag aatcagggga taacgcagga aagaacatgt gagcaaaagg 4620
ccagcaaaag gccaggaacc gtaaaaaggc cgcgttgctg gcgtttttcc ataggctccg 4680
cccccctgac gagcatcaca aaaatcgacg ctcaagtcag aggtggcgaa acccgacagg 4740
actataaaga taccaggcgt ttccccctgg aagctccctc gtgcgctctc ctgttccgac 4800
cctgccgctt accggatacc tgtccgcctt tctcccttcg ggaagcgtgg cgctttctca 4860
tagctcacgc tgtaggtatc tcagttcggt gtaggtcgtt cgctccaagc tgggctgtgt 4920
gcacgaaccc cccgttcagc ccgaccgctg cgccttatcc ggtaactatc gtcttgagtc 4980
caacccggta agacacgact tatcgccact ggcagcagcc actggtaaca ggattagcag 5040
agcgaggtat gtaggcggtg ctacagagtt cttgaagtgg tggcctaact acggctacac 5100
tagaagaaca gtatttggta tctgcgctct gctgaagcca gttaccttcg gaaaaagagt 5160
tggtagctct tgatccggca aacaaaccac cgctggtagc ggtggttttt ttgtttgcaa 5220
gcagcagatt acgcgcagaa aaaaaggatc tcaagaagat cctttgatct tttctacggg 5280
gtctgacgct cagtggaacg aaaactcacg ttaagggatt ttggtcatga gattatcaaa 5340
aaggatcttc acctagatcc ttttaaatta aaaatgaagt tttaaatcaa tctaaagtat 5400
atatgagtaa aaatattccg gaattgccag ctggggcgcc ctctggtaag gttgggaagc 5460
cctgcaaagt aaactggatg gctttcttgc cgccaaggat ctgatggcgc aggggatcaa 5520
gatctgatca agagacagga tgaggatcgt ttcgcatgat tgaacaagat ggattgcacg 5580
caggttctcc ggccgcttgg gtggagaggc tattcggcta tgactgggca caacagacaa 5640
tcggctgctc tgatgccgcc gtgttccggc tgtcagcgca ggggcgcccg gttctttttg 5700
tcaagaccga cctgtccggt gccctgaatg aactgcagga cgaggcagcg cggctatcgt 5760
ggctggccac gacgggcgtt ccttgcgcag ctgtgctcga cgttgtcact gaagcgggaa 5820
gggactggct gctattgggc gaagtgccgg ggcaggatct cctgtcatcc caccttgctc 5880
ctgccgagaa agtatccatc atggctgatg caatgcggcg gctgcatacg cttgatccgg 5940
ctacctgccc attcgaccac caagcgaaac atcgcatcga gcgagcacgt actcggatgg 6000
aagccggtct tgtcgatcag gatgatctgg acgaagagca tcaggggctc gcgccagccg 6060
aactgttcgc caggctcaag gcgcgcatgc ccgacggcga ggatctcgtc gtgacccatg 6120
gcgatgcctg cttgccgaat atcatggtgg aaaatggccg cttttctgga ttcatcgact 6180
gtggccggct gggtgtggcg gaccgctatc aggacatagc gttggctacc cgtgatattg 6240
ctgaagagct tggcggcgaa tgggctgacc gcttcctcgt gctttacggt atcgccgctc 6300
ccgattcgca gcgcatcgcc ttctatcgcc ttcttgacga gttcttctga accggtaata 6360
ttattgaagc atttatcagg gttattgtct catgagcgga tacatatttg aatgtattta 6420
gaaaaataaa caaatagggg ttccgcgcac atttccccga aaagtgccac ctgacgtcta 6480
agaaaccatt attatcatga cattaaccta taaaaatagg cgtatcacga ggccctttcg 6540
tctcgcgcgt ttcggtgatg acggtgaaaa cctctgacac atgcagctcc cggagacggt 6600
cacagcttgt ctgtaagcgg atgccgggag cagacaagcc cgtcagggcg cgtcagcggg 6660
tgttggcggg tgtcggggct ggcttaacta tgcggcatca gagcagattg tactgagagt 6720
gcaccatatg cggtgtgaaa taccgcacag atgcgtaagg agaaaatacc gcatcaggcg 6780
attccaacat ccaataaatc atacaggcaa ggcaaagaat tagcaaaatt aagcaataaa 6840
gcctcagagc ataaagctaa atcggttgta ccaaaaacat tatgaccctg taatactttt 6900
gcgggagaag cctttatttc aacgcaagga taaaaatttt tagaaccctc atatatttta 6960
aatgcaatgc ctgagtaatg tgtaggtaaa gattcaaacg ggtgagaaag gccggagaca 7020
gtcaaatcac catcaatatg atattcaacc gttctagctg ataaattcat gccggagagg 7080
gtagctattt ttgagaggtc tctacaaagg ctatcaggtc attgcctgag agtctggagc 7140
aaacaagaga atcgatgaac ggtaatcgta aaactagcat gtcaatcata tgtaccccgg 7200
ttgataatca gaaaagcccc aaaaacagga agattgtata agcaaatatt taaattgtaa 7260
gcgttaatat tttgttaaaa ttcgcgttaa atttttgtta aatcagctca ttttttaacc 7320
aataggccga aatcggcaaa atcccttata aatcaaaaga atagaccgag atagggttga 7380
gtgttgttcc agtttggaac aagagtccac tattaaagaa cgtggactcc aacgtcaaag 7440
ggcgaaaaac cgtctatcag ggcgatggcc cactacgtga accatcaccc taatcaagtt 7500
ttttggggtc gaggtgccgt aaagcactaa atcggaaccc taaagggagc ccccgattta 7560
gagcttgacg gggaaagccg gcgaacgtgg cgagaaagga agggaagaaa gcgaaaggag 7620
cgggcgctag ggcgctggca agtgtagcgg tcacgctgcg cgtaaccacc acacccgccg 7680
cgcttaatgc gccgctacag ggcgcgtact atggttgctt tgacgagcac gtataacgtg 7740
ctttcctcgt tagaatcaga gcgggagcta aacaggaggc cgattaaagg gattttagac 7800
aggaacggta cgccagaatc ctgagaagtg tttttataat cagtgaggcc accgagtaaa 7860
agagtctgtc catcacgcaa attaaccgtt gtcgcaatac ttctttgatt agtaataaca 7920
tcacttgcct gagtagaaga actcaaacta tcggccttgc tggtaatatc cagaacaata 7980
ttaccgccag ccattgcaac ggaatcgcca ttcgccattc aggctgcgca actgttggga 8040
agggcgatcg gtgcgggcct cttcgctatt acgccagctg cgcgctcgct cgctcactga 8100
ggccgcccgg gcaaagcccg ggcgtcgggc gacctttggt cgcccggcct cagtgagcga 8160
gcgagcgcgc agagagggag tggccaactc catcactagg ggttccttgt agttaatgat 8220
taacccgcca tgctacttat ctac 8244

<210> SEQ ID NO 20
<211> LENGTH: 7906
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: full DYF expression cassette

<400> SEQUENCE: 20
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctctaga gtttaagctt gcatgtctaa 180
gctagaccct tcagattaaa aataactgag gtaagggcct gggtagggga ggtggtgtga 240
gacgctcctg tctctcctct atctgcccat cggccctttg gggaggagga atgtgcccaa 300
ggactaaaaa aaggccatgg agccagaggg gcgagggcaa cagacctttc atgggcaaac 360
cttggggccc tgctgtctag catgccccac tacgggtcta ggctgcccat gtaaggaggc 420
aaggcctggg gacacccgag atgcctggtt ataattaacc cagacatgtg gctgcccccc 480
cccccccaac acctgctgcc tctaaaaata accctgtccc tggtggatcc cctgcatgcg 540
aagatcttcg aacaaggctg tgggggactg agggcaggct gtaacaggct tgggggccag 600
ggcttatacg tgcctgggac tcccaaagta ttactgttcc atgttcccgg cgaagggcca 660
gctgtccccc gccagctaga ctcagcactt agtttaggaa ccagtgagca agtcagccct 720
tggggcagcc catacaaggc catggggctg ggcaagctgc acgcctgggt ccggggtggg 780
cacggtgccc gggcaacgag ctgaaagctc atctgctctc aggggcccct ccctggggac 840
agcccctcct ggctagtcac accctgtagg ctcctctata taacccaggg gcacaggggc 900
tgccctcatt ctaccaccac ctccacagca cagacagaca ctcaggagca gccagcggcg 960
cgcccaggta agtttagtct ttttgtcttt tatttcaggt cccggatccg gtggtggtgc 1020
aaatcaaaga actgctcctc agtggatgtt gcctttactt ctaggcctgt acggaagtgt 1080

```
tacttctgct ctaaaagctg cggaattgta cccgcggccg cggctagcca ccatgctgag   1140
ggtcttcatc ctctatgccg agaacgtcca cacacccgac accgacatca gcgatgccta   1200
ctgctccgcg gtgtttgcag ggtgaagaa gagaaccaaa gtcatcaaga acagcgtgaa    1260
ccctgtatgg aatgagggat ttgaatggga cctcaagggc atccccctgg accagggctc   1320
tgagcttcat gtggtggtca aagaccatga gacgatgggg aggaacaggt tcctggggga   1380
agccaaggtc ccactccgag aggtcctcgc cacccctagt ctgtccgcca gcttcaatgc   1440
ccccctgctg gacaccaaga agcagcccac aggggcctcg ctggtcctgc aggtgtccta   1500
cacaccgctg cctggagctg tgcccctgtt cccgcccccct actcctctgg agccctcccc  1560
gactctgcct gacctggatg tagtggcaga cacaggagga gaggaagaca cagaggacca   1620
gggactcact ggagatgagg cggagccatt cctggatcaa agcggaggcc cgggggctcc   1680
caccacccca aggaaactac cttcacgtcc tccgccccac taccccggga tcaaaagaaa   1740
gcgaagtgcg cctacatcta gaaagctgct gtcagacaaa ccgcaggatt tccagatcag   1800
ggtccaggtg atcgaggggc gccagctgcc gggggtgaac atcaagcctg tggtcaaggt   1860
taccgctgca gggcagacca agcggacgcg gatccacaag ggaaacagcc cactcttcaa   1920
tgagactctt ttcttcaact tgtttgactc tcctggggag ctgtttgatg agcccatctt   1980
tatcacggtg gtagactctc gttctctcag gacagatgct ctcctcgggg agttccggat   2040
ggacgtgggc accatttaca gagagccccg gcacgcctat ctcaggaagt ggctgctgct   2100
ctcagaccct gatgacttct ctgctggggc cagaggctac ctgaaaacaa gcctttgtgt   2160
gctggggcct ggggacgaag cgcctctgga gagaaaagac ccctctgaag acaaggagga   2220
cattgaaagc aacctgctcc ggcccacagg cgtagccctg cgaggagccc acttctgcct   2280
gaaggtcttc cgggccgagg acttgccgca gatggacgat gccgtgatgg acaacgtgaa   2340
acagatcttt ggcttcgaga gtaacaagaa gaacttggtg gaccccttttg tggaggtcag  2400
ctttgcgggg aaaatgctgt gcagcaagat cttggagaag acggccaacc ctcagtggaa   2460
ccagaacatc acactgcctg ccatgtttcc ctccatgtgc gaaaaaatga ggattcgtat   2520
catagactgg gaccgcctga ctcacaatga catcgtggct accacctacc tgagtatgtc   2580
gaaaatctct gcccctggag gagaaataga agaggagcct gcaggtgctg tcaagccttc   2640
gaaagcctca gacttggatg actacctggg cttcctcccc acttttgggc cctgctacat   2700
caacctctat ggcagtccca gagagttcac aggcttccca gacccctaca cagagctcaa   2760
cacaggcaag gggaaggtg tggcttatcg tggccggctt ctgctctccc tggagaccaa    2820
gctggtggag cacagtgaac agaaggtgga ggaccttcct gcggatgaca tcctccgggt   2880
ggagaagtac cttaggaggc gcaagtactc cctgtttgcg gccttctact cagccaccat   2940
gctgcaggat gtggatgatg ccatccagtt tgaggtcagc atcgggaact acgggaacaa   3000
gttcgacatg acctgcctgc cgctggcctc caccactcag tacagccgtg cagtctttga   3060
cgggtgccac tactactacc taccctgggg taacgtgaaa cctgtggtgg tgctgtcatc   3120
ctactgggag gacatcagcc atagaatcga gactcagaac cagctgcttg ggattgctga   3180
ccggctggaa gctggcctgg agcaggtcca cctggccctg aaggcgcagt gctccacgga   3240
ggacgtggac tcgctggtgg ctcagctgac ggatgagctc atcgcaggct gcagccagcc   3300
tctgggtgac atccatgaga caccctctgc cacccacctg gaccagtacc tgtaccagct   3360
gcgcacccat cacctgagcc aaatcactga ggctgccctg gccctgaagc tcggccacag   3420
tgagctccct gcagctctgg agcaggcgga ggactggctc ctgcgtctgc gtgccctggc   3480
```

agaggagccc cagaacagcc tgccggacat cgtcatctgg atgctgcagg gagacaagcg 3540
tgtggcatac cagcgggtgc ccgcccacca agtcctcttc tcccggcggg gtgccaacta 3600
ctgtggcaag aattgtggga agctacagac aatctttctg aaatatccga tggagaaggt 3660
gcctggcgcc cggatgccag tgcagatacg ggtcaagctg tggtttgggc tctctgtgga 3720
tgagaaggag ttcaaccagt ttgctgaggg gaagctgtct gtctttgctg aaacctatga 3780
gaacgagact aagttggccc ttgttgggaa ctggggcaca acgggcctca cctaccccaa 3840
gttttctgac gtcacgggca agatcaagct acccaaggac agcttccgcc cctcggccgg 3900
ctggacctgg gctggagatt ggttcgtgtg tccggagaag actctgctcc atgacatgga 3960
cgccggtcac ctgagcttcg tggaagaggt gtttgagaac cagacccggc ttcccggagg 4020
ccagtggatc tacatgagtg acaactacac cgatgtgaac ggggagaagg tgcttcccaa 4080
ggatgacatt gagtgcccac tgggctggaa gtgggaagat gaggaatggt ccacagacct 4140
caaccgggct gtcgatgagc aaggctggga gtatagcatc accatccccc cggagcggaa 4200
gccgaagcac tgggtccctg ctgagaagat gtactacaca caccgacggc ggcgctgggt 4260
gcgcctgcgc aggagggatc tcagccaaat ggaagcactg aaaaggcaca ggcaggcgga 4320
ggcggagggc gagggctggg agtacgcctc tctttttggc tggaagttcc acctcgagta 4380
ccgcaagaca gatgccttcc gccgccgccg ctggcgccgt cgcatggagc cactggagaa 4440
gacggggcct gcagctgtgt ttgcccttga gggggccctg ggcggcgtga tggatgacaa 4500
gagtgaagat tccatgtccg tctccacctt gagcttcggt gtgaacagac ccacgatttc 4560
ctgcatattc gactatggga accgctacca tctacgctgc tacatgtacc aggcccggga 4620
cctggctgcg atggacaagg actctttttc tgatccctat gccatcgtct ccttcctgca 4680
ccagagccag aagacggtgg tggtgaagaa cacccttaac ccccacctgg accagacgct 4740
catcttctac gagatcgaga tctttggcga gccggccaca gttgctgagc aaccgcccag 4800
cattgtggtg gagctgtacg accatgacac ttatggtgca gacgagttta tgggtcgctg 4860
catctgtcaa ccgagtctgg aacggatgcc acggctggcc tggttcccac tgacgagggg 4920
cagccagccg tcgggggagc tgctggcctc ttttgagctc atccagagag agaagccggc 4980
catccaccat attcctggtt ttgaggtgca ggagacatca aggatcctgg atgagtctga 5040
ggacacagac ctgccctacc caccacccca gagggaggcc aacatctaca tggttcctca 5100
gaacatcaag ccagcgctcc agcgtaccgc catcgagatc ctggcatggg gcctgcggaa 5160
catgaagagt taccagctgg ccaacatctc ctcccccagc ctcgtggtag agtgtggggg 5220
ccagacggtg cagtcctgtg tcatcaggaa cctccggaag aaccccaact ttgacatctg 5280
caccctcttc atggaagtga tgctgcccag ggaggagctc tactgccccc ccatcaccgt 5340
caaggtcatc gataaccgcc agtttggccg ccggcctgtg gtgggccagt gtaccatccg 5400
ctccctggag agcttcctgt gtgaccccta ctcggcggag agtccatccc cacagggtgg 5460
cccagacgat gtgagcctac tcagtcctgg ggaagacgtg ctcatcgaca ttgatgacaa 5520
ggagcccctc atccccatcc aggaggaaga gttcatcgat tggtggagca aattctttgc 5580
ctccataggg gagagggaaa agtgcggctc ctacctggag aaggattttg acaccctgaa 5640
ggtctatgac acacagctgg agaatgtgga ggcctttgag ggcctgtctg acttttgtaa 5700
caccttcaag ctgtaccggg gcaagacgca ggaggagaca gaagatccat ctgtgattgg 5760
tgaatttaag ggcctcttca aaatttatcc cctcccagaa gacccagcca tccccatgcc 5820

```
cccaagacag ttccaccagc tggccgccca gggaccccag gagtgcttgg tccgtatcta   5880
cattgtccga gcatttggcc tgcagcccaa ggaccccaat ggaaagtgtg atccttacat   5940
caagatctcc atagggaaga aatcagtgag tgaccaggat aactacatcc cctgcacgct   6000
ggagcccgta tttggaaaga tgttcgagct gacctgcact ctgcctctgg agaaggacct   6060
aaagatcact ctctatgact atgacctcct ctccaaggac gaaaagatcg gtgagacggt   6120
cgtcgacctg gagaacaggc tgctgtccaa gtttggggct cgctgtggac tcccacagac   6180
ctactgtgtc tctggaccga accagtggcg ggaccagctc cgcccctccc agctcctcca   6240
cctcttctgc cagcagcata gagtcaaggc acctgtgtac cggacagacc gtgtaatgtt   6300
tcaggataaa gaatattcca ttgaagagat agaggctggc aggatcccaa acccacacct   6360
gggcccagtg gaggagcgtc tggctctgca tgtgcttcag cagcagggcc tggtcccgga   6420
gcacgtggag tcacggcccc tctacagccc cctgcagcca gacatcgagc aggggaagct   6480
gcagatgtgg gtcgacctat ttccgaaggc cctggggcgg cctggacctc ccttcaacat   6540
caccccacgg agagccagaa ggtttttcct gcgttgtatt atctggaata ccagagatgt   6600
gatcctggat gacctgagcc tcacggggga gaagatgagc gacatttatg tgaaaggttg   6660
gatgattggc tttgaagaac acaagcaaaa gacagacgtg cattatcgtt ccctgggagg   6720
tgaaggcaac ttcaactgga ggttcatttt ccccttcgac tacctgccag ctgagcaagt   6780
ctgtaccatt gccaagaagg atgccttctg gaggctggac aagactgaga gcaaaatccc   6840
agcacgagtg gtgttccaga tctgggacaa tgacaagttc tcctttgatg attttctggg   6900
ctccctgcag ctcgatctca accgcatgcc caagccagcc aagacagcca agaagtgctc   6960
cttggaccag ctggatgatg ctttccaccc agaatggttt gtgtcccttt ttgagcagaa   7020
aacagtgaag ggctggtggc cctgtgtagc agaagagggt gagaagaaaa tactggcggg   7080
caagctggaa atgaccttgg agattgtagc agagagtgag catgaggagc ggcctgctgg   7140
ccagggccgg gatgagccca acatgaaccc taagcttgag gacccaaggc gccccgacac   7200
ctccttcctg tggtttacct ccccatacaa gaccatgaag ttcatcctgt ggcggcgttt   7260
ccggtgggcc atcatcctct tcatcatcct cttcatcctg ctgctgttcc tggccatctt   7320
catctacgcc ttcccgaact atgctgccat gaagctggtg aagcccttca gctgaggact   7380
ctcctgccct gtagaagggg ccgtggggtc ccctccagca tgggactggc ctgcctcctc   7440
cgcccagctc ggcgagctcc tccagacctc ctaggcctga ttgtcctgcc agggtgggca   7500
gacagacaga tggaccggcc cacactccca gagttgctaa catggagctc tgagatcacc   7560
ccacttccat catttccttc tcccccaacc caacgctttt ttggatcagc tcagacatat   7620
ttcagtataa aacagttgga accacaaaaa aaaaaaaaaa aagtcgacgc ggccgcaata   7680
aaagatcttt attttcatta gatctgtgtg ttggtttttt gtgtgtctag agcatggcta   7740
cgtagataag tagcatggcg ggttaatcat taactacaag gaacccctag tgatggagtt   7800
ggccactccc tctctgcgcg ctcgctcgct cactgaggcc gggcgaccaa aggtcgcccg   7860
acgcccgggc tttgcccggg cggcctcagt gagcgagcga gcgcgc                  7906
```

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag -continued

```
<400> SEQUENCE: 21

His His His His His His
1               5


<210> SEQ ID NO 22
<211> LENGTH: 250
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(250)
<223> OTHER INFORMATION: This sequence may encompass 100-250 nucleotides

<400> SEQUENCE: 22

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa                                                           250
```